US012584114B2

(12) United States Patent
Stephan

(10) Patent No.: US 12,584,114 B2
(45) **Date of Patent: *Mar. 24, 2026**

(54) COMPOSITIONS AND METHODS FOR DELIVERY OF IMMUNE CELLS TO TREAT UN-RESECTABLE OR NON-RESECTED TUMOR CELLS AND TUMOR RELAPSE

(71) Applicant: FRED HUTCHINSON CANCER CENTER, Seattle, WA (US)

(72) Inventor: Matthias Stephan, Seattle, WA (US)

(73) Assignee: Fred Hutchinson Cancer Center, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/403,553

(22) Filed: Jan. 3, 2024

(65) Prior Publication Data

US 2024/0122984 A1 Apr. 18, 2024

Related U.S. Application Data

(63) Continuation of application No. 17/039,671, filed on Sep. 30, 2020, now Pat. No. 11,890,303, which is a continuation of application No. 16/156,996, filed on Oct. 10, 2018, now Pat. No. 10,806,756, which is a continuation of application No. 16/155,801, filed on Oct. 9, 2018, now Pat. No. 10,702,551, which is a continuation of application No. 14/760,695, filed as application No. PCT/US2014/011526 on Jan. 14, 2014, now abandoned.

(60) Provisional application No. 61/900,922, filed on Nov. 6, 2013, provisional application No. 61/752,423, filed on Jan. 14, 2013.

(51) Int. Cl.
| | |
|---|---|
| *A61K 40/11* | (2025.01) |
| *A01K 67/0271* | (2024.01) |
| *A61K 9/00* | (2006.01) |
| *A61K 9/14* | (2006.01) |
| *A61K 39/44* | (2006.01) |
| *A61K 40/42* | (2025.01) |
| *A61K 45/06* | (2006.01) |
| *C07K 16/28* | (2006.01) |
| *C12N 5/09* | (2010.01) |

(52) U.S. Cl.
CPC ........ *C12N 5/0694* (2013.01); *A01K 67/0271* (2013.01); *A61K 9/0024* (2013.01); *A61K 9/146* (2013.01); *A61K 39/44* (2013.01); *A61K 40/11* (2025.01); *A61K 40/42* (2025.01); *A61K 45/06* (2013.01); *C07K 16/2809* (2013.01); *C07K 16/2818* (2013.01); *C07K 16/2878* (2013.01); *A01K 2207/12* (2013.01); *A01K 2227/105* (2013.01); *A01K 2267/0331* (2013.01); *A61K 2239/31* (2023.05); *A61K 2239/38* (2023.05); *A61K 2239/49* (2023.05);

*C12N 2510/00* (2013.01); *C12N 2533/54* (2013.01); *C12N 2533/74* (2013.01)

(58) Field of Classification Search
None
See application file for complete search history.

(56) References Cited

U.S. PATENT DOCUMENTS

| | | | |
|---|---|---|---|
| 8,114,431 | B2 | 2/2012 | Garcia et al. |
| 8,445,006 | B2 | 5/2013 | Garcia et al. |
| 9,393,199 | B2 | 7/2016 | Irvine et al. |
| 2002/0062154 | A1 | 5/2002 | Ayers |
| 2006/0067909 | A1 | 3/2006 | West et al. |
| 2008/0131425 | A1 | 6/2008 | Garcia et al. |
| 2011/0014217 | A1 | 1/2011 | Fahmy et al. |
| 2011/0293705 | A1 | 12/2011 | Irvine et al. |
| 2012/0134967 | A1 | 5/2012 | Mooney et al. |
| 2012/0142597 | A1 | 6/2012 | Garcia et al. |
| 2012/0245706 | A1 | 9/2012 | Alavi |
| 2013/0202707 | A1 | 8/2013 | Ali et al. |
| 2014/0079774 | A1 | 3/2014 | Brinker et al. |
| 2014/0180399 | A1 | 6/2014 | Alavi |
| 2016/0008399 | A1 | 1/2016 | Stephan |
| 2016/0235564 | A1 | 8/2016 | Johnson et al. |
| 2016/0287623 | A1 | 10/2016 | Gajewski et al. |
| 2017/0340658 | A1 | 11/2017 | Vernejoul et al. |
| 2019/0046572 | A1 | 2/2019 | Stephan |
| 2019/0054121 | A1 | 2/2019 | Stephan |
| 2019/0336532 | A1 | 11/2019 | Stephan et al. |

FOREIGN PATENT DOCUMENTS

| | | |
|---|---|---|
| CN | 107428810 A | 12/2017 |
| WO | 2011063336 A2 | 5/2011 |
| WO | 2011130322 A1 | 10/2011 |
| (Continued) | | |

OTHER PUBLICATIONS

Khong, et al., "Natural selection of tumor variants in the generation of "tumor escape" phenotypes", nature immunology, vol. 3, No. 11, Nov. 2002, pp. 999-1005.

(Continued)

*Primary Examiner* — Daniel C Gamett

(74) *Attorney, Agent, or Firm* — C. Rachal Winger; Lee & Hayes PC

(57) ABSTRACT

The present disclosure provides compositions and methods for the delivery of immune cells to treat un-resectable or non-resected tumor cells and tumor relapse. The compositions comprise (i) a structure comprising an injectable polymer or scaffold comprising pores; (ii) lymphocytes disposed within the structure, (iii) at least one lymphocyte-adhesion moiety associated with the structure; and (iv) at least one lymphocyte-activating moiety associated with the structure, and optionally an immune stimulant.

21 Claims, 27 Drawing Sheets

Specification includes a Sequence Listing.

(56)                References Cited

FOREIGN PATENT DOCUMENTS

WO          2014110591 A1       7/2014
WO          2016096577 A1       6/2016
WO          2016145102 A1       9/2016
WO          2016161372          10/2016
WO          2016079899 A1       8/2017

OTHER PUBLICATIONS

Office Action for Japanese Application No. 2022-097810, Dated May 28, 2024, 6 pages.
Search Report and Written Opinion for European Application No. 23215104.3, Dated Jul. 29, 2024, 18 pages.
Adu-Berchie, et al., "Filmed over with CAR-T cells," Nature Biomedical Engineering, vol. 4, No. 2, 2020, pp. 142-143.
Ali, et al., "In situ regulation of DC subsets and T cells mediates tumor regression in mice," Sci. Transl. Med., vol. 1, No. 8, 2009, 8ra19, 22 pages.
An, et al., "Design and 3D Printing of Scaffolds and Tissues," Engineering, vol. 1, No. 2, 2015, pp. 261-268.
Baldwin & Kiick, "Polysaccharide-modified synthetic polymeric biomaterials," Biopolymers, vol. 94, No. 1, 2010, pp. 128-140.
Boateng, et al., "RGD and YIGSR synthetic peptides facilitate cellular adhesion identical to that of laminin and fibronectin but alter the physiology of neonatal cardiac myocytes," Am. J. Physiol. Cell Physio., vol. 288, No. 1, 2005, pp. 30-38.
Boontheekul, et al., "Controlling alginate gel degradation utilizing partial oxidation and bimodal molecular weight distribution," Biomaterials, vol. 26, No. 15, 2005, pp. 2455-2465.
Coon, et al., "Nitinol thin films functionalized with CAR-T cells for the treatment of solid tumours," Nature Biomedical Engineering, vol. 4, No. 2, 2019, pp. 195-206.
Chinese Office Action mailed Jul. 30, 2023 for Chinese Patent Application No. 201780079628.7, a foreign counterpart to US Patent No. U.S. Appl. No. 16/472,764, 24 pages.
Chinese Office Action mailed Oct. 10, 2022 for Chinese Patent Application No. 201780079628.7, a foreign counterpart to U.S. Appl. No. 16/472,764, 25 pages.
European Office Action mailed on Jun. 16, 2023 for European Patent Application No. 17883391.9, a foreign counterpart to U.S. Appl. No. 14/760,695, 6 pages.
Japanese Office Action mailed Feb. 1, 2022 for Japanese Patent Application No. 2019-534814, a foreign counterpart to U.S. Appl. No. 16/472,764, 7 pages.
European Search Report Dated Jul. 6, 2016 for European Application No. 14737656.0.
Extended European Search Report Dated Nov. 10, 2020 for European Application No. 17883391.9, 15 pages.
Gammon, et al., "Improving the clinical impact of biomaterials in cancer immunotherapy," Oncotarget, vol. 7, No. 13, 2016, pp. 15421-15443.
Hanson, et. al., "Nanoparticulate STING agonists are potent lymph node-targeted vaccine adjuvants", Technical Advance, The Journal of Clincal Investigation, vol. 125, No. 6, 2015, pp. 2532-2546.
Hansson, et al., "Whole blood coagulation on protein adsorption-resistant PEG and peptide functionalised PEG-coated titanium surfaces," Biomaterials, vol. 26, No. 8, 2005, pp. 861-872.
Hingorani, et al., "Trp53R172H and KrasG12D cooperate to promote chromosomal instability and widely metastatic pancreatic ductal adenocarcinoma in mice," Cancer Cell, vol. 7, No. 5, 2005, pp. 469-483.
Invitation to Pay Additional Fees Dated Mar. 20, 2018 for International Application No. PCT/US2017/067965, 2 pages.
Japanese Office Action mailed Aug. 29, 2023 for Japanese Patent Application No. 2022-097810, a foreign counterpart to U.S. Appl. No. 16/472,764, 5 pages.
Jun, et al., "Development of a YIGSR-peptide-modified polyurethaneurea to enhance endothelialization," J. Biomaterials Sci. Polymer Ed., vol. 15, No. 1, 2004, pp. 73-94.

Kim, et al., "Injectable, spontaneously assembling, inorganic scaffolds modulate immune cells in vivo and increase vaccine efficacy," Nat. Biotechnol., vol. 33, No. 1, 2015, pp. 64-72.
Kim, et al., "In Vivo Modulation of Dendritic Cells by Engineered Materials: Towards New Cancer Vaccines", Nano Today, vol. 6, 2011, pp. 466-477.
Koshy, et al., "Biomaterials for enhancing anti-cancer immunity," Current Opinion in Biotechnology, vol. 40, 2016, pp. 1-8.
Lee, et al., "Three-Dimensional Collagen/Alginate Hybrid Scaffolds Functionalized with a Drug Delivery System (DDS) for Bone Tissue Regeneration," Chem. Mater., vol. 24, No. 5, 2012, pp. 881-891.
Levengood, et al., "Chitosan-based scaffolds for bone tissue engineering," J. Mater. Chem. B, vol. 2, No. 21, 2014, pp. 3161-3184.
Li, et al., "Effects of filtration seeding on cell density, spatial distribution, and proliferation in nonwoven fibrous matrices," Biotechnol. Prog., vol. 17, No. 5, 2001, pp. 935-944.
Lin, et al., "Synthesis, surface, and cell-adhesion properties of polyurethanes containing covalently grafted RGD-peptides," J. Biomedical Materials Res., vol. 28, No. 3, 1994, pp. 329-342.
Non Final Office Action dated Jan. 21, 2020 for U.S. Appl. No. 16/156,996 "Compositions and Methods for Delivery of Immune Cells to Treat Un-Resectable or Non-Resected Tumor Cells and Tumor Relapse" Stephan, 5 pages.
Office Action Dated Feb. 9, 2017 for European Application No. 14737656.0, 6 pages.
Office Action Dated Jan. 4, 2018 in U.S. Appl. No. 14/760,695, 6 pages.
Office Action Dated Sep. 28, 2017 in U.S. Appl. No. 14/760,695, 5 pages.
Office Action for U.S. Appl. No. 16/472,764 , mailed on Oct. 17, 2022, Stephan, "Scaffolds to Treat Solid Tumor Cells and Escape Variants", 11 Pages.
Office Action for U.S. Appl. No. 16/472,764, mailed on Mar. 28, 2023, Stephan, "Scaffolds to Treat Solid Tumor Cells and Escape Variants", 11 Pages.
Office Action for U.S. Appl. No. 16/472,764, mailed on Sep. 1, 2021, Stephan, "Scaffolds to Treat Solid Tumor Cells and Escape Variants", 15 Pages.
Rigberg, et al., "Thin-film nitinol (NiTi): a feasibility study for a novel aortic stent graft material," J. Vasc. Surg., vol. 50, No. 2, 2009, pp. 375-380.
Search Report and Written Opinion Dated Apr. 14, 2014 in PCT/US14/11526.
Search Report and Written Opinion Dated May 11, 2018, for International Application No. PCT/US2017/067965, 22 pages.
Shabalovskaya, et al., "Critical Overview of Nitinol Surfaces and their modifications for medical applications," Acta Biomaterialia, vol. 4, 2008, pp. 447-467.
Singh, et al., "3D Printing of Scaffold for Cells Delivery: Advances in Skin Tissue Engineering," Polymers, Voll 8, No. 1, 2016, 17 pages.
Sittinger, et al., "Artificial tissues in perfusion culture," Int. J. Artif. Organs, vol. 20, No. 1, 1997, pp. 57-62.
Smith, et al., "Biopolymers codelivering engineered T-cells and STING agonists can eliminate heterogeneous tumors," The Journal of Clinical Investigation, vol. 127, No. 6, 2017, pp. 195-206.
Song, "History and Current Situation of Shape Memory Alloys Devices for Minimally Invasive Surgery," The Open Medical Devices Journal, vol. 2, No. 2, 2010, pp. 24-31.
Stephan, et al., "Biopolymer implants enhance the efficacy of adoptive T-cell therapy", Nature Biotechnology, vol. 33, No. 1, 2014, pp. 97-101.
Stephan, et al., "Supporting Online Material for Biopolymer implants enhance the efficacy of adoptive T-cell therapy," Nature Biotechnology, vol. 33, No. 1, 2014, pp. 97-101.
Wang, et al., "Selective Tumor Cell Inhibition Effect of Ni—Ti Layered Double Hydroxides Thin Films Driven by the Reversed pH Gradients of Tumor Cells," ACS Applied Materials & Interfaces, vol. 7, No. 15, 2015, pp. 7843-7854.
Wendt, et al., "Oscillating perfusion of cell suspensions through three-dimensional scaffolds enhances cell seeding efficiency and uniformity," Biotechnol. Bioeng., No. 84, No. 2, 2003, pp. 205-214.

(56) References Cited

OTHER PUBLICATIONS

Yang, et al, "Therapeutic potential and challenges of targeting receptor tyrosine kinase ROR1 with monoclonal antibodies in B-cell malignancies," Plos One, vol. 6, No. 6, 2011, e21018, 15 pages.

Yang, et al., "Novel cell immobilization method utilizing centrifugal force to achieve high-density hepatocyte culture in porous scaffold," J. Biomed. Mater. Res, No. 55, No. 3, 2001, pp. 379-386.

Zacco, et al., "A Self-Assembling Peptide Scaffold for the Multivalent Presentation of Antigens," Biomacromolecules, vol. 16, No. 7, 2015, pp. 2188-2197.

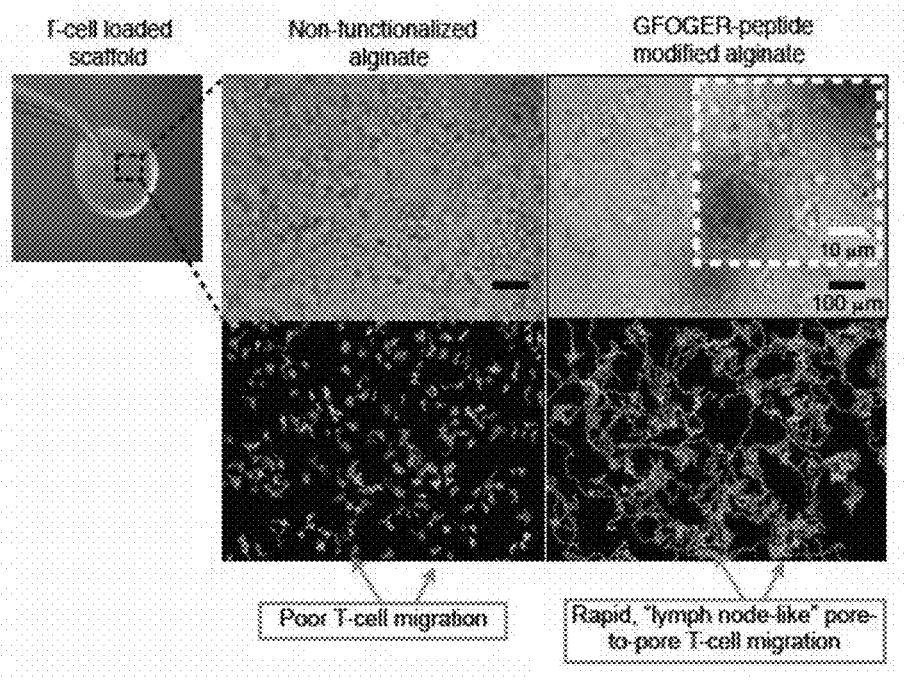
FIG. 6C.
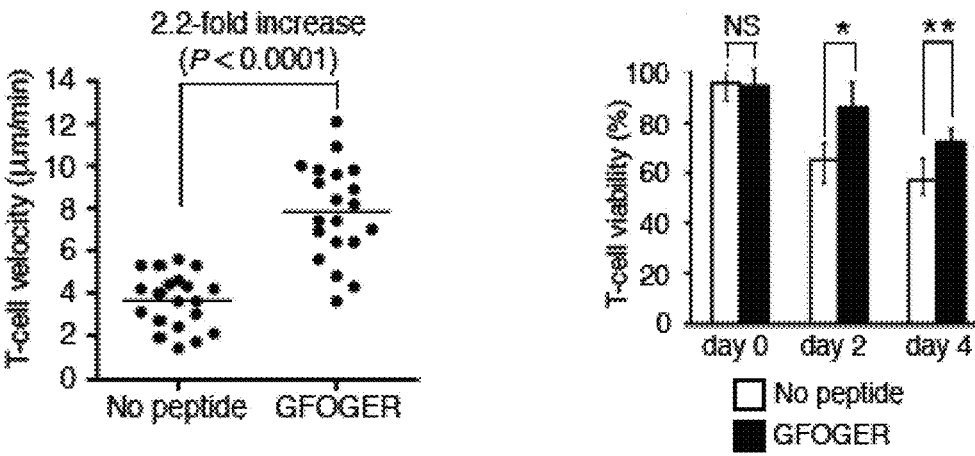
FIG. 6D.                                    FIG. 6E.

FIG. 8B     Functionalized with stimulatory microparticles...

Agonistic anti-CD3, CD28, CD137 antibodies (green)

PLGA microparticle (blue)

...or functionalized with stimulatory nanoparticles

Agonistic anti-CD3, CD28, CD137 antibodies conjugated to the lipid membrane

Lipid enveloped PLGA nanoparticle

Biopolymer scaffold BEFORE T-cell loading

Implanted T-cells infiltrate tumor resection bed and migrate into tumor-draining (axillary/inguinal) lymph nodes Time after scaffold implantation (days)

Scaffold implantation

T-cell-loaded scaffold

4T1 tumor resection cavity

T-cells embedded inside the scaffold

Scaffold implant

Tumor resection margin/bed

Scaffold-released tumor-reactive T-cells

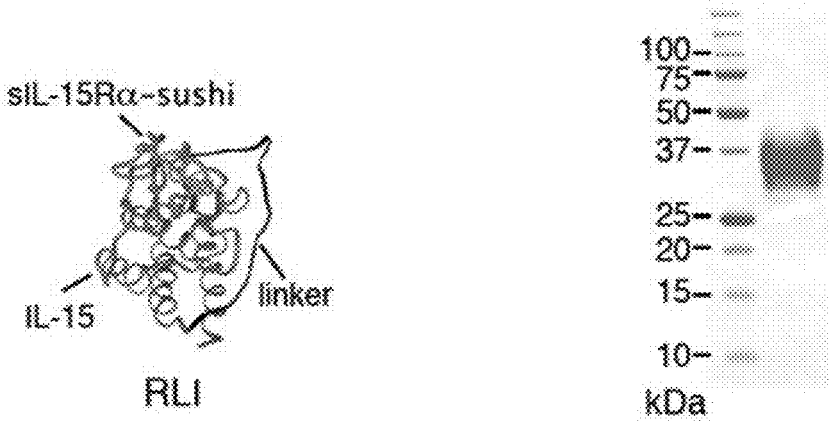
FIG. 10A.                              FIG. 10B.
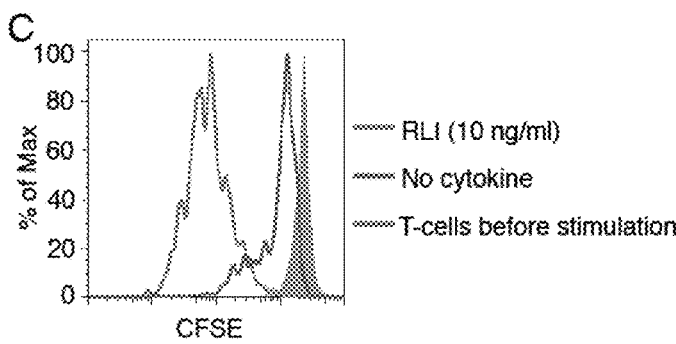
FIG. 10C.
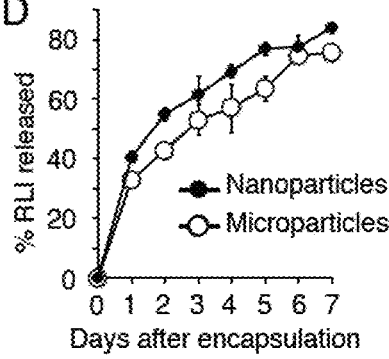
FIG. 10D.

No T cells (ms = 19 days)    ⎤ P = 0.21
intravenous (ms = 21 days)   ⎱ P = 0.03*
intracavitary (ms = 25 days) ⎱ P < 0.0001*
scaffold-delivered           ⎦

T-cell imaging

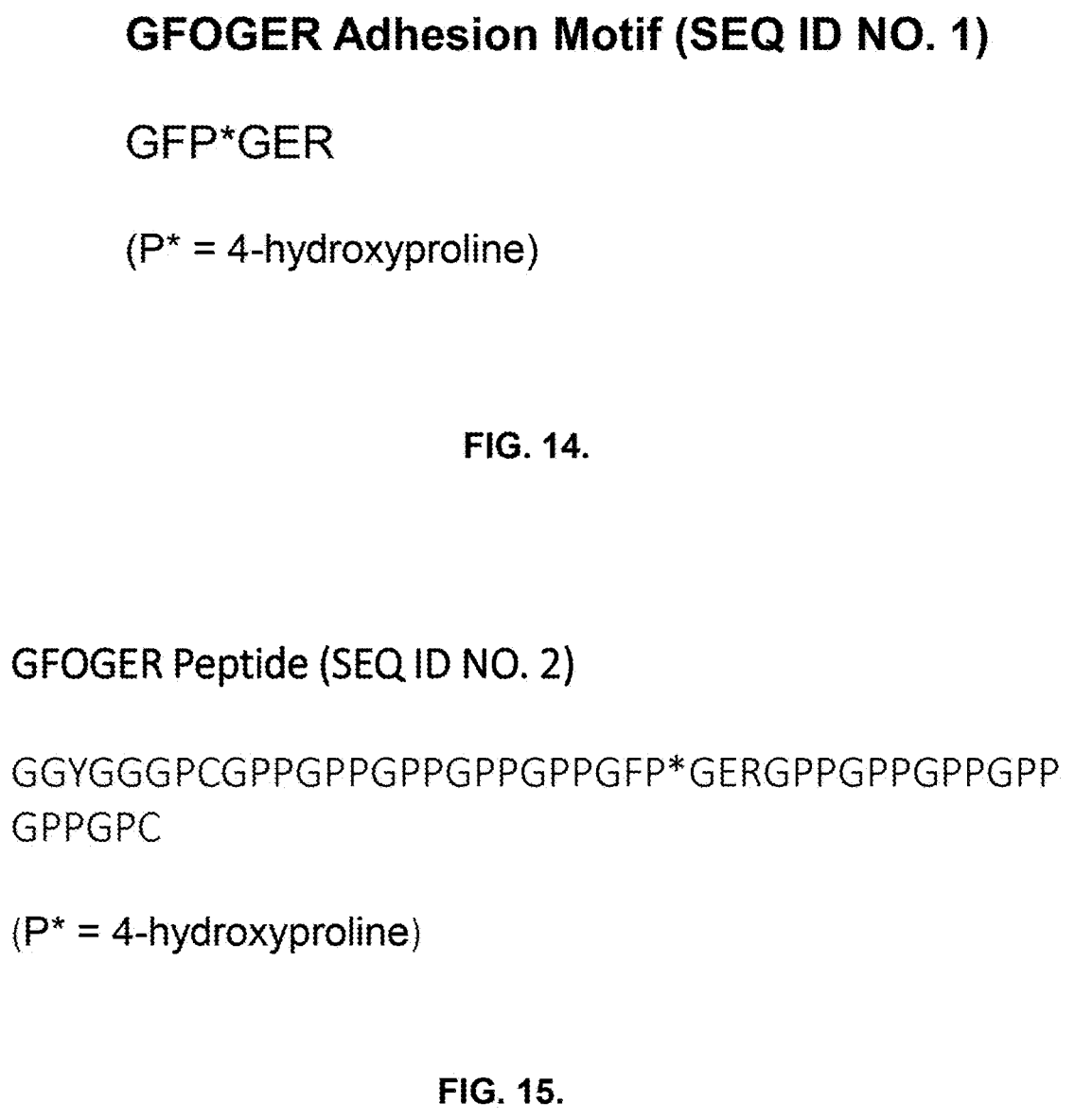

GFOGER Adhesion Motif (SEQ ID NO. 1)

GFP*GER (P* = 4-hydroxyproline)

FIG. 14.

GFOGER Peptide (SEQ ID NO. 2)

GGYGGGPCGPPGPPGPPGPPGPPGFP*GERGPPGPPGPPGPP
GPPGPC (P* = 4-hydroxyproline)

FIG. 15.

ICAM-1 Cell Adhesion Molecule (SEQ ID NO. 3)

MAPSSPRPALPALLVLLGALFPGPGNAQTSVSPSKVILPRGGSVLVTC
STSCDQPKLLGIETPLPKKELLLPGNNRKVYELSNVQEDSQPMCYSN
CPDGQSTAKTFLTVYWTPERVELAPLPSWQPVGKNLTLRCQVEGGAP
RANLTVVLLRGEKELKREPAVGEPAEVTTTVLVRRDHHGANFSCRTEL
DLRPQGLELFENTSAPYQLQTFVLPATPPQLVSPRVLEVDTQGTVVCS
LDGLFPVSEAQVHLALGDQRLNPTVTYGNDSFSAKASVSVTAEDEGT
QRLTCAVILGNQSQETLQTVTIYSFPAPNVILTKPEVSEGTEVTVKCEA
HPRAKVTLNGVPAQPLGPRAQLLLKATPEDNGRSFSCSATLEVAGQLI
HKNQTRELRVLYGPRLDERDCPGNWTWPENSQQTPMCQAWGNPLP
ELKCLKDGTFPLPIGESVTVTRDLEGTYLCRARSTQGEVTREVTVNVL
SPRYEIVIITVVAAAVIMGTAGLSTYLYNRQRKIKKYRLQQAQKGTPMK
PNTQATPP

FIG. 16.

FN-III$_{7-10}$ Fragment (SEQ ID NO. 4)

PLSPPTNLHLEANPDTGVLTVSWERSTTPDITGYRITTTPTNGQQGNSLEEVVHADQSSCT
FDNLSPGLEYNVSVYTVKDDKESVPISDTIIPAVPPPTDLRFTNIGPDTMRVTWAPPPSIDLT
NFLVRYSPVKNEEDVAELSISPSDNAVVLTNLLPGTEYVVSVSSVYEQHESTPLRGRQKTGL
DSPTGIDFSDITANSFTVHWIAPRATITGYRIRHHPEHFSGRPREDRVPHSRNSITLTNLTPG
TEYVVSIVALNGREESPLLIGQQSTVSDVPRDLEVVAATPTSLLISWDAPAVTVRYYRITYGE
TGGNSPVQEFTVPGSKSTATISGLKPGVDYTITVYAVTGRGDSPASSKPISINYRT

FIG. 17.

COMPOSITIONS AND METHODS FOR DELIVERY OF IMMUNE CELLS TO TREAT UN-RESECTABLE OR NON-RESECTED TUMOR CELLS AND TUMOR RELAPSE

CROSS REFERENCE TO RELATED APPLICATIONS

This application is a continuation of U.S. application Ser. No. 17/039,671, filed Sep. 30, 2020 which is a continuation of U.S. application Ser. No. 16/156,996, filed Oct. 10, 2018, now U.S. Pat. No. 10,806,756, which is a continuation of U.S. application Ser. No. 16/155,801, filed Oct. 9, 2018, now U.S. Pat. No. 10,702,551, which is a continuation of U.S. application Ser. No. 14/760,695, filed Jul. 13, 2015, which is a National Phase Application of International Application No. PCT/US2014/011526, filed Jan. 14, 2014, which claims priority to and the benefit of U.S. Provisional Application Nos. 61/900,922 filed Nov. 6, 2013 and 61/752,423 filed Jan. 14, 2013. The entire contents of each of these applications are incorporated by reference herein.

REFERENCE TO SEQUENCE LISTING

The Sequence Listing associated with this application is provided in text format in lieu of a paper copy and is hereby incorporated by reference into the specification. The name of the text file containing the Sequence Listing is 44699686_xml. The text file is 6611 bytes, was created on Dec. 6, 2023, and is being submitted electronically via Patent Center.

FIELD OF THE DISCLOSURE

The present disclosure provides compositions and methods for the delivery of immune cells to treat un-resectable or non-resected tumor cells and tumor relapse. The compositions comprise (i) a structure; (ii) lymphocytes, (iii) lymphocyte-adhesion moieties; and (iv) lymphocyte-activating moieties, and optionally an immune stimulant.

BACKGROUND OF THE DISCLOSURE

Some cancers, such as advanced pancreatic cancers, are un-resectable at the time of their discovery. Additionally, cancer relapse following surgery remains a major clinical problem and is frequently the ultimate cause of death. Relapse often occurs because tumors cannot be completely resected, as they invade vital organs and/or lack distinct borders. To eradicate residual tumor, transfusions of tumor-reactive lymphocytes, referred to as adoptive cell therapy (ACT), are currently being tested in cancer patients as one of the most promising treatment options. However, two major hurdles remain that seriously limit the use of ACT to prevent tumor relapse: infused lymphocytes inefficiently traffic to tumor, and even if a limited number of administered lymphocytes infiltrate tumor tissue, they poorly persist. Accordingly, although some patients benefit enormously from ACT, in most cases the tumor will ultimately grow back, with lethal consequences.

SUMMARY OF THE DISCLOSURE

The present disclosure provides compositions comprising (i) a structure; (ii) lymphocytes, (iii) lymphocyte-adhesion moieties; and (iv) lymphocyte-activating moieties, and optionally an immune stimulant. The compositions can be surgically implanted at a site of an un-resectable tumor or at a tumor resection site following the resection. Such compositions can act as active depots, releasing lymphocytes into the tumor area or resection bed to purge residual tumor cells. In some embodiments, at the same time, dispersed immune stimulants can activate the subject's immune system to destroy distant deposits of tumor cells. Supporting components of the compositions, including lymphocyte-activating moieties assist with lymphocyte multiplication and activation while lymphocyte-adhesion moieties assist with lymphocyte movement out of the composition into the tumor cell area. Thus, the compositions can provide a clinical device to provide surgeons with a more effective treatment option for tumors that currently cannot be resected or can only be managed by palliative surgery.

Treatment with the compositions and methods disclosed herein can save patients from complicated second or third surgeries, costly extended hospital stays, rounds of radiation or chemotherapy, and expensive palliative care.

Thus, disclosed herein is a composition comprising (i) a structure comprising an injectable polymer or scaffold comprising pores; (ii) lymphocytes disposed within the structure, (iii) at least one lymphocyte-adhesion moiety associated with the structure; and (iv) at least one lymphocyte-activating moiety associated with the structure.

In another embodiment, the lymphocytes are T-cells and/or natural killer cells. In another embodiment, the lymphocytes are CD8+ T-cells. In yet another embodiment, the composition comprises at least $7 \times 10^6$ lymphocytes.

In another embodiment, the lymphocyte-adhesion moiety comprises a collagen-mimetic peptide, a peptide that binds $\alpha_1\beta_1$ integrin, $\alpha_2\beta_1$ integrin, $\alpha_4\beta_1$ integrin, $\alpha_5\beta_1$ integrin, or lymphocyte function associated antigen (LFA-1), a GFO-GER (SEQ ID NO:1)_peptide, an ICAM-1 peptide, or a $FNIII_{10}$ peptide. In yet another embodiment, the lymphocyte-adhesion moiety comprises a peptide of SEQ ID NO:1, SEQ ID NO:2, SEQ ID NO:3, or SEQ ID NO:4.

In another embodiment, the lymphocyte-activating moieties are bound to or incorporated in one or more particles, wherein the particles are microparticles or nanoparticles. In another embodiment, the particles are microparticles with a diameter of 10-20 μm and the ratio of microparticles to lymphocytes within the composition is 0.5:1; 1:1; 5; 1 or 10; 1. In yet another embodiment, the particles are nanoparticles with a diameter of 100-150 nm and the ratio of nanoparticles to lymphocytes within the composition is 500:1; 1000:1 or 5000; 1. In another embodiment, the composition comprises $7 \times 10^6$ to $1 \times 10^{10}$ particles, In another embodiment, lymphocyte-activating moiety comprises antibodies specific for CD3, CD28, and/or CD137.

In another embodiment, the composition further comprises an immune stimulant. In yet another embodiment, the particles further comprise an immune stimulant. In another embodiment, the immune stimulant is a cytokine, an antibody, a small molecule, an siRNA, a plasmid DNA, and/or a vaccine adjuvant. In another embodiment, the cytokine is IL-2, IL-4, IL-10, IL-11, IL-12, IL-15, IL-18, TNFα, IFN-α, IFN-β, IFN-γ, or GM-CSF. In another embodiment, the immune stimulant is the interleukin-15 superagonist RLI. In yet another embodiment, the immune stimulant is a vaccine adjuvant such as CpG oligodeoxynucleotide or Poly(I:C).

In another embodiment, the structure is injectable.

In yet another embodiment, the lymphocyte-adhesion moieties and/or lymphocyte-activating moieties are associated with the structure in a bioactive coating on the scaffold. In another embodiment, the lymphocyte-activating moieties are associated with particles embedded in the pores of the scaffold. In yet another embodiment, the lymphocyte-activating moieties are associated with particles attached to the surface of the scaffold or are embedded in the scaffold.

In another embodiment, the scaffold is an alginate scaffold. In yet another embodiment, the scaffold is a polymeric calcium cross-linked alginate scaffold.

In yet another embodiment of the composition, the lymphocytes, lymphocyte-adhesion moieties, and lymphocyte-activating moieties are within the structure of the composition.

Also disclosed herein is a method of treating a tumor in a subject comprising implanting a composition of any one of Exemplary Embodiments 1-33 into a subject within a proximity to a tumor cell sufficient to lead to the destruction of the tumor cell in the subject, thereby treating the tumor.

Further disclosed herein is a method of reducing surgical treatment failure caused by metastatic relapse after resection of a primary tumor, comprising administering a composition of any one of Exemplary Embodiments 1-33 to a tumor resection bed of a subject thereby reducing surgical treatment failure caused by metastatic relapse after primary tumor resection.

In another embodiment, the implanting is within a tumor resection bed. In another embodiment, the implanting leads to the destruction of a tumor cell of an incompletely resected tumor or a tumor cell of a metastasized tumor.

In another embodiment, the destroyed tumor cell is a cell of an incompletely resected tumor. In yet another embodiment, the destroyed tumor cell is a cell of a metastasized tumor.

In another embodiment, the tumor cell is a seminoma cell, a melanoma cell, a teratoma cell, a neuroblastoma cell, a glioma cell, a rectal cancer cell, an endometrial cancer cell, a kidney cancer cell, an adrenal cancer cell, a thyroid cancer cell, a skin cancer cell, a brain cancer cell, a cervical cancer cell, an intestinal cancer cell, a liver cancer cell, a colon cancer cell, a stomach cancer cell, a head and neck cancer cell, a gastrointestinal cancer cell, a lymph node cancer cell, an esophageal cancer cell, a colorectal cancer cell, a pancreatic cancer cell, an ear, nose and throat (ENT) cancer cell, a breast cancer cell, a prostate cancer cell, a uterine cancer cell, an ovarian cancer cell, or a lung cancer cell. In yet another embodiment, the tumor cell is a glioblastoma cell, a pancreatic adenocarcinoma cell or an ovarian cancer cell.

BRIEF DESCRIPTION OF THE FIGURES

(FIG. 3B) Stimulatory microparticles trigger the expansion of loaded T-cells within the interior pore spaces of the scaffold. Tumor-reactive T-cells are released into the surrounding tissue to destroy residual tumor. Free tumor antigen is taken up by antigen presenting cells (APCs). (FIG. 3C) Immune stimulants released from the scaffold activate and mature APCs to prime and expand tumor antigen-specific lymphocytes in the host to destroy distant metastases throughout the body.

(FIG. 4A) Schematic of the 4T1 tumor vaccine (4T1-STIM). The surface expression of the costimulatory ligands B7.1 and 4-1BBL was confirmed by flow cytometry in (FIG. 4B). (FIG. 4C) Flow cytometric measurement of IFN-γ in lymphocytes harvested from immunized mice before (left panel) and after a seven day in vitro expansion (right panel) on irradiated 4T1-STIM monolayer. (FIG. 4D) $^{51}$Cr release assay of expanded CD8-purified lymphocytes targeting 4T1 tumor or B16F10 control tumor.

(FIG. 5A) Longitudinal bioluminescence imaging of Gau-luc-expressing 4T1 tumors. Bioluminescent tumor signal quantified per animal every two days over a period of 42 days. Representative images for day 12 (before and after tumor resection) and day 30 (tumor relapse) are shown in the upper panel. (FIG. 5B) Sequential bioluminescence imaging of adoptively transferred 4T1 tumor-reactive T-cells retrovirally transduced with CBR-luc. Representative images from a total of 5 mice/group imaged every two days are shown. T-cells were injected as bolus intravenously or into the resection bed.

FIGS. 6A-6E. Migration and sustained viability of T-cells inside alginate scaffolds coated with a collagen-mimetic peptide. (FIG. 6A) Reaction scheme of GFOGER (SEQ ID NO:1) peptide (in the FIGs. and experimental examples, SEQ ID NO: 2) coupling to alginate. (FIG. 6B) Fluorescence quantification of the DYLIGHT® 650-labelled GFOGER (SEQ ID NO:1) peptide in alginate scaffolds. Representative images of uncoated versus peptide-coupled alginate discs are shown on the right. (FIG. 6C) Photomicrograph of a T-cell loaded alginate scaffold. Time-lapse images of T-cells migrating through unmodified or GFOGER (SEQ ID NO:1) peptide functionalized alginate scaffolds. A 10-fold magnified image is shown in the inset to illustrate avid pore-to-pore migration of T-cells. Trajectories of individual T-cells tracked for two hours are shown in the lower panels. Time averaged velocities with and without GFOGER (SEQ ID NO: 1) peptide are graphed in (FIG. 6D). (FIG. 6E) Percentages of viable (Annexin-V/PI double-negative) T-cells following alginase enzyme digestion of scaffolds with and without GFOGER (SEQ ID NO: 1) peptide to recover T-cells.

(FIG. 7A) Schematic diagram of the in vitro assay to quantify the migration of tumor-reactive T-cells from an alginate scaffold into a tissue mimetic (3D fibrillar collagen gel). (FIG. 7B) Light microscope images of 4T1 tumor-reactive CD8+ T-cells that have migrated from GFOGER (SEQ ID NO:1) peptide-coated scaffolds into 3D collagen gels. Scale bar: 100 μm. (FIG. 7C) Quantification of T-cells in the alginate scaffold and in the collagen matrix. At indicated time points, T-cells were recovered from scaffolds and collagen gel by alginase or collagenase enzyme digestion, respectively. The number of viable T-cells was determined by Trypan Blue exclusion and graphed. (FIG. 7D) $^{51}$Cr release assay of T-cells recovered from collagen gel after 48 hours targeting 4T1 tumor or B16F10 control tumor. (FIG. 7E) ELISA analysis of IL-2 (at 24 hours), IFN-γ, and TNF-α (at 48 hours) secreted by recovered T-cells seeded on an irradiated 4T1 STIM tumor cell monolayer.

FIGS. 8A-8C. Stimulatory microparticles or nanoparticles integrated into the 3D pore structure of GFOGER (SEQ ID NO:1) peptide-coated alginate scaffolds. (FIG. 8A) Photomicrograph of lyophilized scaffold. (FIG. 8B) Light microscopy image of alginate scaffold with incorporated stimulatory (anti-CD3/CD28/CD137 antibody-coated) poly(lactic-co-glycolic acid) (PLGA) microparticles (black dots). A higher magnification confocal image of a single microparticle is shown in the right panel. (FIG. 8C) Confocal micrograph of alginate scaffold with integrated stimulatory lipid-enveloped nanoparticles. A cryo-transmission electron microscopy (TEM) image of lipid-coated PLGA nanoparticles is shown in the right panel.

(FIG. 9A) Photomicrograph of GFOGER (SEQ ID NO:1) peptide-coated alginate scaffold seeded with 4T1 tumor-reactive T-cells. The scaffold is being placed where a primary 4T1 tumor was just incompletely excised. FIG. 9B Sequential bioluminescence imaging of implanted T-cells. Cells were retrovirally transduced with clickbeetle red luciferase. Representative acquisitions from a total of four mice imaged every two days are shown. (FIG. 9C) Confocal image of tumor-reactive T-cells (labeled with CellTracker™ Green, Life Technologies) as they exit alginate scaffold (Alexa-647-labelled) to populate the tumor resection bed four days after implantation.

FIGS. 10A-10D. Functional recombinant IL-15-superagonist RLI can be produced in 293-F cells and efficiently encapsulated into PLGA particles. (FIG. 10A) Three-dimensional model of the RLI fusion protein (adjusted from Mortier, J Biol Chem, 281, 1612-1619 (2006)). (FIG. 10B) SDS polyacrylamide gel stained with Coomassie blue showing purified RLI protein (molecular weight: 34 kDa). (FIG. 10C) Carboxyfluorescein succinimidyl ester (CFSE) dilutions of 4T1 tumor-specific CD8+ T-cells after a 6-day coculture on irradiated 4T1 tumor monolayers with or without 10 ng/ml exogenous RLI. (FIG. 10D) In vitro release kinetics of RLI from PLGA micro- or nanoparticles in RPMI medium containing 10% FCS at 37° C. determined by ELISA. The RLI encapsulation efficiencies for micro and nanoparticles were 41% (±6%) and 37% (±8%), respectively.

(FIG. 11A) Image of prosurvival cytokine, stimulatory antibodies, mesoporous silica microparticle, and lipid envelope. (FIG. 11B) Graphs showing T-cell proliferation and T-cell migration into surrounding tissue for both plain scaffold (upper panels) and scaffold with microparticles (lower panels).

(FIG. 12A) Bioluminescent tumor signal quantified per animal at 0, 6, 14, and 18 days. Luciferase-tagged tumor cells were transplanted into the mammary gland, and ten days later, tumors were resected in a way such that ~1% residual diseased tissue remained. Four different treatment groups were studied (10 mice/group); no T cells (control mice left untreated after surgery), intravenous, intracacity, or scaffold delivered 4T1 tumor-reactive T-cells. (FIG. 12B) Bioluminescent tumor signal quantified per animal every six days over a period of 30 days. (FIG. 12C) Survival of animals following T-cell therapy illustrated by Kaplan-Meier curves. (FIG. 12D) Sequential bioluminescence imaging of adoptively transferred 4T1 tumor-reactive T-cell retrovirally transduced with luciferase. (FIG. 12E) Bioluminescent T-cell signal quantified per animal every two days over a period of 12 days. (FIG. 12F) Confocal image of tumor-reactive T-cell (labeled with CellTracker™ Green (Thermo Fischer Scientific, Inc.)) as they exit the scaffold (Alexa-647-labeled) to populate the tumor resection bed four days after implantation.

FIG. 14. Polypeptide sequence of the GFOGER (SEQ ID NO:1) peptide adhesion motif.

FIG. 15. Polypeptide sequence of the GFOGER (SEQ ID NO:1) peptide used in the Examples (SEQ ID NO. 2).

FIG. 16. Polypeptide sequence of the ICAM-1 cell adhesion molecule (SEQ ID NO. 3).

FIG. 17. Polypeptide sequence of the FN-III$_{7\text{-}10}$ fragment (SEQ ID NO. 4).

(FIG. 18A) Photomicrograph of a T-cell loaded alginate scaffold. Time-lapse images of T-cells migrating through unmodified or Collagen mimetic peptide (in the FIGs. and experimental examples the GFOGER (SEQ ID NO:1)-peptide SEQ ID NO: 2 is used) coated alginate scaffolds. Shown are trajectories of individual T-cells tracked for 30 minutes. (FIG. 18B) Graph showing mean displacements of T-cells during the 30 minute imaging interval. (FIG. 18C) Schematic diagram of the in vitro assay to quantify the migration of tumor-reactive T-cells from an alginate scaffold into a tissue mimetic (3D collagen gel). Light microscope images of tumor-reactive T-cells that have migrated from the scaffold into the 3D collagen gel are shown in the lower panel. (FIG. 18D) Quantification of T-cells in the alginate scaffold and in the collagen matrix. At indicated time points, T-cells were recovered from scaffolds and collagen gel by alginase or collagenase enzyme digestion, respectively. The number of viable T-cells was determined by Trypan Blue exclusion and graphed. (FIG. 18E) Light microscopy image of alginate scaffold with incorporated microspheres. Particles were created by coating porous silica microparticles with lipid bilayers that mimic cell membranes. The high pore volume and surface area of the silica core allow high-capacity encapsulation and sustained release of soluble biomolecules. The T-cell stimulant interleukin 15 superagonist, which is an interleukin 15 (IL-15)/IL-15Rα fusion protein that exhibits 50-fold greater potency than IL-15 alone was encapsulated. The lipid membrane used to envelop particles serves as a modular scaffold for the attachment of a variety of lymphocyte-stimulating ligands. Agonistic anti-CD3, anti-CD28, and anti-CD137 monoclonal antibodies were covalently coupled to the surface of microspheres containing IL-15/IL-15Rα. These prepared particles were then added to a GFOGER (SEQ ID NO:1) peptide-modified alginate solution before molding 3D scaffolds. (FIG. 18F) Quantification of T-cell egress from plain scaffolds, versus scaffolds carrying stimulatory microparticles. Using the in vitro assay from FIGS. 18C and 18D, the number of viable T-cells in the scaffold and the surrounding collagen gel at given time points was determined. (FIG. 18G) CFSE dilutions of T-cells embedded in plain versus microparticle-functionalized scaffolds were analyzed by flow cytometry 7 days after cell seeding.

DETAILED DESCRIPTION

Figure 1:
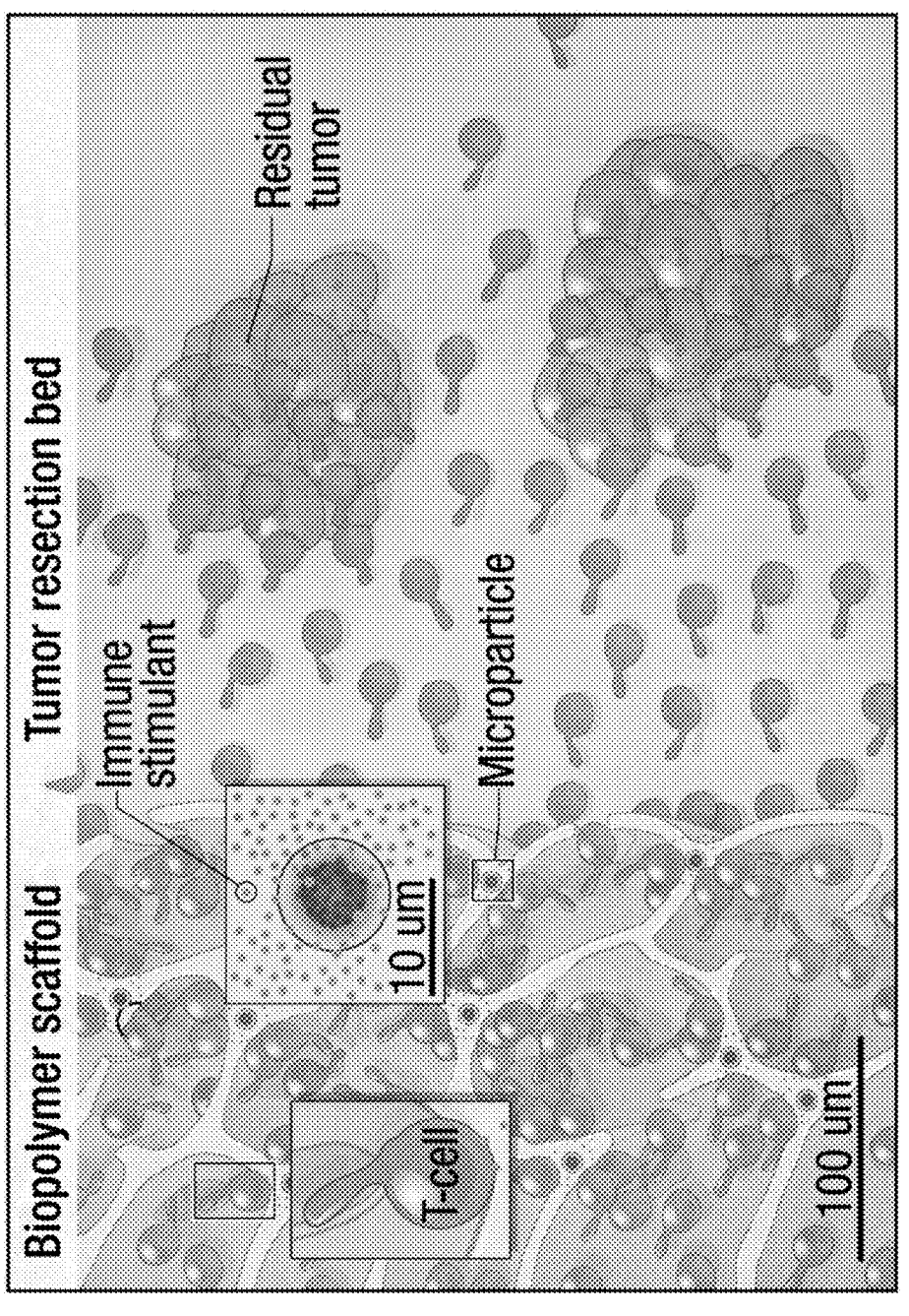
FIG. 1. Delivery of tumor-reactive lymphocytes.
Figure 2:
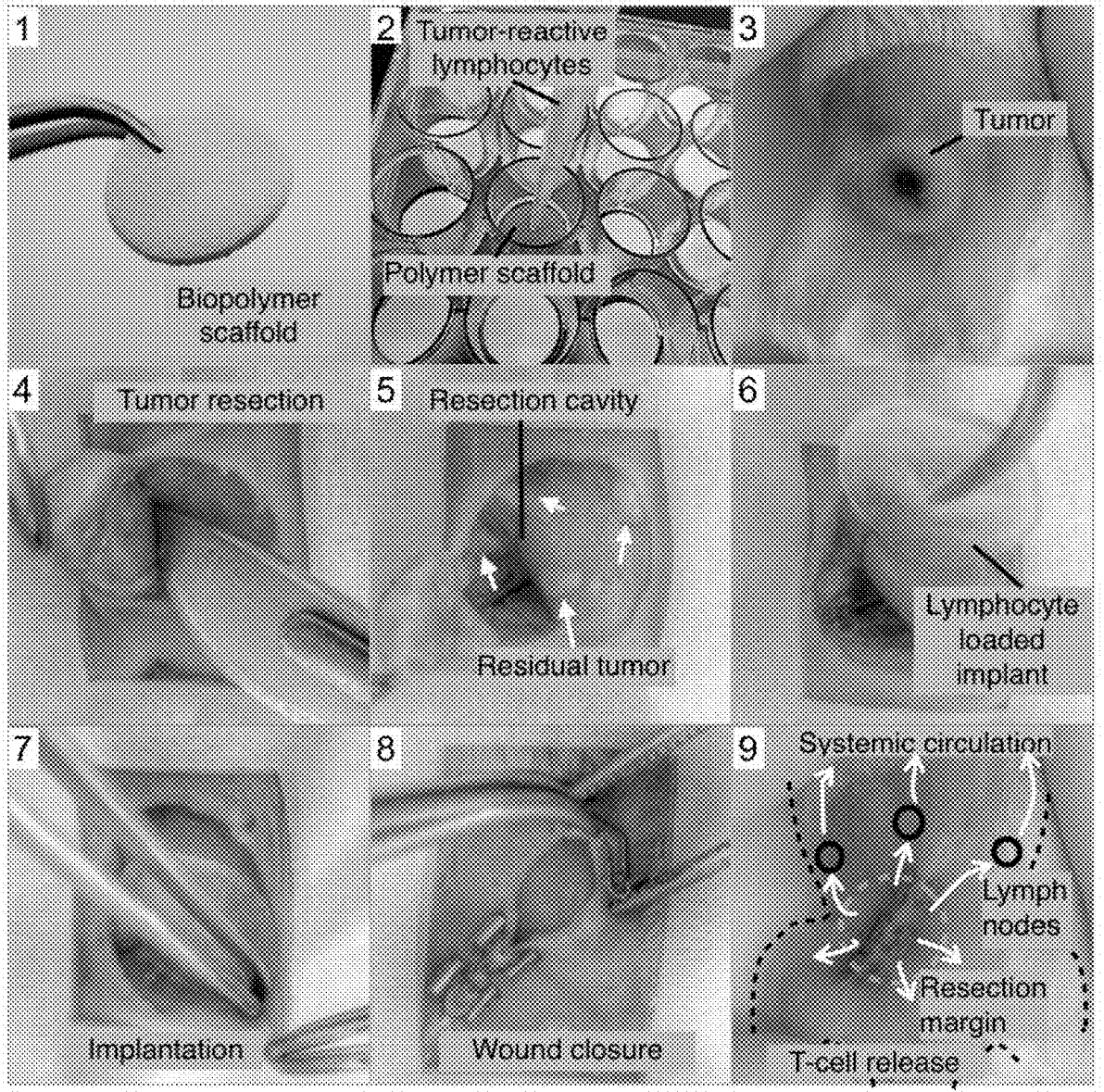
FIG. 2. Lymphocyte delivery approach using a composition disclosed herein. (1) biopolymer scaffold, (2) lymphocyte seeding, (3) mouse mammary tumor, (4) surgical resection, (5) resection cavity with residual tumor, (6, 7) implantation of implant harboring tumor-reactive lymphocytes, (8) wound closure, (9) controlled release of tumor-fighting lymphocytes into the resection cavity and tumor-draining lymph nodes.

A projected 1.5 million new patients will be diagnosed with solid tumors in the United States in 2013. Most of them will undergo surgery, based on the premise that a major resection leads to longer survival. Nonetheless, surgery is often considered a palliative venture with no hope of cure, as many tumors infiltrate vital organs or critical structures that cannot be resected. Adjuvant chemotherapy and radiation treatments can increase the duration of survival, but in most cases are not curative interventions. While monoclonal antibodies have significantly improved the outcome of patients undergoing surgery, most patients succumb to disease relapse. Hence, no adjuvant therapy is currently available that can reliably eradicate all microscopic residual disease following solid-tumor surgery.

An ideal anti-tumor immunotherapy should not only eradicate residual tumor cells quickly to prevent tumor relapse, but should also activate the patient's own immune system to induce systemic anti-tumor memory for control of metastatic tumors and long-term tumor resistance. In theory, cancer vaccines are capable of eliciting such anti-tumor activity, however in reality, residual tumors progress very rapidly and literally outpace the immune system. Conversely, tumor-reactive T-cells infused in ACT can lyse large tumor deposits immediately, yet the majority of transferred cells never reach their intended target or are rendered dysfunctional by the tumor microenvironment. Another limitation currently restricting the widespread use of ACT is the need to grow sufficient numbers of tumor-reactive cells in the laboratory ($10^{10}$-$10^{11}$ cells/patient). This is an extremely costly, laborious process performed in a few locations worldwide.

Disclosed herein are compositions and methods that can treat un-resectable tumors or non-resected tumor cells and therefore treat cancer, metastasis, and/or tumor relapse. The compositions include a structure, lymphocytes, lymphocyte-adhesion moieties and lymphocyte-activating moieties. Lymphocyte-adhesion moieties assist with lymphocyte exit from the structure following implantation at a treatment site. Lymphocyte-activating moieties support activation, multiplication and/or maintenance of the lymphocytes within the structure.

The structure can be an injectable structure or a scaffold with pores. In embodiments including a scaffold, the pores can provide a structure to embed tumor-targeting lymphocytes. In some embodiments, the scaffold is formed from a material having lymphocyte-adhesion moieties.

In other embodiments, lymphocyte-adhesion moieties can be provided as part of a bioactive coating that fully or partially coats the scaffold.

When a scaffold is used, lymphocyte-activating moieties can be a part of the scaffold itself, can be provided as part of a bioactive coating and/or can be provided on particles. The described particles can be micro- or nanoparticles and can be embedded in the pores of the scaffold, attached to the surface of the scaffold and/or be embedded within the scaffold itself. The composition may further comprise one or more immune stimulants.

The described compositions and methods provide surgeons with a powerful tool to effectively deliver and functionally support tumor-reactive lymphocytes to target un-resectable tumors and/or to purge healthy tissue and lymph nodes of residual tumor cells following a resection. The compositions sustain the viability of, stimulate the proliferation of, and/or amplify the anti-tumor activity of embedded lymphocytes. The compositions and methods also allow the controlled release of lymphocytes directly into the tumor or tumor bed following resection to treat cancer and/or to protect against disease metastasis and/or recurrence.

The described compositions obviate the need to grow billions of cells in the laboratory as all essential stimulatory lymphocyte-activating moieties for activation of embedded lymphocytes are incorporated into the structure of the composition itself. Thus, only a small number ($10^6$-$10^7$) of minimally cultured lymphocytes are needed to prepare the described compositions. Embedded lymphocytes then rapidly expand in situ within the structure and migrate out of the composition with the assistance of lymphocyte-adhesion moieties. Already at the treatment site, the lymphocytes immediately begin eliminating tumor cells including residual tumor cells in a resection bed. As used herein, the terms "resection bed" and "tumor resection bed" refer to the area immediately surrounding the previously resected tumor. The smaller number of required lymphocytes to effectuate the treatments allows many cancer centers, where even only rudimentary cell-processing facilities are available, to take advantage of the treatment benefits offered by the currently disclosed compositions and methods.

Figure 3A:
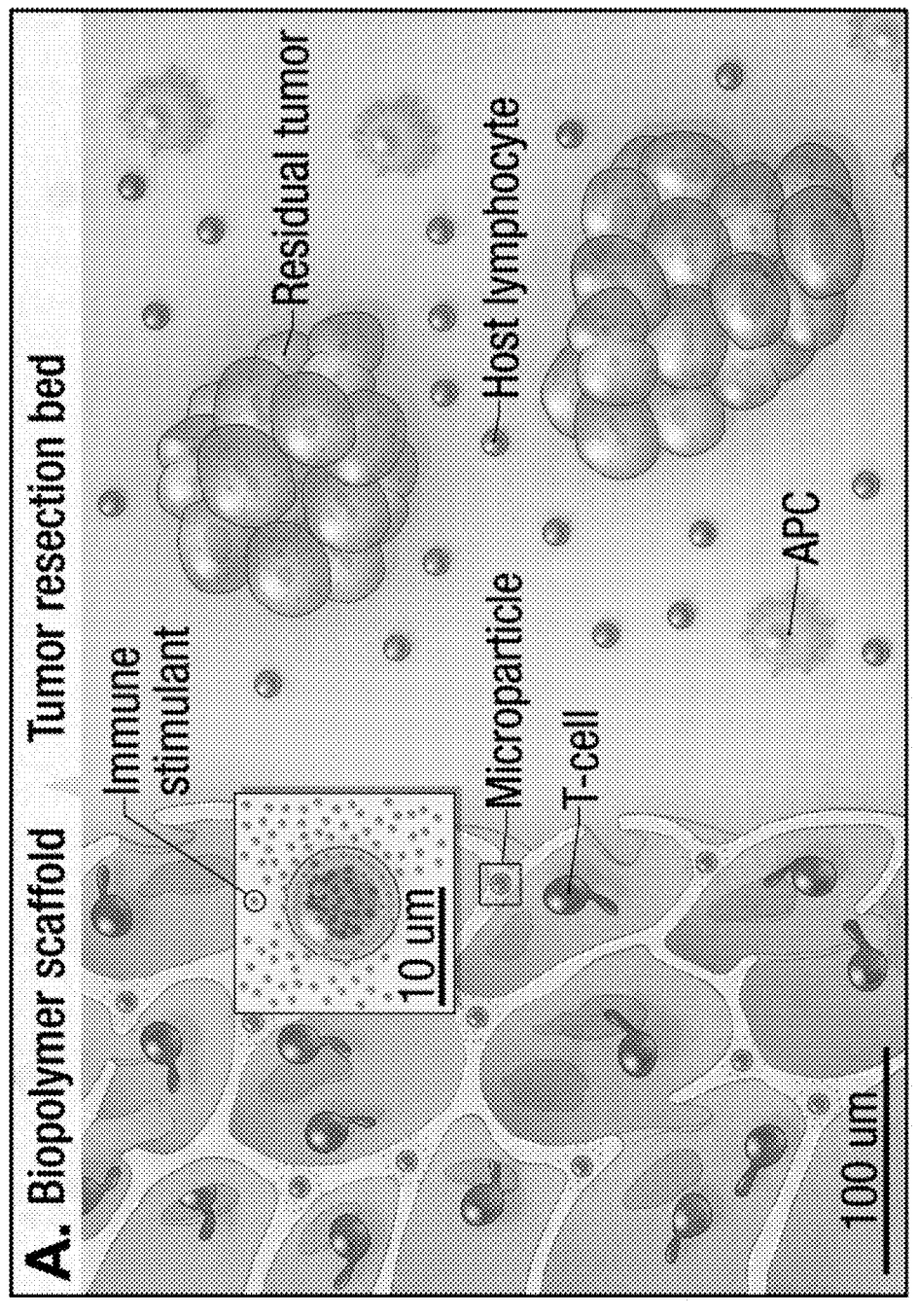
FIGS. 3A-3C. Rapid tumor cell clearance and systemic anti-tumor activity with a disclosed composition (FIG. 3A) Biopolymer scaffold loaded with tumor-reactive T-cells immediately after implantation onto tumor resection bed.
Figure 3B:
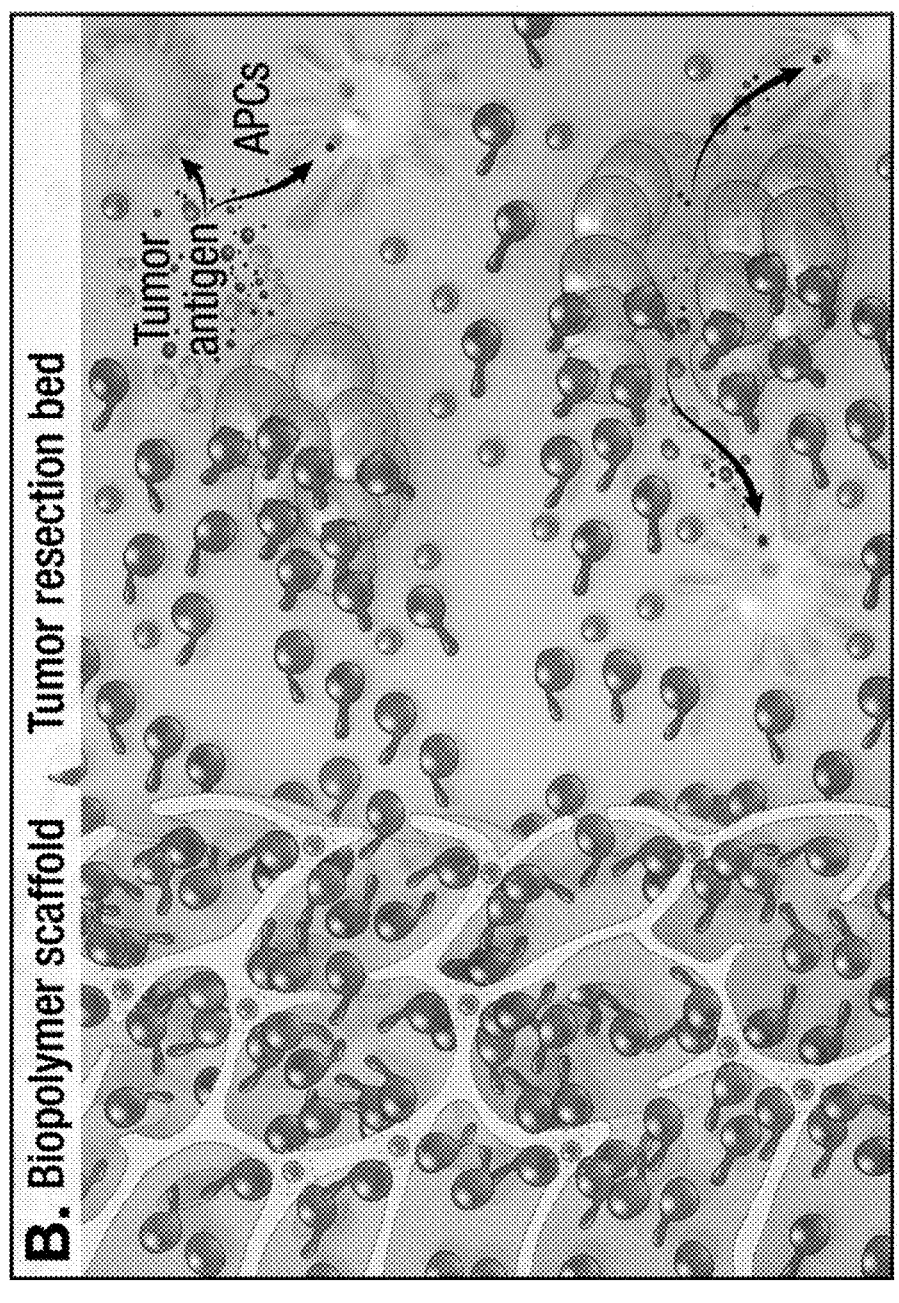
Figure 3C:
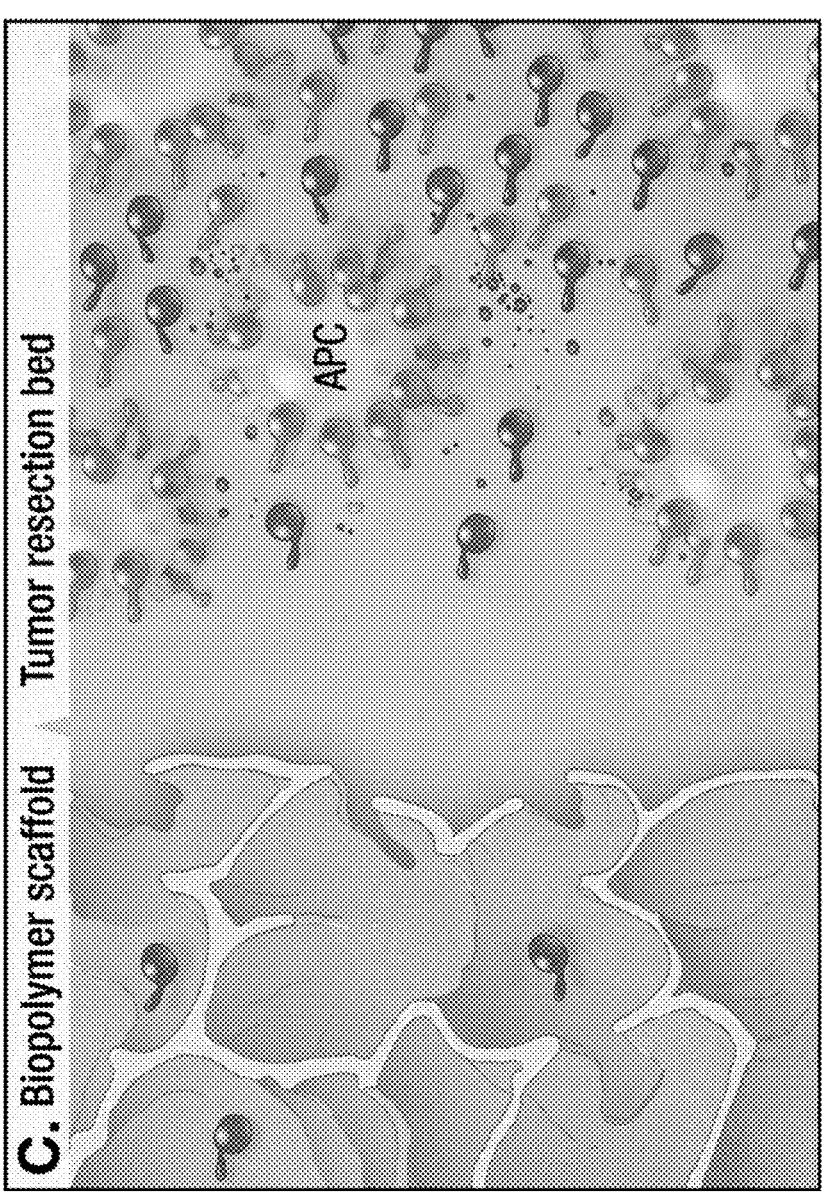

In particular embodiments, the compositions of the current disclosure can deliver tumor-reactive lymphocytes (FIG. 3A) along with immune stimulants at high local concentrations and over an extended period of time. Lymphocytes seeded within the composition exit the composition following implantation and disperse at high densities throughout a tumor resection bed and into draining lymph nodes to destroy remaining residual tumor cells following a resection (FIG. 3B). This step releases large amounts of tumor antigens from dying tumor cells into the tissue, which are subsequently taken up by antigen presenting cells (APCs). At this point, the compositions can play a second key role. By releasing a potent immune stimulant, they can activate APCs and tumor-reactive immune cells to mount a robust host anti-tumor immune response. This "second wave" of anti-tumor immunity is broader and involves multiple cell types (FIG. 3C) acting in synergy to eliminate remaining tumor cells. This described approach provides immediate efficacy by implantation of anti-tumor lymphocytes. At the same time, the composition is designed to turn the tumor site or tumor resection cavity into a "self" vaccine site using dying tumor cells directly as the source of antigen to launch an effective anti-tumor immune response in the host.

The described compositions also provide in vivo screening tools to (1) test which immune cell types, cell phenotypes or combinations of immune cells are most potent at destroying tumors, and (2) identify agents that boost their anti-tumor activity. The conventional approach currently used to answer these critical questions usually involves intravenous injection of the immune cells to be tested into tumor-bearing animals. However once infused, cells poorly traffic to the tumor and quickly change their phenotype, which prevents the determination of their intrinsic anti-tumor activity. Likewise, small molecules, cytokines or stimulatory antibodies are often rapidly cleared from the circulation following intravenous administration and poorly penetrate into solid tumors. This makes it extremely difficult to study their direct effects on immune cells in tumors. Within the disclosed compositions, any immune cell type can be embedded into the compositions along with a given therapeutic compound and, upon implantation, is directly exposed to tumor under clinically relevant in vivo conditions. This approach provides previously inaccessible knowledge about how immune cells collaborate and how drugs affect their function, which could ultimately speed up the transition of cell-based immunotherapies to the clinic.

Various components of the compositions and methods are now described in more detail.

Polymers

The structures of the compositions can be constructed from a variety of material including, without limitation, biocompatible polymers. Exemplary biocompatible polymers include, but not limited to, agar, agarose, alginate, alginate/calcium phosphate cement (CPC), beta-galactosidase (β-GAL), (1,2,3,4,6-pentaacetyl a-D-galactose), cellulose, chitin, chitosan, collagen, elastin, gelatin, hyaluronic acid collagen, hydroxyapatite, poly(3-hydroxybutyrate-co-3-hydroxy-hexanoate) (PHBHHx), poly(lactide), poly (caprolactone) (PCL), poly(lactide-co-glycolide) (PLG), polyethylene oxide (PEO), poly(lactic-co-glycolic acid) (PLGA), polypropylene oxide (PPO), poly(vinyl alcohol) (PVA), silk, soy protein, and soy protein isolate, alone or in combination with any other polymer composition, in any concentration and in any ratio. Blending different polymer types in different ratios using various grades can result in characteristics that borrow from each of the contributing polymers. Various terminal group chemistries can also be adopted.

When injectable structures are used, the polymers can be responsive to a changed environmental condition following implantation. Polymers with these characteristics are known to those of ordinary skill in the art. For example, in one embodiment, an injectable in situ gel-forming system is used. In one embodiment, the polymer formulation can gel in vivo in response to temperature change (thermal gelation), in response to pH change or in response to light. For example, polymers that gel in response to ultraviolet (UV) light can be used. In another embodiment, the polymer formulation can gel in vivo in response to ionic cross-linking. In another embodiment, the polymer formulation can gel in vivo in response to solvent exchange. In one embodiment, the gel used is thermoreversible, pH reversible, or light reversible. In another embodiment, the gel used is high-viscosity and shear-thinning. In additional gelling embodiments, the gel can be a gel formed from, without limitation, any polymer described herein.

In particular embodiments, alginate is used as a structure material, either separately or in combination with one or more other materials. Alginate is easily processed, water soluble, and non-immunogenic. Alginate is a biodegradable anionic polysaccharide with free hydroxyl groups that offer easy gelling. In alternative embodiments, the polymer may be a polyelectrolyte complex mixture (PEC) formed from a 1:1 solution of alginate and chitosan.

In one embodiment, a structure may formed from an alginate/calcium carbonate/glucono-delta-lactone mixture, such as 0.5-5% alginate, 0.5-15 g/L calcium carbonate, and 1-50 g/L gluconon-delta-lactone in a ratio of 2:1:1 (alginate:CaCO₃:GDL). Polymer structures may also include varying amounts of gelatin in combination with varying amounts of alginate. Depending on the materials and material ratios in mixture, the structures may optionally be cross-linked.

In particular embodiments, polymer solutions having varying amounts of polymer dissolved in an acidic solution can be used to form the structures disclosed herein. The concentration of the acid can be adjusted depending on the amount of polymer dissolved. In one aspect, the acidic solution is 1% (v/v) acetic acid. In one embodiment, the amount of polymer in solution is between about 0.5-5% (w/v) and any whole or partial increments therebetween. For example, the amount of polymer in solution (w/v) can be 0.5%, 1%, 1.5%, 2%, 2.5%, 3%, 3.5%, 4%, 4.5% or 5%. In one embodiment, the amount of polymer in solution is 2.4%

(w/v). In other various embodiments, the polymer is dissolved in at least one of water, acid, acetic acid, camphene, or camphene-naphthalene.

When gelatin is incorporated, the concentration of the acid can be adjusted depending on the amount of gelatin in combination with polymer (in one embodiment, alginate) that is dissolved. In one aspect, the acidic solution is 1% (v/v) acetic acid. In one embodiment, the amount of gelatin in solution is between about 1-10% (w/v) and any whole or partial increments therebetween. For example, the amount of alginate in solution (w/v) can be 1%, 2%, 3%, 4%, 5%, 6%, 7%, 8%, 9% or 10%. In one embodiment, the amount of alginate in solution is 5.5% (w/v). In another embodiment, the polymer solution includes a combination of 2.4% (w/v) alginate solution and a 5.5% (w/v) gelatin solution. In other various embodiments, the gelatin in combination with varying amounts of alginate is dissolved in at least one of water, acid, acetic acid, camphene, or camphene-naphthalene.

In another embodiment, alginate-based scaffolds can be formed as follows: a weight by volume (w/v) alginate solution in deionized (DI) water can be prepared and filtered with a 0.45 micrometer bottle filter to remove any particles and then frozen to −80° C. The frozen sample can be lyophilized in a 4.5 liter benchtop freeze dry system (Labconco, Kansas City, MO). The filtered lyophilized alginate can be reconstituted into solutions of various concentrations (0.1%-5%) with water or buffer.

Crosslinking can be performed with, without limitation, calcium chloride and/or calcium carbonate. Calcium carbonate is a slow crosslinker, with samples taking up to several hours to fully crosslink. To increase the speed of the reaction gluconodeltalactone (GDL) can be added. Calcium chloride is a fast crosslinker and the samples will fully gel in a few minutes. In one method, the addition of CaCl₂ to the alginate solution can occur prior to freezing. Other methods include use of a 5.5% (w/v) solution of calcium carbonate+GDL added to the alginate solution prior to initial freezing.

In particular embodiments, alginate solutions can be degassed in a speed mixer and poured slowly into casts to prevent bubbles from forming. When pipetting the polymer solutions into small molds, air bubble formation can be avoided by placing a micropipette on the open end of mold grooves and repeatedly flushing the entire canal system until the residual air is flushed out.

Freeze casting can be used to form the scaffolds disclosed herein. Various polymer solutions can be freeze cast into various sized casts as would be understood by those skilled in the art. The rate of cooling should be controlled as it affects the size and alignment of pores, as well as the formation of ridges. In one embodiment, the cooling rate can range between 0.1-100° C. per minute (m) and any whole or partial increments therebetween. In a preferred embodiment, the cooling rate can range between 1-10° C./m, and any whole or partial increments therebetween. For example, the cooling rate (° C./m) can be 0.1, 0.5, 1, 2, 3, 4, 5, 5.5, 6, 6.5, 7, 7.5, 8, 8.5, 9, 9.5, or 10.

Lymphocyte-Adhesion Moieties

The compositions disclosed herein include lymphocyte-adhesion moieties to promote lymphocyte mobility out of the implanted structures. Lymphocyte-adhesion moieties include, without limitation, cell-adhesion moieties such as cell-adhesion polypeptides that mimic the extracellular matrix (such as collagen). As used herein, "cell adhesion polypeptides" refer to compounds having at least two amino acids per molecule which are capable of binding via cell surface molecules, such as integrin. The cell adhesion polypeptides may be any of the proteins of the extracellular matrix which are known to play a role in cell adhesion, including fibronectin, vitronectin, laminin, elastin, fibrinogen, collagen types I, II, and V, as described in Boateng et al., Am. J. Physiol.—Cell Physio. 288:30-38 (2005), which is incorporated by reference herein for their teachings regarding the same. Additionally, the cell adhesion polypeptides may be any peptide derived from any of these proteins, including fragments or sequences containing the binding domains. Cell adhesion polypeptides include those having integrin-binding motifs, such as the ICAM-1 motif, and related peptides that are functional equivalents. Cell adhesion polypeptides may also be any of the peptides described in U.S. Patent Publication No. 20060067909 which is incorporated by reference herein for its teachings regarding the same.

In particular embodiments, the structures include compounds having lymphocyte-adhesion moieties, such as a ligand for $\alpha_1\beta_1$ integrin, a ligand for $\alpha_2\beta_1$ integrin, a ligand for $\alpha4\beta_1$ integrin, a ligand for $\alpha_5\beta_1$ integrin, a ligand for lymphocyte function-associated antigen (LFA-1), or combinations thereof. In certain embodiments the ligand interacts specifically with one integrin. In still other embodiments, the ligand is not a complete fibronectin molecule or is not a complete collagen molecule.

The lymphocyte-adhesion moiety can be a peptide, antibody, or a small organic molecule. A small organic molecule refers to a carbon-based molecule having a molecular weight of 500 daltons or less. The antibody or an integrin binding fragment thereof can be single chained, humanized, or chimeric. In certain embodiments, the lymphocyte-adhesion moiety can be a collagen-mimetic peptide, for example a stable triple-helical, collagen-mimetic peptide that contains the GFOGER (SEQ ID NO:1) adhesion motif from type I collagen that is recognized by the $\alpha_2\beta_1$ integrin. This peptide adopts a stable triple-helical conformation similar to the native structure of type I collagen. An exemplary collagen-mimetic peptide has the following amino acid sequence GGYGGGPC(GPP)$_5$GFP*GER(GPP)$_5$GPC (SEQ ID NO: 2). In one embodiment, the GFOGER (SEQ ID NO:1) peptide comprises, consists, or consists essentially of SEQ ID NO:2.

Another embodiment provides ICAM-1 as a lymphocyte-adhesion moiety. ICAM-1 is an Ig-like cell adhesion molecule that binds integrins promoting cell-cell adhesion and is a ligand for lymphocyte function-associated (LFA) antigens. ICAM-1 is found primarily on monocytes and endothelial cells, and is widely inducible, or upregulated, on many cells including T-cells, B-cells, thymocytes, dendritic cells, endothelial cells, fibroblasts, keratinocytes, chondrocytes, and epithelial cells. This protein has a co-stimulatory effect upon cytotoxic T-cell interaction, and is utilized in a number of intercellular binding interactions. In one embodiment, ICAM-1 comprises, consists, or consists essentially of SEQ ID NO:3.

Another embodiment provides FNIII$_{7-10}$ as a lymphocyte-adhesion moiety. FNIII$_{7-10}$ is a fibronectin fragment spanning the 7-10th type III repeats of fibronectin. The sequence of fibronectin is known in the art. In one embodiment, FNIII$_{7-10}$ comprises, consists or consists essentially of SEQ ID NO:4.

Effective variants of the sequences disclosed herein can also be used. Variants include peptides having one or more conservative amino acid substitutions. As used herein, a "conservative substitution" involves a substitution of one amino acid for another found in one of the following conservative substitutions groups: Group 1: Alanine (Ala), Glycine (Gly), Serine (Ser), Threonine (Thr); Group 2:

Aspartic acid (Asp), Glutamic acid (Glu); Group 3: Asparagine (Asn), Glutamine (Gln); Group 4: Arginine (Arg), Lysine (Lys), Histidine (His); Group 5: Isoleucine (lie), Leucine (Leu), Methionine (Met), Valine (Val); and Group 6: Phenylalanine (Phe), Tyrosine (Tyr), Tryptophan (Trp).

Additionally, amino acids can be grouped into conservative substitution groups by similar function or chemical structure or composition (e.g., acidic, basic, aliphatic, aromatic, sulfur-containing). For example, an aliphatic grouping may include, for purposes of substitution, Gly, Ala, Val, Leu, and lie. Other groups containing amino acids that are considered conservative substitutions for one another include: sulfur-containing: Met and Cysteine (Cys); acidic: Asp, Glu, Asn, and Gln; small aliphatic, nonpolar or slightly polar residues: Ala, Ser, Thr, Pro, and Gly; polar, negatively charged residues and their amides: Asp, Asn, Glu, and Gln; polar, positively charged residues: His, Arg, and Lys; large aliphatic, nonpolar residues: Met, Leu, lie, Val, and Cys; and large aromatic residues: Phe, Tyr, and Trp. Additional information is found in Creighton (1984) Proteins, W.H. Freeman and Company which is incorporated by reference for its teachings regarding the same.

Variants also include sequences with at least 70% sequence identity, 80% sequence identity, 85% sequence, 90% sequence identity, 95% sequence identity, 96% sequence identity, 97% sequence identity, 98% sequence identity, or 99% sequence identity to SEQ ID NO:1; SEQ ID NO:2; SEQ ID NO:3; and SEQ ID NO:4.

"% identity" refers to a relationship between two or more protein sequences, as determined by comparing the sequences. In the art, "identity" also means the degree of sequence relatedness between proteins as determined by the match between strings of such sequences. "Identity" (often referred to as "similarity") can be readily calculated by known methods, including (but not limited to) those described in: Computational Molecular Biology (Lesk, A. M., ed.) Oxford University Press, NY (1988); Biocomputing: Informatics and Genome Projects (Smith, D. W., ed.) Academic Press, NY (1994); Computer Analysis of Sequence Data, Part I (Griffin, A. M., and Griffin, H. G., eds.) Humana Press, NJ (1994); Sequence Analysis in Molecular Biology (Von Heijne, G., ed.) Academic Press (1987); and Sequence Analysis Primer (Gribskov, M. and Devereux, J., eds.) Oxford University Press, NY (1992), each incorporated by reference herein for its teachings regarding the same. Preferred methods to determine identity are designed to give the best match between the sequences tested. Methods to determine identity and similarity are codified in publicly available computer programs. Sequence alignments and percent identity calculations may be performed using the Megalign program of the Lasergene bioinformatics computing suite (DNASTAR®, Inc., Madison, WI). Multiple alignment of the sequences can also be performed using the Clustal method of alignment (Higgins and Sharp CABIOS, 5, 151-153 (1989), incorporated by reference herein for its teaching regarding the same) with default parameters (GAP PENALTY=10, GAP LENGTH PENALTY=10). Relevant programs also include the GCG suite of programs (Wisconsin Package Version 9.0, Genetics Computer Group (GCG), Madison, WI); BLASTP, BLASTN, BLASTX (Altschul, et al., J. Mol. Biol. 215:403-410 (1990), incorporated by reference herein for its teaching regarding the same); DNASTAR®; and the FASTA program incorporating the Smith-Waterman algorithm (Pearson, Comput. Methods Genome Res., [Proc. Int. Symp.] (1994), Meeting Date 1992, 111-20. Editor(s): Suhai, Sandor. Publisher: Plenum, New York, N.Y. incorporated by reference herein for its teaching regarding the same). Within the context of this disclosure it will be understood that where sequence analysis software is used for analysis, the results of the analysis are based on the "default values" of the program referenced. As used herein "default values" will mean any set of values or parameters which originally load with the software when first initialized.

Within certain embodiments, the lymphocyte-adhesion moieties may be incorporated into the backbone of a polymer chain. For example, a polymer can be created containing YIGSR in the backbone of a polymer as described in Jun et al., J. Biomaterials Sci., Polymer Ed. 15(1), 73-94 (2004), which is incorporated by reference herein for its teachings regarding the same. One of skill in the art could incorporate other cell adhesion polypeptides into the backbone of alginate or other polymers.

In another embodiment, the lymphocyte-adhesion moieties may be grafted onto a polymer. In particular embodiments, the lymphocyte-adhesion moieties are polypeptides that may be grafted onto polymers using various methods known in the art. In one method, polymers having side branches containing reactive functional groups such as epoxide, halide, amine, alcohol, sulfonate, azido, anhydride, or carboxylic acid moieties can be covalently linked to the amine terminus of the polypeptides via the reactive side branches using conventional coupling techniques such as carbodiimide reactions. For example, RGD (Arg-Gly-Asp)-containing peptides have been grafted onto the backbone of polymers as described in Lin, et al., J. Biomedical Materials Res, 28(3), 329-42 (1994) which is incorporated by reference herein for its teachings regarding the same. In another example, RGD-containing peptides have been grafted onto the side branches of polyethylene glycol based polymers, as described in Hansson, et al., Biomaterials, 26, 861-872 (2005).

When scaffolds are used as a structure, the scaffold can comprise fibrin scaffolds, collagen scaffolds or fibrin and/or collagen scaffold blends (blended with, for example, alginate). Certain embodiments do not require bioactive coatings to support lymphocyte mobility. Similarly, injectable forms of the structures do not require bioactive coatings.

Scaffolds can also be coated with a bioactive coating comprising a lymphocyte-activating moiety. In particular embodiments, the scaffold is at least partially coated with a bioactive coating comprising a lymphocyte-adhesion moiety. The bioactive coating can be applied onto the surface of the scaffold in various ways, including the use of coating methods that are known in the art. For example, the bioactive coating may be sprayed onto the scaffold by a conventional electrostatic spraying process, resulting in charged droplets being deposited onto the surface of the composition As the coating fluid dries, the bioactive compound, for example, a polypeptide, remains adhered to the surface of the composition by inter-molecular bonding with the side-chain groups on the polypeptides. The deposited polypeptide may form a monolayer on the surface of the scaffolding.

In particular embodiments, the bioactive coating may be bonded to the surface of a scaffold by any type of chemical or physical bonding means, including covalent, polar, ionic, coordinate, metallic, electrostatic, or intermolecular dipolar (including Van der Waals) bonds.

In one embodiment, the surface of the scaffold is coated with GFOGER (SEQ ID NO:1) peptide. As an example, the purified GFOGER (SEQ ID NO:1) peptide could be stored as a trifluoroacetic acid (TFA) salt and reconstituted to 10 mg/mL in 0.1% TFA and 0.01% sodium azide and stored at 4° C. prior to use. After the scaffolds are rinsed with ethanol to remove contaminants, cleaned in fresh ethanol, rinsed in ddH$_2$O, they can be soaked in phosphate buffered saline (PBS). The GFOGER (SEQ ID NO:1) peptide can then be absorbed onto the scaffolds passively by incubating the scaffolds in a solution of GFOGER (SEQ ID NO:1) peptide in PBS. Prior to implantation, scaffolds could be rinsed in PBS to remove unbound GFOGER (SEQ ID NO:1) peptides.

In preparation of an alginate composition, an alginate/calcium carbonate/glucono-delta-lactone mixture can be prepared by stirring, with concentrations ranging from 0.5-5 wt % alginate, 0.5-15 g/L calcium carbonate, and 1-50 g/L glucono-delta-lactone in a volume ratio of 2:1:1 (alginate:CaCO$_3$:GDL) as a "pre-gelling" process. In particular embodiments, the resulting mixture can be freeze cast (directionally frozen) at a constant cooling rate (0.1°/min-10°/min) until solid and lyophilized until dry. The dried compositions can be crosslinked in 0.1-2.5 wt. % calcium chloride for 5-30 minutes and washed in HEPES buffered saline prior to any further use of the scaffold. For placement of a bioactive coating, surfaces of the compositions can be coated in polylysine or polyornithine (0.1-1.0 mg/ml for 3-10 minutes) followed by coating in a GFOGER (SEQ ID NO:1) peptide (10 µg/ml-250 µg/ml for 30 minutes-24 hours).

In preparation of a alginate-chitosan composition, an alginate-chitosan polyelectrolyte complex (PEC) mixture can be prepared by sonicating or homogenizing on ice in a range of 1:1 to 1:9 solutions (both ways) of alginate (prepared in water) and chitosan (prepared in 1% acetic acid) and total polymer content ranging from 0.5%-5%. The pH of the resulting mixture can be adjusted with NaOH up to 10.0. In particular embodiments, the alginate-chitosan PEC mixture can be freeze cast at a constant cooling rate (0.1°/min-10°/min) until solid and lyophilized until dry. Dried compositions can be crosslinked in 0.1-2.5% calcium chloride for 5-30 minutes and washed in PBS prior to any further use of the composition. For bioactive coating, scaffolds can be coated in polylysine or polyornithine (0.5 mg/ml for 6 minutes) followed by coating in a GFOGER (SEQ ID NO:1) peptide (10 µg/ml-250 µg/ml for 30 minutes-24 hours).

In particular embodiments, GFOGER (SEQ ID NO:1)_ peptides are immobilized onto alginate using aqueous carbodiimide chemistry.

Bioactive coatings can additionally include other components to alter the surface of the scaffold, for example polylysine, polyornitine, or other glycoproteins.

Lymphocyte-Activating Moieties

Lymphocyte-activating moieties include any compound that activates a lymphocyte and can be incorporated in or attached to the structures disclosed herein. As used herein, activation of a lymphocyte refers to the state of a lymphocyte that has been sufficiently stimulated to induce detectable cellular proliferation, cytokine production, or effector function such as tumor targeting and/or killing. If the lymphocyte is a T-cell, activation also results in expression of cell surface markers particular to the T-cell type. Exemplary lymphoctye-activating moieties include CD3, CD27, CD28, CD80, CD86, 4-1BB, CD137, OX40, CD30, CD40, LFA-1, CD2, CD7, LIGHT, NKG2C, B7-H3, and CD83 ligands or antibodies, CD1d, recombinant CD1d molecules preloaded with α-galactosyl ceramide and/or recombinant major histocompatibility complex (MHC) molecules loaded with defined tumor antigens or peptides to selectively expand particular lymphocyte types embedded within a scaffold.

Lymphocyte-activating moieties can be found within injectable forms of the structures or embedded within the pores of the scaffolds, attached to the surface of the scaffolds, and/or embedded within the scaffolds themselves. As discussed further below, lymphocyte-activating moieties can also be associated with particles.

Immune Stimulants

In particular embodiments, immune stimulants can be included within the compositions. In certain embodiments, the immune stimulant is a cytokine, an antibody, a small molecule, an siRNA, a plasmid DNA, and/or a vaccine adjuvant.

Exemplary cytokines include, without limitation, IL-2, IL-7, IL-12, IL-15, IL-18, IL-21, TNFα, IFN-α, IFN-β, IFN-γ, or GM-CSF. In another embodiment the immune stimulant may be a cytokine composition comprising combinations of cytokines, such as IL-2, IL-12 or IL-15 in combination with IFN-α, IFN-β or IFN-γ, or GM-CSF, or any effective combination thereof, or any other effective combination of cytokines. The above-identified cytokines stimulate TH1 responses, but cytokines that stimulate $T_H2$ responses may also be used, such as IL-4, IL-10, IL-11, or any effective combination thereof. Also, combinations of cytokines that stimulate TH1 responses along with cytokines that stimulate $T_H2$ responses may be used.

Exemplary antibodies include, without limitation, anti-PD1, anti-PDL1, anti-CTLA-4, anti-TIM3, agonistic anti-CD40, agonistic anti-4-1BB, and/or bispecific antibodies (e.g., BITE-antibodies: anti-CD3/anti-tumor antigen). Exemplary small molecule drugs include, without limitation, TGF-beta inhibitors, SHP-inhibitors, STAT-3 inhibitors, and/or STAT-5 inhibitors. Any siRNA capable of down-regulating immune-suppressive signals or oncogenic pathways (such as kras) can be used whereas any plasmid DNA (such as minicircle DNA) encoding immune-stimulatory proteins can be used. Exemplary vaccine adjuvants, include, without limitation, any kind of Toll-like receptor ligand or combinations thereof (e.g. CpG, Poly(I:C), α-galactoceramide, MPLA, cyclic dinucleotides, VTX-2337 (novel TLR8 agonist developed by VentiRx), and/or inhibitors of heat-shock protein 90 (Hsp90), such as 17-DMAG (17-dimethylaminoethylamino-17-demethoxygeldanamycin).

Immune stimulants derived from the molecules noted in the preceding paragraphs can also be used. For example, RLI is an IL-15-IL-15 receptor-α fusion protein that exhibits 50-fold greater potency than IL-15 alone. IL-15 impacts the anti-tumor immune response at multiple points. It can differentiate monocytes into stimulatory antigen presenting cells; promote the effector functions and proliferation of tumor-reactive T-cells; and recruit and activate NK cells.

Immune stimulants can be found within injectable forms of the structures or embedded within the pores of the scaffolds, attached to the surface of the scaffolds and/or embedded within the scaffolds themselves. As discussed further below, immune stimulants can also be associated with particles.

Release of the immune stimulants from particles can be modified by incorporation of surfactants, detergents, complexing agents, internal phase viscosity enhancers, surface active molecules, co-solvents, chelators, stabilizers, derivatives of cellulose, polysorbates, PVA or sucrose. Salts and buffers can also be used to alter release characteristics.

Particles

In particular embodiments, particles can be included as means to deliver/present lymphocyte-activating moieties to lymphocytes because they can mimic physiological antigen presenting cells. Another advantage of particles is that they are highly modular and can be customized without affecting the chemical properties of the structure itself.

In particular embodiments, lymphocyte-activating moieties and/or immune stimulants are provided in association with particles. Particles can be included within injectable structures and/or within scaffolds. The particles can be formed from any biocompatible polymer including, without limitation, agar, agarose, alginate, alginate/CPC, β-GAL, (1,2,3,4,6-pentaacetyl α-D-galactose), cellulose, chitin, chitosan, collagen, elastin, gelatin, hyaluronic acid collagen, hydroxyapatite, PHBHHx, poly(lactide), PCL, PLG, PEO, PLGA, PPO, PVA, silk, soy protein, and soy protein isolate, alone or in combination with any other polymer composition, in any concentration and in any ratio. Blending different polymer types in different ratios using various grades can result in characteristics that borrow from each of the contributing polymers. Various terminal group chemistries can also be adopted.

In particular embodiments, the particles can be microparticles or nanoparticles. Microparticles can have a diameter of 10-20 μm while nanoparticles have a diameter of 100-150 nm.

Particles may be formed according to any method known to those of ordinary skill in the art. Common methods include, without limitation, spray-drying or emulsion.

In one embodiment, an organic phase of PLGA polymer and dioleoylphosphocholine (DOPC), dioleoylphosphoglycerol (DOPG) and malemimide-phycoerythin (PE) lipids are emulsified in water, leading to self-assembled lipid coatings surrounding each particle.

Particles may also be formed using a Buchi-190 Mini Spray wherein 1-2% polymer can be spray dried and collected in a dry container. The particles can be stirred in 0.4% sodium hydroxide in ethanol solution for 15 minutes to 1 hour before washing in PBS. The particles can be coated in 0.1-1% alginate solution for 5-20 minutes before washing in water, freezing, and lyophilization until dry. For covalent crosslinking, the particles can be stirred in a 0.001%-1% genipin solution prepared in PBS, or 0.001-25% glutaraldehyde solution for 0-48 hours. Crosslinking is stopped by stirring the particles in a 10% glycine (prepared in PBS) solution for 30 minutes. The particles can also be coated in 0.1-1% alginate solution for 5-20 minutes, or alginate solution followed by 0.1-1% polyethylene glycol solution for 5-20 minutes before washing in water, freezing, and lyophilizing until dry.

In another embodiment, alginate particles can be crosslinked as follows. Alginate particles (collected dry or collected in calcium chloride) can be suspended in ethanol. Epichlorohydrin (1-25% v/v) can be added to the particle mixture in ethanol. The mixture can be sonicated or homogenized on ice while adding 1M-6M sodium hydroxide. The mixture can then be stirred at room temperature for 6-24 hours and the reaction can be stopped by adjusting the pH to 7 with 1M hydrochloric acid. The crosslinked particle can be washed in ethanol in decreasing concentrations (e.g., 75%, 50%, 25%), followed by washing in water three times. Alternate covalent crosslinking can be performed by suspending the particles in methanol containing 1-25% glutaraldehyde and 0.05-5% hydrochloric acid, stirring for 0-48 hours. Remaining calcium chloride can be removed by stirring microcapsules in 55 mM sodium citrate for 10 minutes, followed by washing in water. Particles can also be coated here in A) 0.1-1% chitosan solution (prepared in 1% acetic acid) for 5-20 minutes, B) the solution of (A) followed by 0.1-1% alginate solution for 5-20 minutes; and/or C) the solution of (A) followed by 0.1-1% polyethylene glycol solution for 5-20 minutes. The additional crosslinking/coating steps are followed by washing in water, freezing, and lyophilizing until dry.

Lymphocyte-activating moieties can be incorporated on the surface of the particles by soaking (either from a dry state or pre-hydrated in PBS) in the desired lymphocyte-activating moiety solution (with or without stabilizers such as trehalose). In particular embodiments, concentrations and timing can range from 1 µg/ml to 1 g/ml for 15 minutes to 24 hours before rinsing with PBS.

In one embodiment, the lymphocyte-activating moieties are antibodies that are mildly reduced with dithiothreitol (DTT) and covalently coupled to maleimide on the surface of the particles.

In one embodiment, to incorporate the particles into compositions, the lymphocyte-activating moiety-surface coated particles can be stirred into the polymer mixture prior to freeze casting. In one embodiment, the prepared particles are added dropwise to a 2% aqueous GFOGER (SEQ ID NO:1)-peptide modified alginate solution before cross-linking alginate with calcium chloride and molding three-dimensional scaffolds by freeze drying. This process yields compositions with $7\times10^6$ antibody-coated PLGA microparticles that are homogenously dispersed within the scaffold's pore network.

In an additional example of forming particles, lipid stock solutions can be prepared in chloroform. DOPC, DSPE-PEG (2000) maleimide, cholesterol and 18:1 PEG(2000) PE can be combined in a scintillation vial to attain a DOPC:DSPE-PEG(2000) maleimide:cholesterol:PEG(2000) with a PE mass ratio of 55:5:30:10 and 2.5 mg total lipid. Chloroform can be evaporated and residual solvent removed.

A suspension of spherical silica gel can be prepared in PBS. The suspension can be combined with an immune stimulant. The suspension can be gently agitated and diluted. The entire suspension can be added to a batch of lipid film. The mixture can be vortexed. The particles can be centrifuged and the supernatant can be removed. The pellet can be washed and redispersed.

The hinge-region disulfide bonds of anti-CD3, CD28, and CD137 can be selectively reduced as described by Kwong et al, Biomaterials 32, 5134 (2011) which is incorporated by reference herein for its teachings regarding the same. After removal of the reducing agent, the mildly-reduced antibodies can be added to the maleimide-functionalized particles. The mixture can be vortexed briefly and the resulting antibody-labeled particles can be centrifuged and supernatant removed. The pellet can then be washed.

Lymphocytes

The structures of the compositions disclosed herein include embedded lymphocytes. Any type of lymphocyte capable of targeting and killing tumor cells, targeting tumor cells for killing by other cell types, or otherwise mediating tumor cell killing can be used. The lymphocytes are autologous to the individual for whom the composition is administered.

Lymphocytes include T-cells, B cells and natural killer (NK) cells. The current disclosure focuses on the use of embedded T-cells, but other types of lymphocytes may be used as well, alone or in combination.

Several different subsets of T-cells have been discovered, each with a distinct function. T-cells include helper cells (CD4+ T-cells) and cytotoxic T-cells (CTLs, CD8+ T-cells) which comprise cytolytic T-cells.

T helper cells assist other white blood cells in immunologic processes, including maturation of B cells into plasma cells and activation of cytotoxic T-cells and macrophages, among other functions. These cells are also known as CD4+ T-cells because they express the CD4 protein on their surface. Helper T-cells become activated when they are presented with peptide antigens by MHC class II molecules that are expressed on the surface of antigen presenting cells (APCs). Once activated, they divide rapidly and secrete small proteins called cytokines that regulate or assist in the active immune response.

Cytotoxic T-cells destroy virally infected cells and tumor cells, and are also implicated in transplant rejection. These cells are also known as CD8+ T-cells because they express the CD8 glycoprotein at their surface. These cells recognize their targets by binding to antigen associated with MHC class I, which is present on the surface of nearly every cell of the body.

A majority of T-cells have a T-cell receptor (TCR) existing as a complex of several proteins. The actual TCR is composed of two separate peptide chains, which are produced from the independent T-cell receptor alpha and beta (TCRα and TCRβ) genes and are called α- and β-TCR chains. Gamma-delta (γΔ) T-cells represent a small subset of T-cells that possess a distinct TCR on their surface. However, in γΔ T-cells, the TCR is made up of one γ-chain and one Δ-chain. This group of T-cells is much less common (2% of total T-cells) than the αβ T-cells.

"Central memory" T-cells (or "$T_{CM}$"), as used herein, refers to an antigen experienced CTL that expresses CD62L or CCR-7 and CD45RO on the surface thereof, and does not express or has decreased expression of CD45RA as compared to naive cells. In embodiments, central memory cells are positive for expression of CD62L, CCR7, CD2S, CD127, CD45RO, and CD95, and have decreased expression of CD54RA as compared to naive cells.

"Effector memory" T-cell (or "$T_{EM}$"), as used herein, refers to an antigen experienced T-cell that does not express or has decreased expression of CD62L on the surface thereof as compared to central memory cells, and does not express or has decreased expression of CD45RA as compared to a naive cell. In embodiments, effector memory cells are negative for expression of CD62L and CCR7, compared to naive cells or central memory cells, and have variable expression of CD28 and CD45RA.

"Naive" T-cells, as used herein, refers to a non-antigen experienced T lymphocyte that expresses CD62L and CD45RA, and does not express CD45RO as compared to central or effector memory cells. In some embodiments, naive CD8+T lymphocytes are characterized by the expression of phenotypic markers of naive T-cells including CD62L, CCR7, CD28, CD127, and CD45RA.

"Effector" or "TE" T-cells, as used herein, refers to a antigen experienced cytotoxic T lymphocyte cells that do not express or have decreased expression of CD62L, CCR7, CD28, and are positive for granzyme B and perforin as compared to central memory or naive T-cells.

Each of the lymphocytes types described herein can be embedded in the compositions disclosed herein. In particular embodiments, the primary lymphocyte cell type will be CTL. CTLs can be included at 50% or more of the embedded lymphocyte population, 55% or more of the embedded lymphocyte population, 60% or more of the embedded lymphocyte population, 65% or more of the embedded lymphocyte population, 70% or more of the embedded lymphocyte population, 75% or more of the embedded lymphocyte population, 80% or more of the embedded lymphocyte population, 85% or more of the embedded lymphocyte population, 90% or more of the embedded lymphocyte population, 95% or more of the embedded lymphocyte population, or 100% the embedded lymphocyte population.

Various combinations of lymphocytes can also be used in the compositions disclosed herein. In one embodiment, the composition includes a mixture of CD8+ cells, NK cells, invariant NKT cells (iNKT cells), Th17 CD4+ cells and/or B cells. In another embodiment, the compositions include a mixture of CD8+ cells and NK cells. In another embodiment, the mixture of CD8+ cells and NK cells is a 50:50 mix. In another embodiment, the compositions include a mixture of CD8+ cells and iNKT cells. In another embodiment, the mixture of CD8+ cells and iNKT cells is a 50:50 mix. All other possible combinations of the disclosed cell types can also be used within the compositions disclosed herein.

In particular embodiments, the lymphocytes can be isolated and expanded from resected tumor. In another embodiment, subjects can be vaccinated with a tumor antigen (e.g., against Her2) and vaccine-induced T-cell populations can be expanded and embedded into the composition.

Lymphocytes within the compositions can be non-genetically modified or genetically-modified or can be provided in a combination of non-genetically-modified and genetically-modified forms. Genetic modifications can be made to enhance growth, survival, immune function and/or tumor cell targeting. Examples of genetic modifications include those allowing expression of a chimeric antigen receptor (CAR), a αβ T-cell receptor (or modification thereof), and/or pro-inflammatory cytokines. CAR modification and/or αβ T-cell receptor modifications allow the modified lymphocytes to specifically target cell types.

In one aspect, modified lymphocytes can have improved tumor recognition, trigger increased native T-cell proliferation and/or cytokine production. Different potential CAR nucleic acid constructs that encode different ligand binding domains, different spacer region lengths, different intracellular binding domains and/or different transmembrane domains, can be tested in vivo (in an animal model) and/or in vitro to identify CARs with improved function over non-genetically modified lymphocytes and/or other CARs and in particular embodiments, using the compositions disclosed herein as an in vivo screening tool.

Exemplary CARs express ligand binding domains targeting, without limitation, mesothelin, Her2, WT-1 and/or EGRF. An exemplary T-cell receptor modification targets melanoma-associated antigen (MAGE) A3 TCR.

In some embodiments it may be desired to introduce functional genes into the lymphocytes to allow for negative selection in vivo as described by, for example, Lupton et al., Mol. and Cell Biol., 11:6 (1991); and Riddell et al., Human Gene Therapy 3:319-338 (1992); see also the publications PCT/US91/08442 and PCT/US94/05601 by Lupton et. al. describing the use of bifunctional selectable fusion genes derived from fusing a dominant positive selectable marker with a negative selectable marker and which are incorporated by reference herein for all they disclose regarding selectable genes. This can be carried out in accordance with known techniques (see, e.g., U.S. Pat. No. 6,040,177 at columns 14-17) or variations thereof that will be apparent to those skilled in the art based upon the present disclosure. For example, it is contemplated that overexpression of a stimulatory factor (for example, a lymphokine or a cytokine) may be toxic to the treated subject. Therefore, it is within the scope of the disclosure to include gene segments that cause the cells of the disclosure to be susceptible to negative selection in vivo. By "negative selection" is meant that the infused cell can be eliminated as a result of a change in the in vivo condition of the individual. The negative selectable phenotype may result from the insertion of a gene that confers sensitivity to an administered agent, for example, a compound. Negative selectable genes are known in the art, and include, inter alia the following: the Herpes simplex virus type I thymidine kinase (HSV-1 TK) gene, which confers ganciclovir sensitivity; the cellular hypoxanthine phosphribosyltransferase (HPRT) gene, the cellular adenine phosphoribosyltransferase (APRT) gene, and bacterial cytosine deaminase.

Desired genes can be introduced into the lymphocytes prior to embedding in a composition disclosed herein. Such introduction can be carried out by any method known in the art, including but not limited to transfection, electroporation, microinjection, lipofection, calcium phosphate mediated transfection, infection with a viral or bacteriophage vector containing the gene sequences, cell fusion, chromosome-mediated gene transfer, microcell-mediated gene transfer, sheroplast fusion, etc. Numerous techniques are known in the art for the introduction of foreign genes into cells (see e.g., Loeffler and Behr, Meth. Enzymol, 217, 599-618 (1993); Cohen et al., Meth. Enzymol, 217, 618-644 (1993); Cline, Pharmac. Ther, 29, 69-92 (1985)) and may be used in accordance with the present disclosure, provided that the necessary developmental and physiological functions of the lymphocytes are not disrupted. In one embodiment, the technique provides for the stable transfer of the gene to the cell, so that the gene is expressible by the cell and preferably heritable and expressible by its cell progeny. In other embodiments, the technique provides for transient expression of the gene within a cell.

Methods commonly known in the art of recombinant DNA technology which can be used to genetically modify the lymphocytes are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY, both of which are incorporated by reference herein for their relevant teachings.

In particular embodiments, lymphocytes will be embedded within the compositions at or near the time of composition implantation in a subject, for example within 48 hours of implantation, within 36 hours of implantation, within 24 hours of implantation, within 12 hours of implantation, within 6 hours of implantation, within 3 hours of implantation, within 1 hour of implantation or within 30 minutes of implantation. Generally, lymphocyte loading into pre-molded scaffolds will occur within 30 minutes of implantation whereas the loading will more often occur closer (i.e., within 5 minutes; within 2 minutes, within 1 minute or within 30 seconds) to the actual implantation time when injectable forms of the compositions are used.

The lymphocytes can be fresh lymphocytes or can be previously cryo-preserved lymphocytes. If previously-cryo-preserved lymphocytes are used, they should be thawed quickly (e.g., in a water bath maintained at 37°-41° C.) and chilled immediately upon thawing. It may be desirable to further treat the lymphocytes in order to prevent cellular clumping upon thawing. To prevent clumping, various procedures can be used, including but not limited to, the addition before and/or after freezing of DNase, low molecular weight dextran and citrate, hydroxyethyl starch, etc. Where necessary due to potential cytotoxicities, cryoprotective agents should be removed. After removal of cryoprotective agents, when necessary, cell count and/or viability testing can be performed.

A variety of methods to embed the lymphocytes into structures disclosed herein can be used ("embedding" is also referred to as "seeding"). For example, passive (static) seeding can be used. In one embodiment, lymphocytes are resuspended in cell culture medium (e.g., RPMI). This cell suspension is then added dropwise on top of a lyophilized scaffold. In another embodiment, where static seeding is used, a lymphocyte suspension is seeded onto a structure and afterwards incubated for a certain time in the absence of agitation before being exposed to dynamic culture conditions, for example into a spinner flask that is slowly agitated. In another embodiment, dynamic seeding can be used. For dynamic seeding the structure and the lymphocyte suspension can be placed together in, e.g., a container and the container is then incubated with gentle agitation for a certain time allowing the lymphocytes to embed themselves within the structure. In additional embodiments, rotational systems (including centrifuges) and/or vacuum systems can be used. In additional embodiments, sheet-based lymphocyte seeding, electrostatic lymphocyte seeding, magnetic lymphocyte seeding, filtration lymphocyte seeding, and/or oscillating perfusion lymphocyte seeding can be used. Various combinations, such as, and without limitation, rotational vacuum seeding can also be used. The use of various biological hydrogels is also appropriate. For discussions of the various seeding options, see Li et al., Biotechnol. Prog, 17, 935-944 (2001); Wendt et al., Biotechnology and Bioengineering, 84, 205-214 (2003); Yang, et al., J. Biomed. Mater. Res, 55, 379-386 (2001); and Sittinger et al., Int. J. Artif. Organs, 20, 57 (1997) each of which is incorporated by reference herein for its relevant teachings regarding the same.

Methods of Use

The compositions described herein can be placed in the vicinity of un-resecatable tumor and/or non-resected tumor cells to have an anti-tumor effect in a subject. As used herein, the terms "subject" or "individual" typically refer to a mammal, such as a human, but can also be another mammal such as, but not limited to, dogs, cats, rabbits, cows, horses, etc. A "tumor" is a swelling or lesion formed by an abnormal growth of cells (called neoplastic cells or tumor cells). A "tumor cell" is an abnormal cell that divides by a rapid, uncontrolled cellular proliferation and continues to divide after the stimuli that initiated the new division cease. Tumors show partial or complete lack of structural organization and functional coordination with the normal tissue, and usually form a distinct mass of tissue, which may be either benign, pre-malignant or malignant.

As used herein, an anti-tumor effect refers to a biological effect, which can be manifested by a decrease in tumor volume, a decrease in the number of tumor cells, a decrease in the number of metastases, an increase in life expectancy, or a decrease of various physiological symptoms associated with the cancerous condition. An anti-tumor effect can also be manifested by a decrease in recurrence or an increase in the time before recurrence. Accordingly, the compositions disclosed herein can be used to treat a variety of cancers, can prevent or significantly delay metastasis, and/or can prevent or significantly delay relapse.

Cancer (medical term: malignant neoplasm) refers to a class of diseases in which a group of cells display uncontrolled growth (division beyond the normal limits), invasion (intrusion on and destruction of adjacent tissues), and sometimes metastasis. "Metastasis" refers to the spread of cancer cells from their original site of proliferation to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor, i.e. a secondary tumor or metastatic tumor, at the target site depends on angiogenesis. Tumor metastasis often occurs even after the removal of the primary tumor because tumor cells or components may remain and develop metastatic potential.

Cancers that can be treated with the anti-tumor effects of the compositions and methods disclosed herein include, without limitation, seminomas, melanomas, teratomas, neuroblastomas, gliomas, rectal cancer, endometrial cancer, kidney cancer, adrenal cancer, thyroid cancer, skin cancer, cancer of the brain, cervical cancer, intestinal cancer, liver cancer, colon cancer, stomach cancer, head and neck cancer, gastrointestinal cancer, lymph node cancer, esophagus cancer, colorectal cancer, pancreas cancer, ear, nose and throat (ENT) cancer, breast cancer, prostate cancer, cancer of the uterus, ovarian cancer, lung cancer, and metastases thereof.

Without limiting the scope of the compositions and methods disclosed herein, the following cancer types are noted:

Brain tumor (Glioblastoma): An estimated 10,000 new cases/year in the U.S. are seen. Currently no curative therapy is available. Gliobastoma shows very infiltrative growth and cannot be resected completely. 90% of tumors relapse within a 2 cm margin from the originally resected tumor. Biomaterial wafers loaded with chemotherapy are United States Food and Drug Administration (FDA)-approved (GLIADEL®, MGI Pharma.) for glioblastoma. However, due to insufficient tissue penetration, biomaterial implant delivered chemotherapy is mostly ineffective. In contrast, tumor-reactive lymphocytes deployed from the compositions disclosed herein can actively migrate to affected tissue, seeking out and destroying residual tumor cells.

Pancreatic adenocarcinoma: An estimated 43,920 new cases of pancreatic cancer were expected to occur in the U.S. in 2012. Only 20% will have resectable disease at the time of diagnosis (80% of patients do not undergo surgery as their tumor is too advanced at the time of diagnosis). Even surgery is considered a palliative venture with a 5-year survival rate of only 20%. Local recurrence is usually attributed to the difficulty of achieving microscopically negative surgical margins. Beyond the current composition's primary application to eradicate residual disease following surgical tumor resection, the compositions could also provide pancreatic tumor patients with inoperable disease (~80% of patients) with a highly effective treatment option. In this embodiment, compositions are implanted directly onto un-resectable established pancreatic adenocarcinomas.

Ovarian cancer: An estimated 22,000 new cases in 2012 in the U.S. were seen. Despite multimodality therapy with surgery and chemotherapy, most ovarian cancer patients have a poor prognosis (15,500 estimated deaths/year in U.S.). Ovarian cancer primarily disseminates within the peritoneal cavity. Adoptive T-cell therapy in ovarian cancer patients is currently being investigated at several centers. However, to date clinical results have been disappointing due to a poor survival of infused T-cells and a failure to combat immunosuppressive factors released by tumor cells to render T-cells dysfunctional. Multiple compositions embedded with tumor-reactive lymphocytes could be implanted laparoscopically into the peritoneal cavity of ovarian cancer patients, where they release tumor-reactive lymphocytes and immune stimulants over an extended time period.

As will be understood by one of ordinary skill in the art, the compositions are implanted in close proximity to un-resectable tumor cells and/or in tumor resection beds following resection. The compositions can be available in a number of different sizes and shapes and can be shape-conformable to fit the particular needs of individual subjects. In particular embodiments, the compositions are injected using ultrasound guidance in close proximity to (or in physical contact with) un-resected or non-resected tumor cells. Depending on the stage, size or severity of a tumor, compositions may be provided with different therapeutic strengths. Therapeutic strength can be manipulated by altering the size of the composition, volume of the composition, the number of lymphocytes embedded within a composition, the number of lymphocyte-activating moieties within a composition, the presence or amount of immune stimulants within the composition, etc. Each of these parameters can be assessed and determined by a treating physician.

For the purposes of the present disclosure, the term "proximity" refers to a distance within 10 cm, within 9 cm, within 8 cm, within 7 cm, within 6 cm, within 5 cm, within 4 cm, within 3 cm, within 2 cm, within 1 cm, within 0.9 cm, within 0.8 cm, within 0.7 cm, within 0.6 cm, within 0.5 cm, within 0.4 cm, within 0.3 cm, within 0.2 cm, or within 0.1 cm of an un-resectable tumor, un-resectable tumor cells, and/or a tumor resection bed.

It is also understood by one of ordinary skill in the art that the compositions can be implanted only once, at the time of resection or at a first treatment time in an individual with an un-resectable tumor. Additionally, the compositions can be implanted a plurality of times to provide ongoing therapy over months or years. Such treatment regimens can be determined by a treating physician.

As used herein, the term "surgical treatment failure" refers to relapse of cancer in a subject who had previously undergone tumor resection. Surgical treatment failure may include metastatic relapse.

EXAMPLES

The Examples below are included to demonstrate particular embodiments of the disclosure. Those of ordinary skill in the art should recognize in light of the present disclosure that many changes can be made to the specific embodiments disclosed herein and still obtain a like or similar result without departing from the spirit and scope of the disclosure.

Figures 4A, 4B, 4C, 4D:
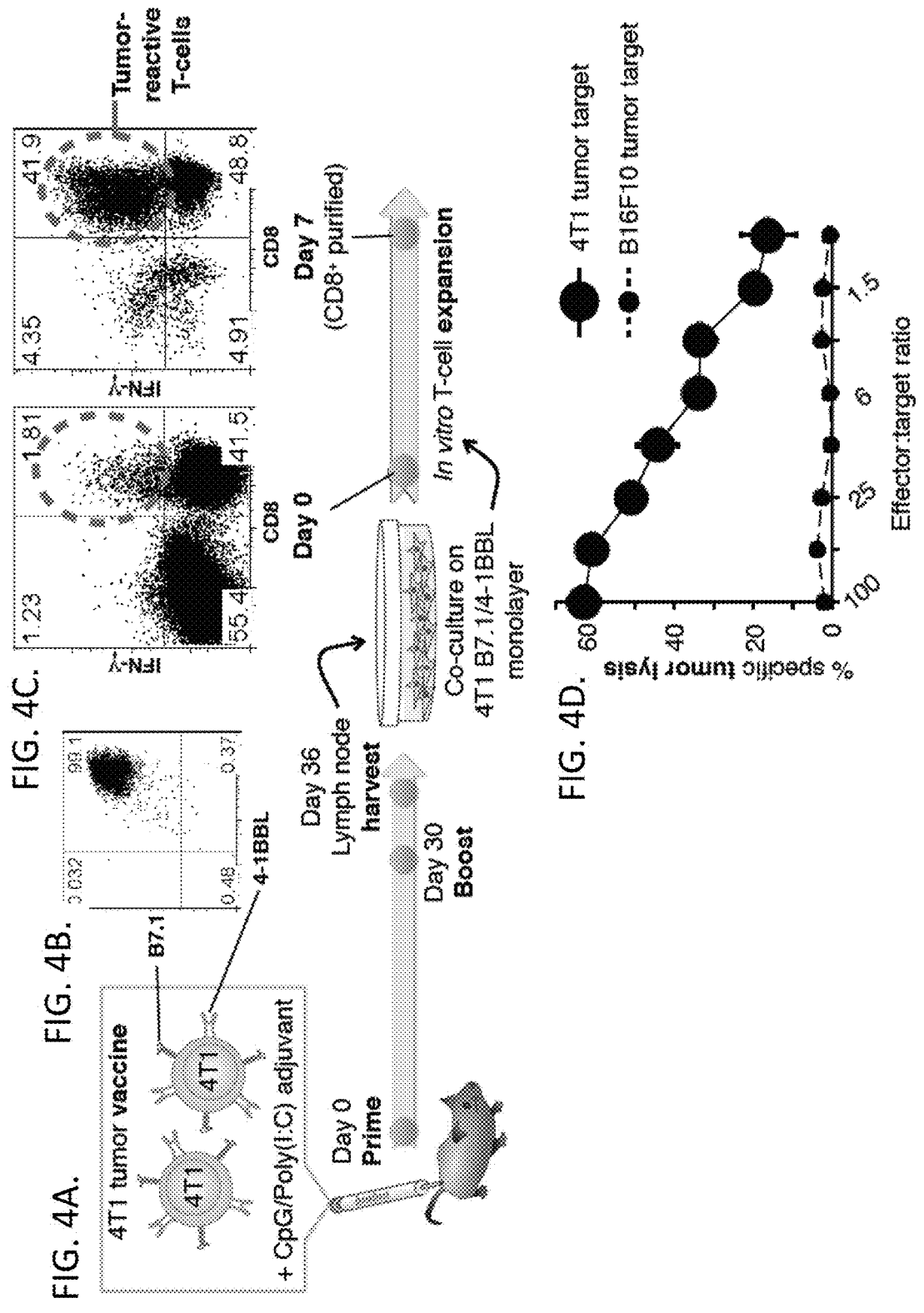
FIGS. 4A-4D. Fully functional tumor-reactive CD8+ T-cells can be isolated and expanded from vaccine-immunized mice.

Example 1. Generation and Ex Vivo Expansion of 4T1 Breast Tumor-Reactive Mouse T-Cells To model clinical ACT, in which tumor-reactive T-cells are isolated from patients and expanded in the laboratory, an established protocol to obtain breast tumor-specific T-cells from BALB/c mice (Restifo, Nat Rev Immunol 12, 269-281 (2012) which is incorporated by reference herein for its teachings regarding the same) was optimized. First, a 4T1 mammary carcinoma cell line that expresses the costimulatory ligands B7.1 and 4-1 BBL was generated using retroviral vectors (FIGS. 4A and 4E). This genetic modification helps the immune system recognize 4T1 tumor antigens as foreign. Irradiated 4T1 B7.1/4-1 BBL (hereafter 4T1-STIM) cells act as a whole cell cancer vaccine and prime tumor-specific T-cells in BALB/c mice following tail-base injection ($4 \times 10^6$ tumor cells). To enhance further vaccine-driven immune responses, the adjuvants CpG oligodeoxynucleotide and poly(I:C) were mixed with 4T1-STIM cells before injection. Following a prime-boost immunization, $3 \times 10^5$ 4T1 tumor-reactive T-cells from inguinal and axillary lymph nodes of a single mouse can routinely be isolated. This is equivalent to 2% of all cells in the lymph node, as determined by flow cytometric measurement of IFN-γ after a 12-hour restimulation on 4T1-STIM cells (FIG. 4C, left panel). Subsequently, 4T1-specific CD8+ T-cells were rapidly expanded ~40-fold by in vitro coculture on 4T1-STIM monolayers in the presence of IL-2 and IL-15. The generated T-cells are functional (FIG. 4C, right panel) and selectively lyse 4T1 tumor cells (FIG. 4D).

Figure 5A:
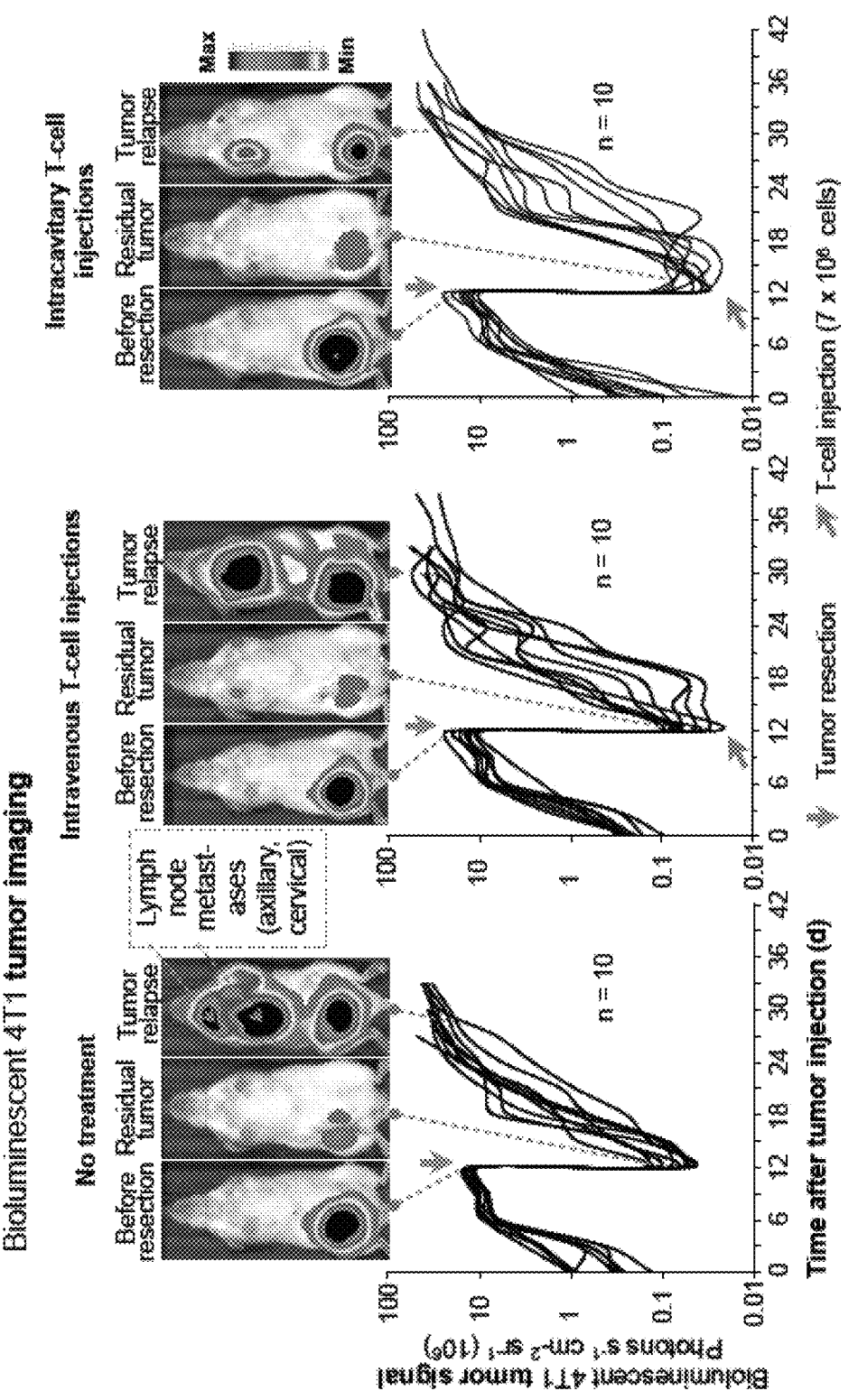
FIGS. 5A, 5B. Intravenous or intracavitary bolus injections of tumor reactive T-cells fail to clear incompletely resected tumor.

Example 2. Tumor-Reactive T-Cells Injected Intravenously or Locally into the Tumor Resection Bed Fail to Prevent Tumor Relapse Due to Inefficient Tumor Homing and/or Poor Persistence Whether standard intravenous injections of 4T1 tumor-reactive T-cells could reduce cancer relapse emanating from incompletely excised 4T1 tumor was assessed. The chosen 4T1 breast tumor model very closely mimics the tumor growth and metastatic spread of human breast cancer to lymph nodes, liver, lung, and bone. Tumor cells, retrovirally tagged with *Gaussia* luciferase for bioluminescence imaging, are easily transplanted into the right mammary gland of BALB/c mice and develop tumors that are ~10 mm in size after two weeks. At that time point, mice were preconditioned for the adoptive transfer of T-cells by removing homeostatic cytokine sinks by lymphodepletion (250 mg/kg cyclophosphamide, injected intraperitoneally). The following day, tumors were resected, leaving behind 0.1-1% residual disease as quantified by bioluminescent imaging (FIG. 5A, "Residual tumor"). Mice were either infused with T-cells the same day or received no treatment. Unexpectedly, all of the 10 animals treated intravenously with $7 \times 10^6$ tumor-specific T-cells relapsed with tumor (FIG. 5A, middle panel "Tumor relapse") and succumbed to disease at about the same time as untreated control animals (median survival: 33 versus 30 days, respectively; P=0.14). In an attempt to better protect mice from tumor recurrence, tumor-reactive T-cells were injected directly into the tumor resection cavity during surgery. Such intracavitary T-cell administrations yielded a statistically significant survival benefit compared with intravenous cell infusions (median survival: 37 versus 33 days, respectively; P=0.026). Nonetheless, residual tumor was not cleared in any of the treated mice and quickly relapsed from the primary resection site and from tumor-draining lymph nodes (FIG. 5A, right panel).

Figure 5B:
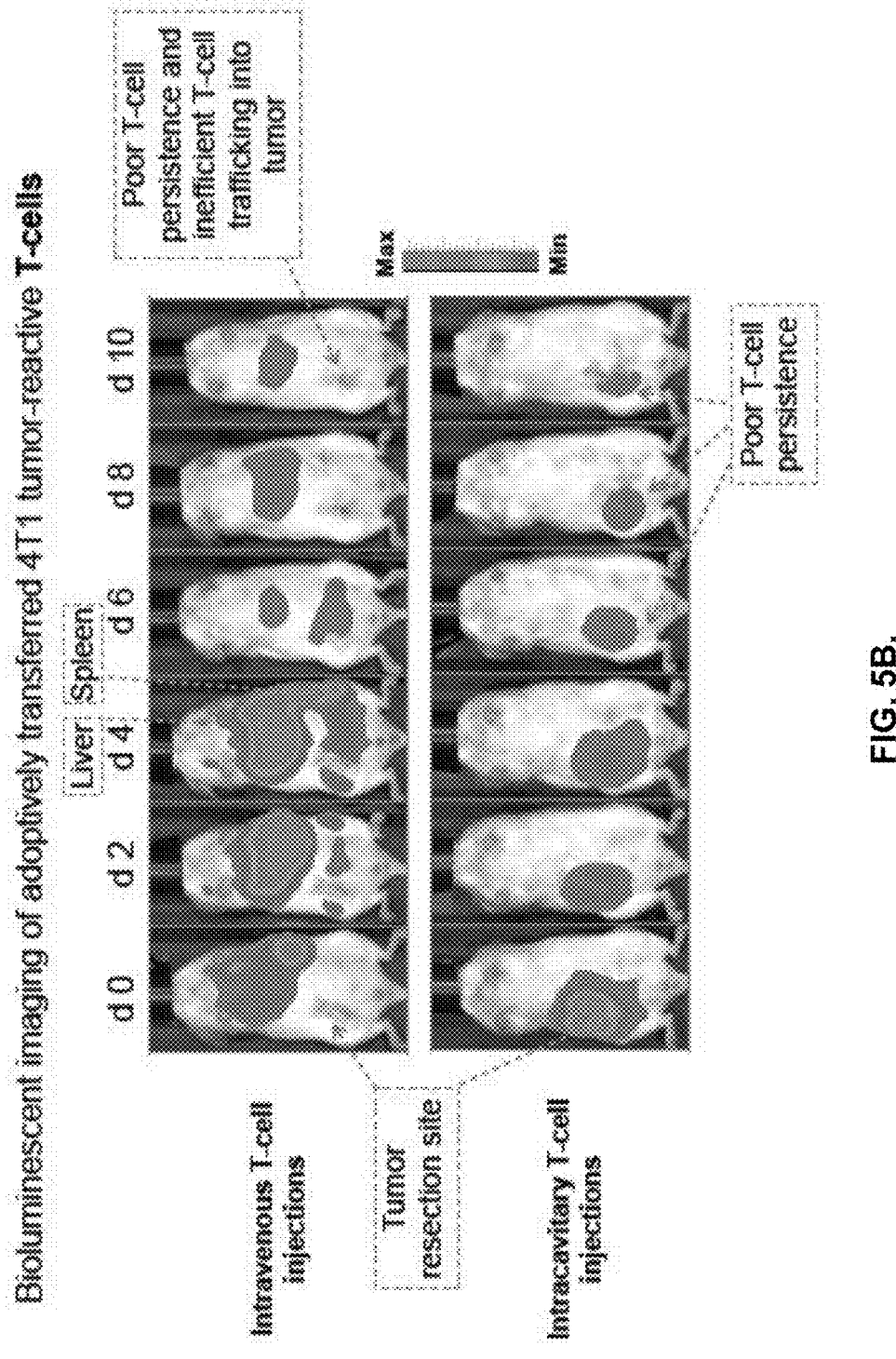

Why T-cell treatments failed to control disease recurrence was investigated. To track the in vivo migration and accumulation of transferred T-cells in relation to residual 4T1 tumor, T-cells were retrovirally-transduced with clickbeetle red luciferase (CBR-luc). Intravenously infused T-cells accumulated at high levels in the spleen and the liver, but poorly trafficked to relapsing tumor (FIG. 5B, upper panel). T-cells injected directly into the tumor bed cavity were readily detectable using bioluminescence on day 0. However, serial imaging showed a gradual CBR-luc signal decline following T-cell injection, consistent with poor T-cell expansion and persistence (FIG. 5B, lower panel).

Taken together, these results suggest that, despite the high tumor cell lysis observed in cytotoxicity assays in vitro (FIG. 4D), bolus injections of tumor-reactive T-cells given by the intravenous or intracavitary routes fail to control tumor relapse. This failure is due to inefficient accumulation of injected T-cells at the tumor site and/or a poor T-cell persistence and proliferation in the tumor resection bed.

Example 3. Porous Polysaccharide Scaffolds Coated with Collagen-Mimetic Peptide Support Rapid "Lymph Nodelike" Motility and Sustain the Viability of Embedded T-Cells To address the issues noted above, implantable compositions were created to produce a new microenvironment at the tumor resection site conducive to the sustained prolif-eration of transferred lymphocytes. The compositions can be used to deliver tumor-reactive lymphocytes to residual tumor following resection while sustaining their effector function and survival. To function as a lymphocyte delivery and release platform, a composition needs to provide suffi-cient mechanical support for embedded cells, a cell-adhesive coating to enable loaded cells to migrate through the mate-rial and exit into tissue, and appropriate stimulatory signals to trigger cell proliferation.

Figures 6A, 6B:
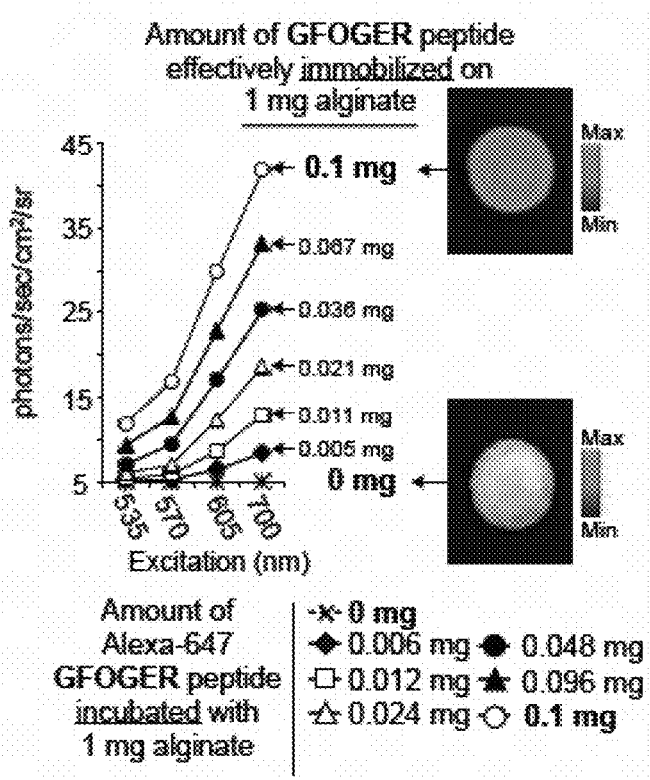

As an example, under physiological conditions, T-cells migrate in peripheral tissue along collagen fibers. Whether anchoring the collagen-mimetic GFOGER (SEQ ID NO:1) peptide to the inner walls of porous alginate scaffolds could support intra-scaffold migration of loaded T-cells was assessed. GFOGER (SEQ ID NO:1) peptide utilized in the examples is a synthetic triple helical peptide (purchased from the MIT Biopolymers facility (SEQ ID NO:2)) that binds to the collagen receptor $\alpha_2\beta_1$ on T-cells. GFOGER (SEQ ID NO:1) peptide was immobilized onto alginate using aqueous carbodiimide chemistry (FIG. 6A). Peptides were fluorescently labeled with DYLIGHT® 650 to quantify coupling efficiencies using fluorescence imaging (FIG. 6B). Three-dimensional scaffolds from calcium crosslinked alg-inate solutions by a freeze-dry method were produced.

Peptide binding efficiencies ranged from 83% (0.005 mg peptide/mg alginate) for the lowest peptide concentration tested, to 53% (0.102 mg peptide/mg alginate) for the highest peptide concentration tested (FIG. 6B). The highest peptide concentration was selected for use in subsequent experiments.

To evaluate the effect of GFOGER (SEQ ID NO:1) peptide immobilization, T-cell migration inside scaffolds using time-lapse video microscopy was recorded (FIG. 6C). The GFOGER (SEQ ID NO:1) peptide coating supported a rapid pore-to-pore T-cell migration quantitatively similar to the high motility of these cells in native secondary lymphoid organs (7.9 μm/min, FIG. 6C). In contrast, T-cells poorly migrated through uncoated scaffolds (3.6 μm/min), with most cells merely circling within their initial pore space (FIG. 6C, lower left panel). Notably, contact with GFOGER (SEQ ID NO:1) peptide sustained the viability of loaded T-cells (FIG. 6E), which is consistent with reports describing the activation of pro-survival signaling pathways in T-cells binding collagen.

The results suggest that GFOGER (SEQ ID NO:1) pep-tide-functionalized alginate scaffolds support rapid T-cell migration and sustain T-cell survival.

Figure 7A:
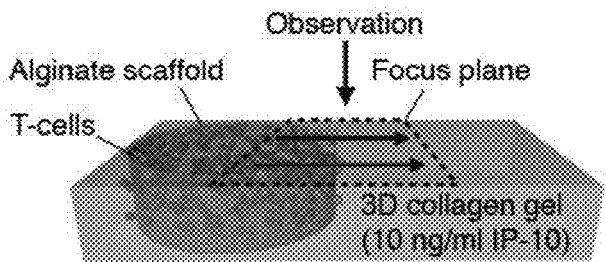
FIGS. 7A-7E. GFOGER (SEQ ID NO:1) peptide-coated alginate scaffolds disperse functional T-cells into tissue.
Figure 7B:
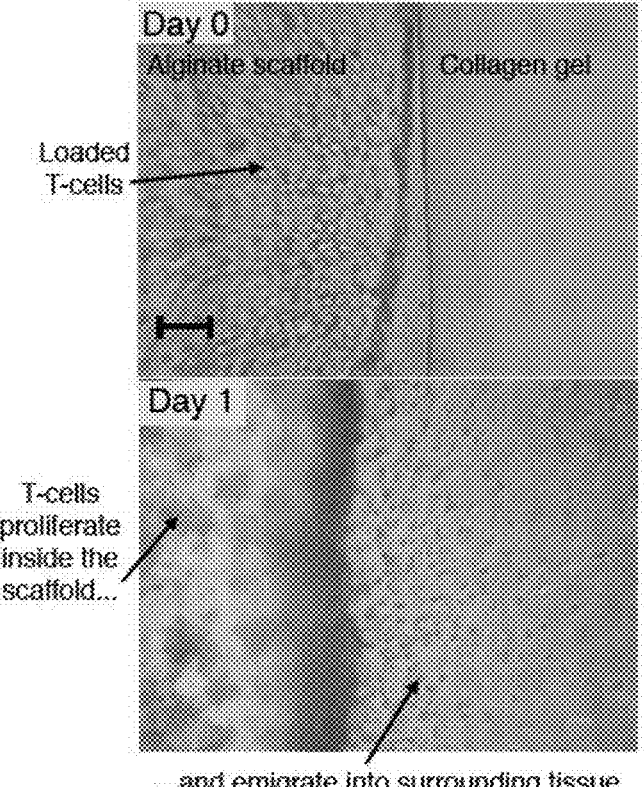
Figure 7C:
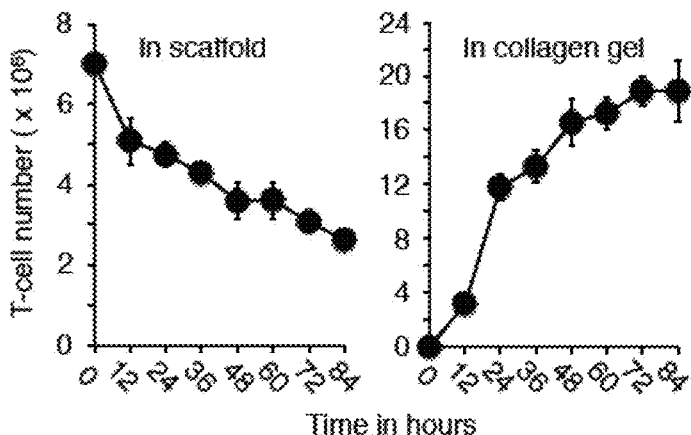
Figure 7D:
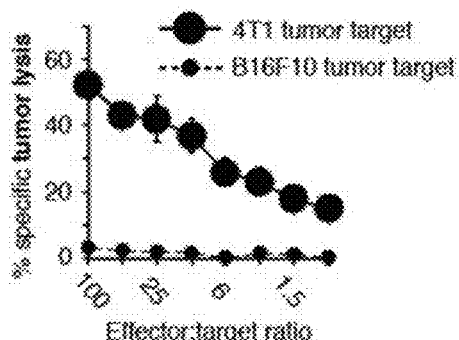

Example 4. Scaffolds Release Functional Tumor-Reactive T-Cells into Surrounding Tissue Whether T-cells can migrate outward from GFOGER (SEQ ID NO:1) peptide-coated scaffolds into surrounding tissue was examined. To mimic collagen-rich and inflamed tissue near surgical resection margins, three-dimensional (3D) collagen gels containing the inflammatory cytokine IP-10 were prepared (FIG. 7A). Scaffolds loaded with $7\times10^6$ 4T1 tumor-reactive T-cells were then embedded inside the collagen gel. T-cell egress from the composition was quan-tified every 12 hours for four days by counting viable cells in the scaffold and the collagen gel. T-cells gradually popu-lated the surrounding tissue mimetic at high numbers, reach-ing a peak of $18.9\times10^6$ T-cells after 72 hours (FIGS. 7B, 7C). Due to the continuous proliferation of loaded effector T-cells within the pore space of scaffolds (FIG. 7B, lower panel), outward cell migration only partially depleted the T-cell pool inside the scaffold (50% reduced T-cell number after four days, FIG. 7C).

Figure 7E:
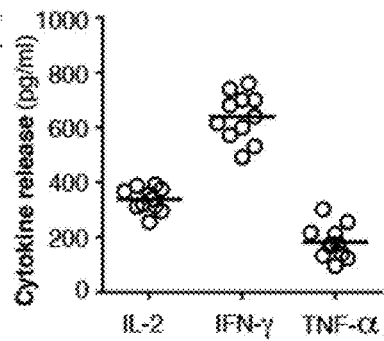

To determine whether T-cells that migrated out of com-positions were functional, their ability to lyse 4T1 tumor cells and to secrete cytokines was measured. Composition-dispersed T-cells efficiently killed 4T1 tumor targets and released high amounts of the effector cytokines IL-2, IFN-γ, and TNF-α, following co-culture on 4T1-STIM cells (FIG. 7E). In summary, GFOGER (SEQ ID NO:1)-peptide-coated scaffolds can efficiently disperse fully functional tumor-reactive T-cells into tissue.

Example 5. Incorporating Lymphocyte-Stimulating Ligands into Compositions Will Help Delivered Lymphocytes Overcome Poor Tumor Immunogenicity and an Adverse Tumor Microenvironment Polymer microparticles coated with a combination of anti-CD3, CD28 and CD137 antibodies are incorporated into the compositions and support proliferation of embedded lymphocytes and increase the number and functionality of the cells that migrate from the composition into surrounding tissue.

Example 5a. Fabrication of alginate scaffolds carrying stimulatory micro/nanoparticles. To become activated, T-cells must not only recognize antigen but also receive costimulatory signals from antigen presenting cells (APCs). To mimic physiological T-cell stimulation inside the scaf-fold, poly(lactic-co-glycolic acid) (PLGA) microparticles similar in size to APCs (10-20 μm in diameter, FIG. 8B, right panel) were synthesized. Particles were coated with avidin lipid so that biotinylated anti-CD3 antibodies and co-stimu-latory anti-CD28/CD137 antibodies could be anchored to their surface.

Stimulatory microparticle preparation (preparation of lipid film). Lipid stock solutions were prepared in chloro-form. 140 μL DOPC (10 mg/mL), 30 μL DSPE-PEG(2000) maleimide (5 mg/mL), 150 μL cholesterol (5 mg/mL), and 50 μL 18:1 PEG(2000) PE (5 mg/mL) were combined in a scintillation vial to attain a DOPC:DSPE-PEG(2000) male-imide:cholesterol:PEG(2000) PE mass ratio of 55:5:30:10 and 2.5 mg total lipid. Chloroform was evaporated under a stream of nitrogen and residual solvent was removed under vacuum overnight.

Loading of cytokine into mesoporous silica micropar-ticles. A suspension of spherical silica gel (15 μm particle diameter, 100 Å pore diameter) was prepared in PBS (100 mg/mL). 120 μL of the suspension was combined in a 1.5-mL polypropylene tube with 400 μL of IL15 SA (22 μg/mL). The suspension was gently agitated on a vortexer for 1 hour at room temperature (RT) then diluted with 480 μL PBS.

Lipid adsorption on silica. The entire $SiO_2$/IL15 suspen-sion (1 mL) was added to a 2.5-mg batch of lipid film. The mixture was vortexed for 15 seconds at 10 minute intervals for a total of 1 hour. The particles were centrifuged at 3500×g for 2 minutes then the supernatant was removed. The pellet was washed with PBS (3×1 mL) then redispersed in 500 μL PBS.

Antibody conjugation to silica-supported liposomes. The hinge-region disulfide bonds of anti-CD3, CD28, and CD137 were selectively reduced with dithiothreitol (DTT) as previously described [B. Kwong et al, Biomaterials (2011) 32:5134]. After removal of DTT with a desalting column, the mildly-reduced antibodies (anti-CD3: 200 μg;

anti-CD28 and CD137: 400 µg) were added to the maleimide-functionalized particles. The mixture was vortexed briefly then rotated at RT for 2 h. The resulting antibody-labeled particles were centrifuged at 3500×g for 2 min then the supernatant was removed. The pellet was washed with PBS (3×1 mL) then suspended in 125 µL PBS.

Figures 8A, 8C:
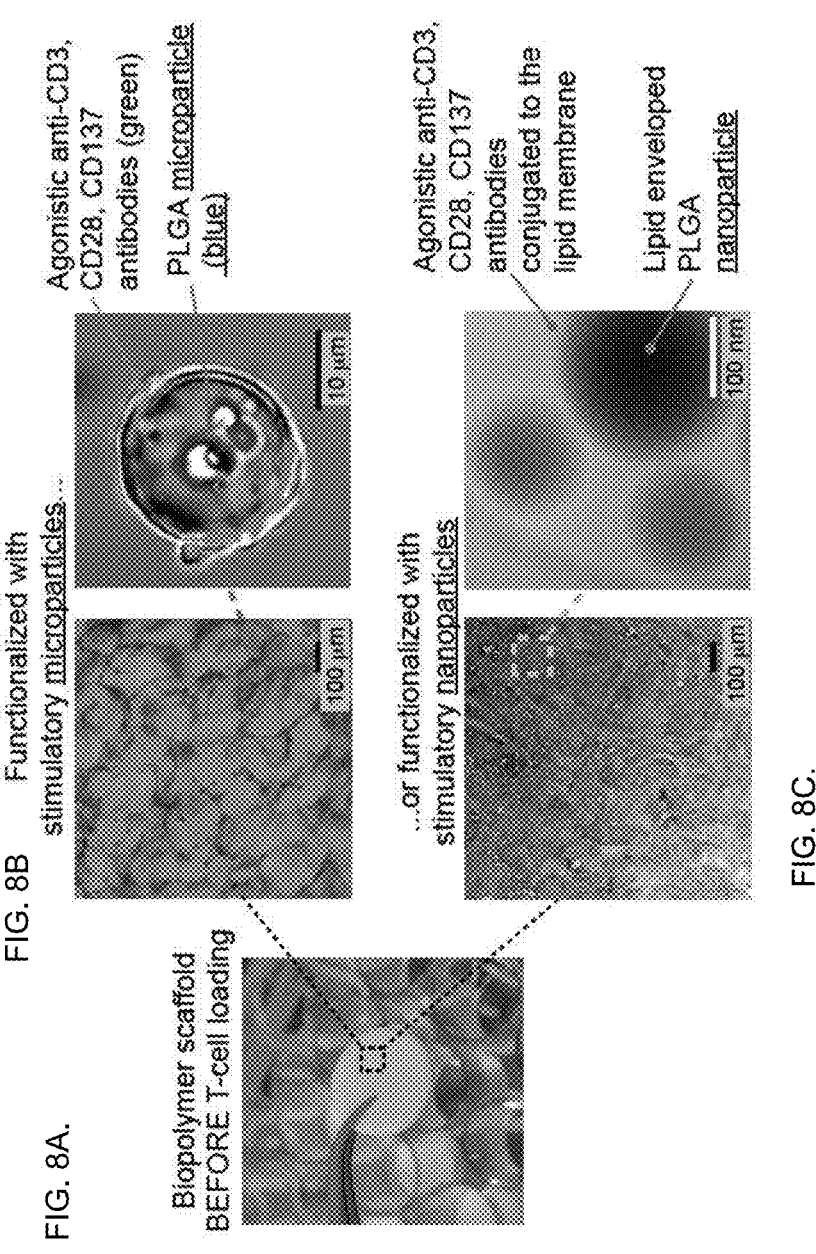

Prepared microparticles were then added dropwise to a 2% aqueous GFOGER (SEQ ID NO:1) peptide-modified alginate solution before cross-linking alginate with calcium chloride and molding 3D scaffolds by freeze drying (FIG. 8A). 7×10⁶ antibody-coated PLGA microparticles were incorporated into a single alginate implant. Particles were homogeneously dispersed within the pore network of the scaffold (FIG. 8B, left panel).

To determine the impact of particle size on the capacity to stimulate lymphocytes inside compositions, in parallel experiments equal amounts of stimulatory antibodies from the surface of ~100-fold smaller nanoparticles (100-150 nm in diameter) are displayed. Lipid-enveloped PLGA nanoparticles are then fabricated. Steenblock, et al., J Biol Chem, 286, 34883-34892 (2011) which is incorporated by reference herein for its teachings regarding the same. Briefly, an organic phase of PLGA polymer and DOPC, DOPG and maleimide-PE lipids are emulsified in water, leading to self-assembled lipid coatings surrounding each particle (FIG. 8C, right panel). Anti-CD3/CD28/CD137 antibodies, mildly reduced with DTT, are then covalently coupled to maleimide on the surface of nanoparticles as previously described. Bershteyn et al., Soft Matter, 4, 1787-1791 (2008) which is incorporated by reference herein for its teachings regarding the same. The amount of bioactive antibodies coupled to micro/nanoparticles is quantified by a functional ELISA assay. The lipid envelopes of particles are first solubilized in 0.5% Tween 20 surfactant.

Using recombinant mouse CD28/CD137/human Fc fusion proteins (R&D Systems) as capture agents, the amount of functional antibody in standard 96-well plates coated with anti-human IgG antibody using HRP-conjugated detection antibodies is then measured. Particle size/number is measured using the NanoSight LM20. Cryo-TEM images of particles (FIG. 8C, right) are generated by electron microscopy using a JEOL JEM 1400 Transmission Electron Microscope.

Example 5b. Comparison of lymphocyte expansion in microparticle vs. nanoparticle-functionalized compositions. The findings presented in FIGS. 8A-8C demonstrate that alginate scaffolds with incorporated stimulatory microparticles or nanoparticles can be successfully fabricated. To identify the best candidate scaffold/particle composition, in vitro T-cell assays described in detail in FIGS. 7A-7E are conducted. 7 million 4T1 tumor-reactive CD8+ T-cells are seeded either onto composite alginate/microparticle scaffolds (FIG. 8B), alginate/nanoparticle scaffolds (FIG. 8C) or plain scaffolds. For the initial studies, an equal number (7×10⁶) of microparticles and T-cells are embedded in each scaffold. Depending on the coupling efficiency of antibodies to the nanoparticles this correlates to 1×10¹⁰ nanoparticles/scaffold. Both T-cell expansion inside the scaffolds and cell migration into surrounding tissue (collagen gel) over an 84-hour time period (FIG. 7C) are examined. Differences in the ability of scaffold-released T-cells to kill 4T1 tumor (FIG. 7D) and to secrete effector cytokines (FIG. 7E) are also quantified.

Example 5c. Determination of optimal concentration of stimulatory signals to support lymphocyte expansion. The optimal concentration of stimulatory signals to support maximum lymphocyte expansion without compromising lymphocyte viability or key effector functions is determined. The main advantage of composite alginate/particle scaffolds is that the amount of stimulatory signal inside the scaffold can be finely tuned without further modifying the alginate backbone itself just by adding more or fewer stimulatory particles to the alginate solution before scaffold fabrication. Following identification of an optimized particle in Example 5b, the optimal particle:lymphocyte ratio inside the composition is determined. Alginate/particle scaffolds with a final microparticle:T-cell ratio of 0.5:1, 1:1, 5:1 and 10:1 (or 500:1, 1,000:1, 5,000:1 and 10,000:1, if nanoparticles are chosen) are fabricated and compared to T-cell proliferation and functionality using the same assays described in Example 5b.

Before finalizing parameters regarding the optimal number of stimulatory particles to incorporate into compositions for all subsequent in vivo studies, the phenotype of composition-released lymphocytes is characterized. Phenotypic traits are predictive of the ability of lymphocytes to survive long-term, to serially kill tumor cells, to migrate into tumor-draining lymph nodes and, in embodiments utilizing T-cells, to differentiate into memory T-cells. Therefore, in parallel studies, how increasing stimulation inside the composition affects the phenotype of T-cells exiting the implant is investigated. T-cells that have migrated out of alginate scaffolds (fabricated with various numbers of stimulatory particles as in previous experiments) into collagen gel after 72 hours are recovered. T-cells are analyzed by flow cytometry for the expression of the pro-survival factor Bcl-xL, the proliferation marker Ki-67, the marker for terminal differentiation and replicative senescence KLRG1, and the memory markers CD44, CD62L and CD122. Early apoptotic T-cells are identified by staining cells with Annexin-V and PI.

On the basis of pilot studies (FIGS. 7A-7E), comparative assays are carried out using eight scaffolds/conditions. This sample size provides 90% power to detect an effect size of 1 SD between groups, based on a one-way analysis of variance (ANOVA) with 2-sided significance level of 0.05 (calculated with Prism 6.0 GraphPad software).

The major goal of providing lymphocytes with (co-)stimulatory signals inside the composition is to compensate for the absence of these ligands on tumor cells—a mechanism used by tumors to render attacking lymphocytes dysfunctional. In particular, combined CD137 and CD28 signaling can synergistically enhance the anti-tumor effector function of T-cells while decreasing their susceptibility to apoptosis. Hence, it is expected that alginate scaffolds with incorporated anti-CD3/CD28/CD137 antibodies will mount a robust proliferative T-cell response. However, functionally exhausting T-cells or causing activation induced cell death by stimulating them excessively is avoided. If even low particle:T-cell ratios compromise T-cells functionality or survival, the strength of T-cell receptor activation is lowered. This is readily achievable by reducing the number of anti-CD3 antibodies and increasing the number of costimulatory anti-CD28/CD137 antibodies on the surface of particles.

Figures 9A, 9B, 9C:
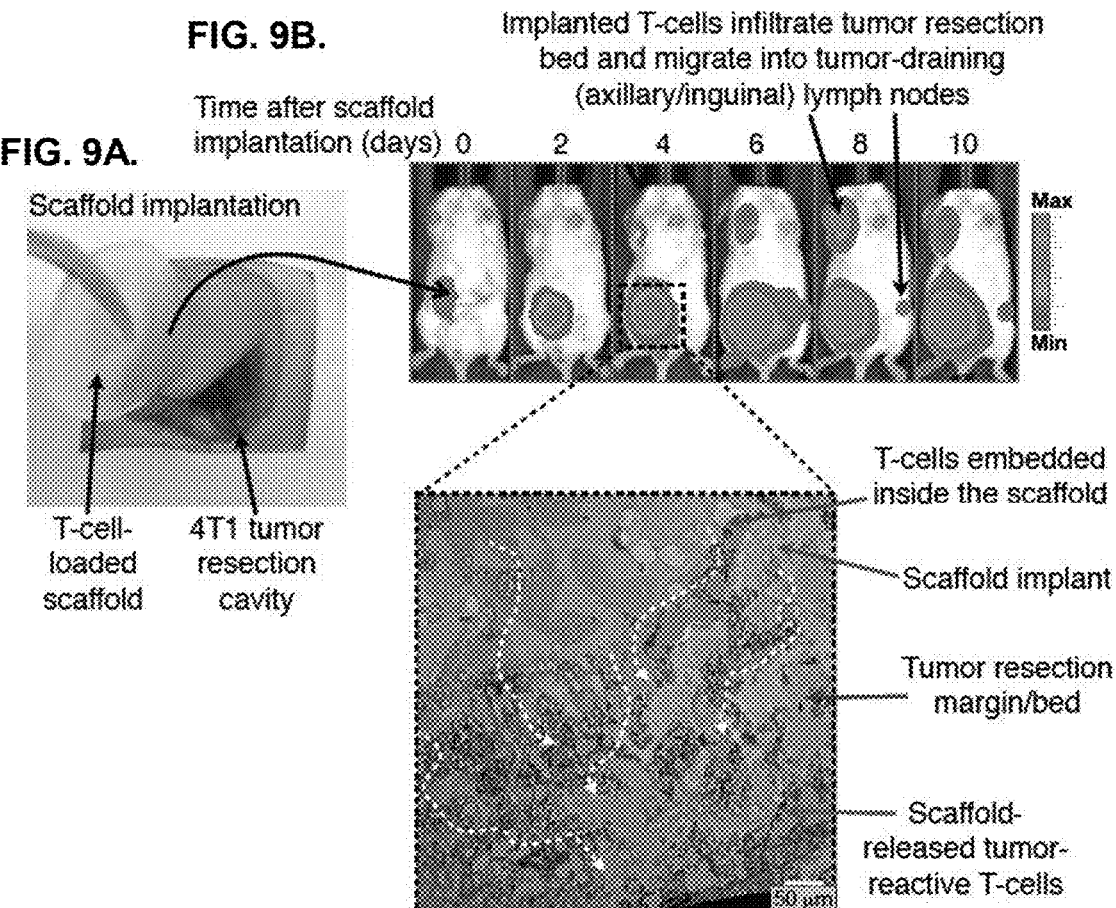
FIGS. 9A-9C. Tumor-reactive T-cells exit scaffolds over time and infiltrate surrounding tissue and tumor-draining lymph nodes.
Figure 11A:
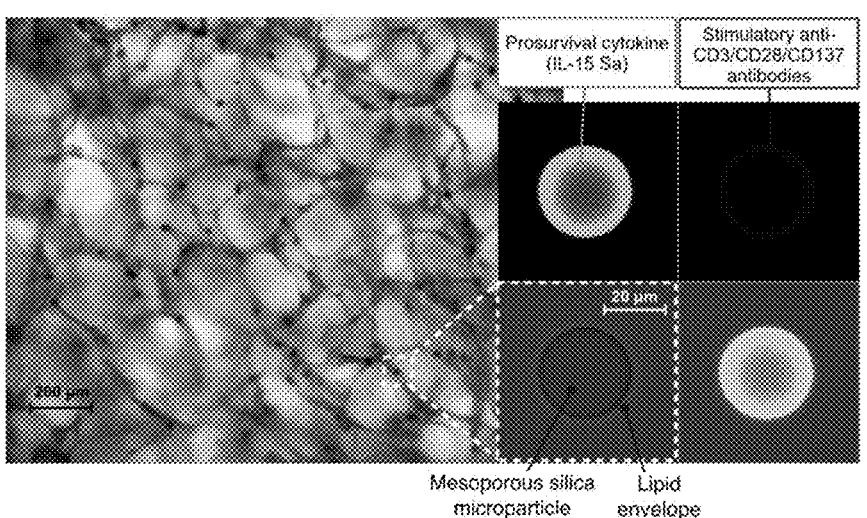
FIGS. 11A, 11B. Stimulatory signals trigger sustained T-cell expansion.
Figure 11B:
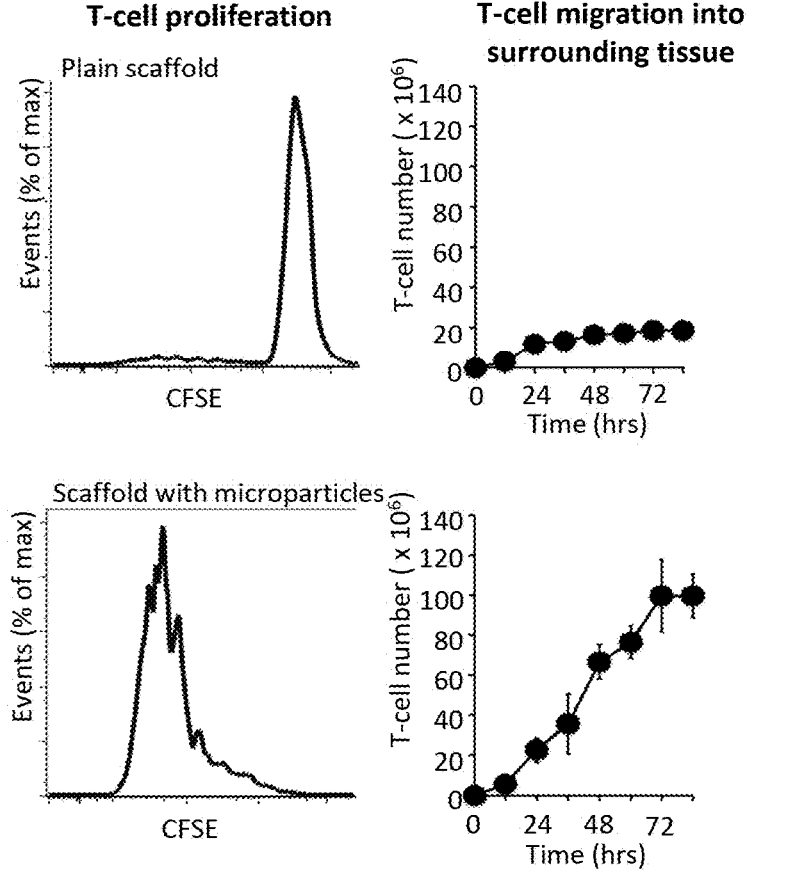

Example 6. The Ability of Composition-Mediated Lymphocyte Delivery to Prevent Tumor Relapse More Effectively than Conventional Lymphocyte Injections The described studies in 4T1 breast tumor-bearing mice suggest that neither systemic T-cell infusion nor local T-cell injection into the tumor resection cavity protects from disease recurrence (FIG. 5A). This was in part due to a poor T-cell persistence and the inability of cells to "find" residual tumor. To provide T-cells with niches that support their function and stimulate their proliferation directly at their primary treatment site—the tumor resection bed—a porous material composition delivery system was developed. Alginate matrices coated with the collagen-mimetic GFOGER (SEQ ID NO:1) peptide sustain the viability of embedded T-cells (FIGS. 6A-6E) and disperse functional tumor-reactive T-cells into surrounding tissue (FIGS. 7A-7E). Consistent with this notion, in mice T-cells exit implanted scaffolds at high densities over time and infiltrate the tumor resection bed and tumor-draining lymph nodes (FIGS. 9A-9C). Based on this data, the objectives of Example 6 is to (1) compare the therapeutic effectiveness of composition-supported lymphocyte delivery with conventional lymphocyte injections, and (2) elucidate underlying mechanism(s) by analyzing in vivo migration, expansion, persistence and phenotypic differences of transferred lymphocytes.

The studies will show that an appropriately designed composition can enhance the ability of lymphocytes to eradicate incompletely resected tumor.

Example 6a. Comparison of the therapeutic effectiveness of composition-supported lymphocyte delivery with conventional lymphocyte injections. Differences in the frequency of tumor relapse in BALB/c mice following incomplete 4T1 tumor resection (as shown in FIGS. 2, 5A, 5B, 9A, 9B, and 9C) are measured. Five different treatment groups are studied (18 mice/group). In one group, $7 \times 10^6$ 4T1 tumor-reactive T-cells from optimized compositions are delivered directly into the tumor resection cavity (as shown in FIG. 9A). Two groups of mice receive the same T-cell dose, but cells are either injected intravenously or locally into the resection bed. To assess therapeutic effects of the biomaterial itself, "empty" scaffolds (no T-cells) are implanted into one additional group of animals. All control mice are left untreated after surgery.

To quantitate differences in the tumor relapse rates between treatment groups, 4T1 tumors (retrovirally tagged with the *Gaussia* luciferase gene) are serially imaged every two days over a period of 42 days using bioluminescence imaging, as described in relation to FIG. 5A) using a state-of-the-art IVIS Spectrum (Caliper/Xenogen) whole-mouse imaging system. On the basis of preliminary data (FIG. 5A), a whole animal bioluminescent signal of >40× $10^6$ photons per second as the surrogate endpoint for death was defined to avoid unnecessary pain and distress in treated animals.

As described, alginate compositions are loaded with (co-) stimulatory antibodies (FIGS. 8A, 8B), whereas T-cells injected as a cell suspension are not supported by these ligands. Accordingly, composition-released T-cells would be expected to eradicate tumors more effectively merely as a result of receiving additional stimulation. Intravenously injected T-cells therefore are activated locally with an equivalent amount of stimulatory antibody incorporated into the compositions. To this end, T-cells are stimulated in 6-well plates with immobilized anti-CD3/CD28/CD137 antibody 24 hours prior to injection.

Example 6b. Analysis of in vivo migration, expansion, persistence and phenotypic differences of transferred lymphocytes. Appropriate localization and migration of lymphocytes is a prerequisite for anti-tumor responses. The described studies showed that dual bioluminescence imaging of *Gaussia* luciferase (Gau-luc) in 4T1 tumor cells and of clickbeetle red luciferase (CBR-luc) in tumor-reactive T-cells allowed simultaneously monitoring of tumor regrowth and T-cell biodistribution (FIGS. 5A, 5B). This assay is used to serially track the tissue distribution, expansion and persistence of composition-administered lymphocytes. Animals are imaged every two days for a period of 42 days or until they need to be euthanized. Whether there is a relationship between lymphocyte localization and sites of tumor recurrence are examined. To this end, CBR-luc (T-cell) and Gau-luc (tumor cell) signal intensities over the areas of the tumor resection site and the axillary lymph nodes where distal metastases first establish (FIG. 5A) are quantified with data graphed as scatter plots to identify correlations.

Example 6c. Effect of delivery mode on phenotype or functionality of composition-administered lymphocytes. Differences in lymphocyte phenotype and function between treatment groups are determined by flow cytometry. To distinguish composition-administered lymphocytes from host lymphocytes, 4T1 tumor-specific T-cells are generated in BALB/c mice that are congenic for the CD45.1 marker, as illustrated in FIG. 4A, and used to treat CD45.2 congenic recipient BALB/c mice. On day 4, 8 and 16 after transfer, three mice per treatment group are euthanized and single cell suspensions prepared from the tumor-resection bed, tumor draining lymph nodes (inguinal, axillary), and the spleen. One fraction of cells is stained with antibodies against CD8, CD45.1 and CD107a (LAMP-1) to detect degranulation associated with cytotoxic target killing. Two other cell fractions re stained with the memory markers CD127, CD44 and CD62L. To compare functionality, an equal number of isolated lymphocytes are restimulated for 12 hours on 4T1-STIM monolayers in the presence of brefeldin A, and intracellular IFN-γ or perforin are measured by flow cytometry, as shown in FIG. 4C. IFN-γ is a key effector cytokine, while perforin is a key mediator of target cell killing.

The described experiments show that even "plain" GFO-GER (SEQ ID NO:1) peptide-modified alginate scaffolds without stimulatory ligands sustain the viability and the proliferation of transferred T-cells at a tumor resection site (FIG. 9B versus FIG. 5B). It is expected that incorporating stimulatory cues into scaffolds will further enhance the expansion and functionality of composition-delivered lymphocytes. This translates into reduced tumor relapse rates in animals treated with compositions disclosed herein versus T-cell injections.

Example 7. Co-Delivering Immune Stimulants from Implanted Compositions can Enhance Act and Trigger Systemic Host Anti-Tumor Immunity In Example 7, the ability of compositions, beyond their primary function as lymphocyte delivery vehicles, to mount an effective host anti-tumor immune response capable of eliminating untreated distant metastases are tested. RLI is an IL-15-IL-15 receptor a fusion protein (FIG. 10A) that exhibits 50-fold greater potency than IL-15 alone. IL-15 impacts the anti-tumor immune response at multiple points. It can differentiate monocytes into stimulatory antigen presenting cells; promote the effector functions and proliferation of tumor-reactive T-cells; and recruit and activate NK cells. However, like most potent immune stimulants, IL-15 or its superagonist RLI requires high and sustained systemic doses to achieve the desired effect, leading to dose-limiting toxicities. Compositions disclosed herein focus drug action only on immune cells for which they were intended, thereby avoiding systemic overexposure to these agonists.

The experiments described in Example 7 investigate whether dispersing RLI from compositions into the tumor resection bed and the draining lymph nodes can (1) confer composition-delivered lymphocytes with markedly amplified anti-tumor effector functions and viability, and (2) orchestrate the destruction of untreated tumors throughout the body by activating dendritic cells, T-cells and NK-cells in the host. The results will show that combining delivery of RLI and tumor-reactive T-cells from compositions amplifies the expansion and persistence of transferred T-cells, using low RLI doses that have no effect when administered by traditional systemic routes. The results will further show that composition-released RLI transforms the peritumoral tissue and the tumor-draining lymph nodes from sites favoring immune suppression into "self" vaccine sites launching systemic anti-tumor immunity.

Example 7a. This example investigates whether dispersing RLI from implanted compositions can amplify the effector function and persistence of scaffold-delivered lymphocytes such as T-cells. 293-F cells are transduced with a plasmid encoding His-tagged RLI protein and RLI is purified from culture supernatant using a standard Cobalt agarose resin (FIG. 10B). Isolated RLI is fully functional, as demonstrated by its ability to enhance the proliferation of tumor-specific T-cells co-cultured on tumor monolayers (FIG. 10C). Poly(lactic-co-glycolic acid) (PLGA) micro- or nanoparticles, fabricated as described in Example 5a (including surface-anchored stimulatory antibodies), efficiently encapsulate RLI and slowly release it over a one-week period (FIG. 10D).

Using the information from Example 5a as to optimized PLGA micro- or nanoparticle compositions (FIG. 8B), either RLI-loaded micro- or nanoparticles are loaded into alginate compositions. Biodistributions of RLI following delivery via compositions disclosed herein relative to local or systemic bolus injections are measured. To this end, 10 µg RLI is administered either from compositions into 4T1 tumor resection cavities, or it is injected in its soluble form intravenously or into resection cavities. Blood serum and tissue samples of the tumor resection bed and tumor-draining (inguinal, axillary) lymph nodes re collected every two days for a period of 10 days. Tissue is homogenized with an ultrasonic dismembrator and centrifuged to collect supernatant. The amount of RLI per gram of tissue using a commercially available IL-15/IL-15Rα ELISA is measured.

Example 7b. Enhancement of lymphocyte function and viability following composition-released rli versus infusion-administered RLI. One group of mice is treated with T-cell-loaded compositions that contain 10-50 µg RLI. A second group of mice is treated with T-cell-loaded compositions and 10-50 µg intravenous RLI. 4T1 tumor relapse and T-cell expansion are quantitated in response to RLI given via different routes using bioluminescence imaging as in Example 2.

Example 7c. Composition-released RLI orchestration of untreated and/or distant tumor. Tumors render antigen-presenting cells in draining lymph nodes dysfunctional to prevent tumor-specific T-cells in the host from differentiating into cytolytic effectors. IL-15 has been reported to restore the antigen presenting capacity of dendritic cells (DCs) and reverse tolerance in tumor-specific T-cells. Thus, one predicted effect of local RLI delivery from compositions disclosed herein is activation of DCs in TDLNs coupled with the stimulation of anti-tumor T-cells in the host.

The frequency and phenotype of DCs in the TDLNs (inguinal, axillary) in mice treated with RLI-loaded scaffold implants versus systemically injected RLI (10 µg) or no exogenous RLI is analyzed. Lymph nodes and spleens are recovered from animals at day 2, 4 and 6 after treatment, digested with collagenase, and cells are stained with antibodies against CD11c, CD11b, CD40, CD80, and MHC I and II to detect costimulatory receptors and MHC molecules by flow cytometry.

In situ cytokine induction in DCs is analyzed by intracellular IL-12p40 staining. To measure the impact of RLI on the percentage of tumor-reactive T-cells in TDLNs, a fraction of cells on 4T1-STIM monolayers is restimulated and analyzed for IFN-γ production, surface CD107a and perforin expression in CD8+ T-cells by flow cytometry. Another cell fraction is stained with antibodies against CD49b to assess whether RLI increases the number of NK cells in the TDLNs or the spleen.

Example 7d. Ability of compositions to eliminate distant tumor metastases. The ultimate goal of local immunotherapy is the generation of a systemic immune response capable of eliminating disseminated tumors and distant metastases following treatment of an accessible tumor site. To test whether local scaffold implantation into the tumor resection cavity can drive systemic/distal tumor inhibition, 4T1 tumors in the lungs of mice that just underwent incomplete 4T1 breast tumor resection are established. 4T1 tumor cells are known to form lung metastases when injected through the lateral tail vein. One million 4T1 tumor cells tagged with luciferase are infused to allow for bioluminescence imaging of 4T1 tumors in the lungs simultaneously with relapsing 4T1 tumors at the primary tumor resection site. Five days after i.v. tumor injection, animals are treated with: (1) compositions loaded with 10-50 µg RLI only, (2) compositions loaded with $7 \times 10^6$ 4T1 tumor-reactive CD8+ T-cells only, (3) compositions loaded with both RLI plus T-cells, or (4) as control, "empty" (cell-free and RLI-free) compositions.

First differences in tumor growth between experimental groups at the resection site, the TDLNs and in the lungs using the bioluminescence tumor imaging assays described in Example 2 are quantitated. To elucidate underlying mechanisms, tissue from the tumor resection cavity, the TDLNs, the lung, and the spleen are harvested at days 4, 8, and 12 after treatment, and analyzed for frequencies and phenotypes of tumor-reactive T-cells, dendritic cells (DCs), and NK cells in the host by flow cytometry as described above in relation to Examples 5c and 6b. To distinguish host cells from transferred cells, $CD45.2^+$ recipient mice are treated with $CD45.1^+$ T-cells.

For biodistribution studies and flow cytometry assays, 12 mice/condition are studied (four mice/group, three experiments). For tumor imaging experiments 18 mice/group are studied. Statistical analyses is performed as described in Example 5.

By exposing scaffold-deployed T-cells and host immune cells to high concentrations of RLI over an extended period, synergistic anti-tumor responses are elicited.

Example 8

Particles were created by coating porous silica microparticles with lipid bilayers that mimic cell membranes. Light microscopy image of alginate scaffold with incorporated microspheres is shown in FIG. 18E. The high pore volume and surface area of the silica core allow high-capacity encapsulation and sustained release of soluble biomolecules. The T-cell stimulant interleukin 15 superagonist was encapsulated. The lipid membrane used to envelop particles serves as a modular scaffold for the attachment of a variety of lymphocyte-stimulating ligands. Agonistic anti-CD3, anti-CD28 and anti-CD137 monoclonal antibodies were covalently coupled to the surface of microspheres containing IL-15/IL-15Rα. These prepared particles were then added to a GFOGER (SEQ ID NO:1) peptide-modified alginate solution before molding 3D scaffolds. An in vitro assay, a schematic of which is shown in FIG. 18C, is used to quantify the migration of tumor-reactive T-cells from an alginate scaffold into a tissue mimetic (3D collagen gel). Light microscope images of tumor-reactive T-cells that have migrated from the scaffold into the 3D collagen gel are also shown in FIG. 18C.

Figure 18A:
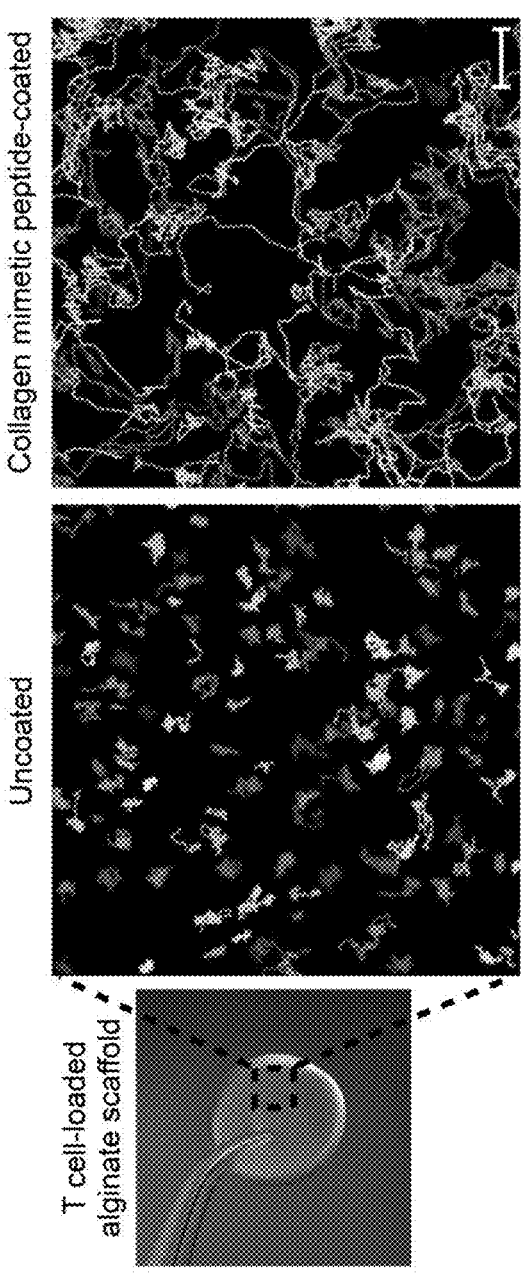
FIGS. 18A-18G.
Figure 18B:
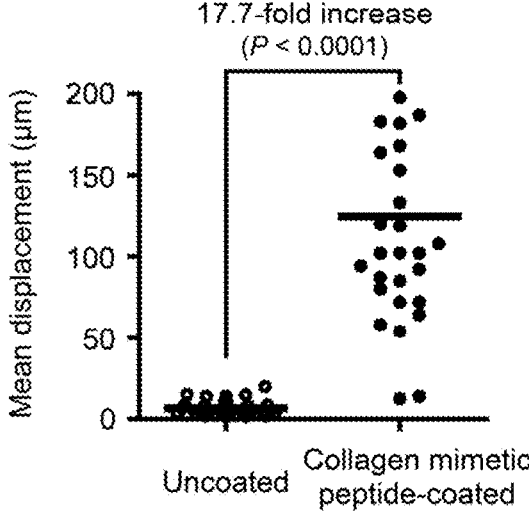
Figure 18C:
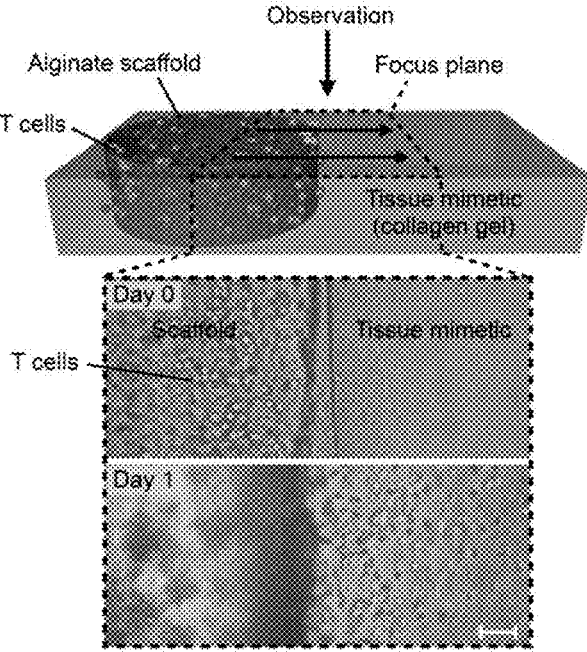

A photomicrograph of a T-cell loaded alginate scaffold and time-lapse images of T-cells migrating through unmodified or GFOGER (SEQ ID NO:1)-peptide-coated alginate scaffolds are shown in FIG. 18A. The trajectories of individual T-cells tracked for 30 minutes are shown. FIG. 18B shows a graph of mean displacements of T-cells during the 30-minute imaging interval.

Figure 18D:
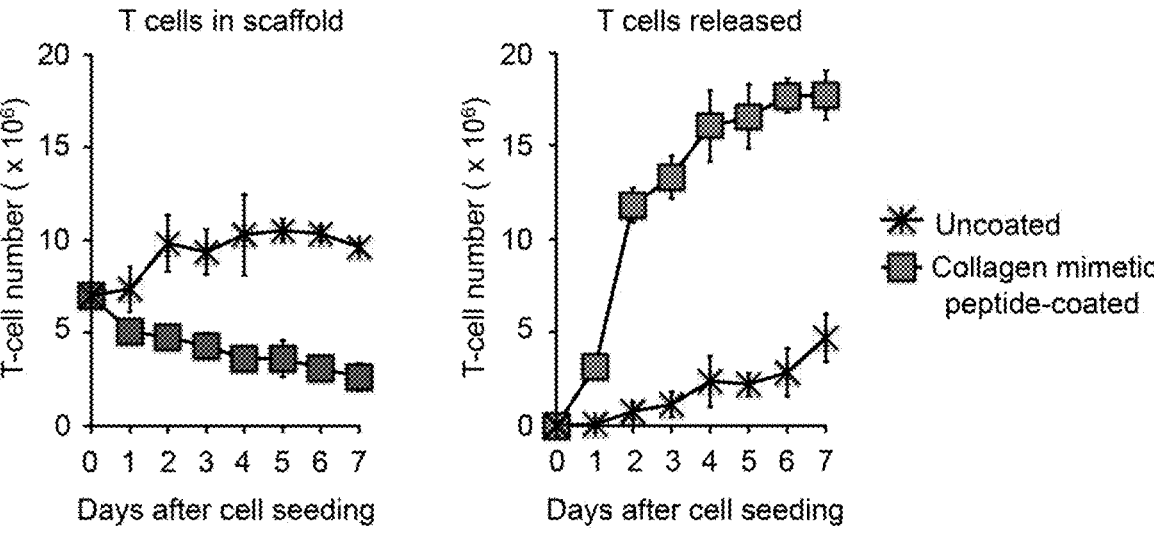
Figure 18E:
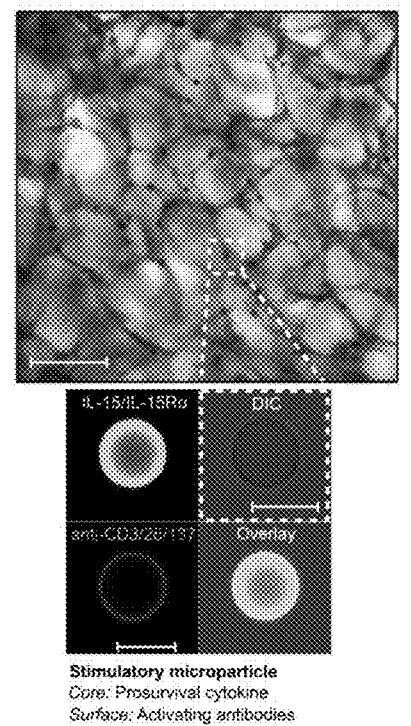
Figure 18F:
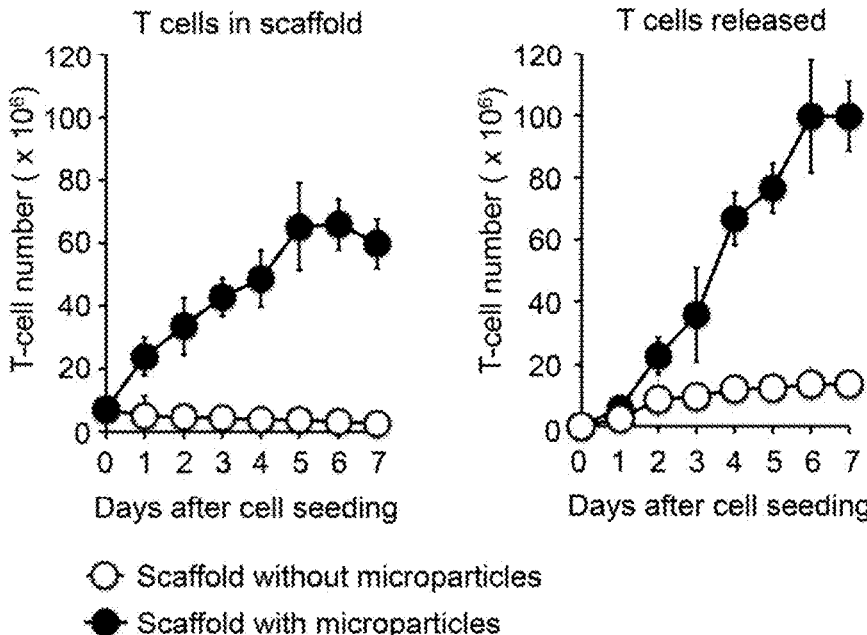

Quantification of T-cells in the alginate scaffold and in the collagen matrix. At indicated time points, T-cells were recovered from scaffolds and collagen gel by alginase or collagenase enzyme digestion, respectively. The number of viable T-cells was determined by Trypan Blue exclusion and graphed. (FIG. 18D).

Figure 18G:
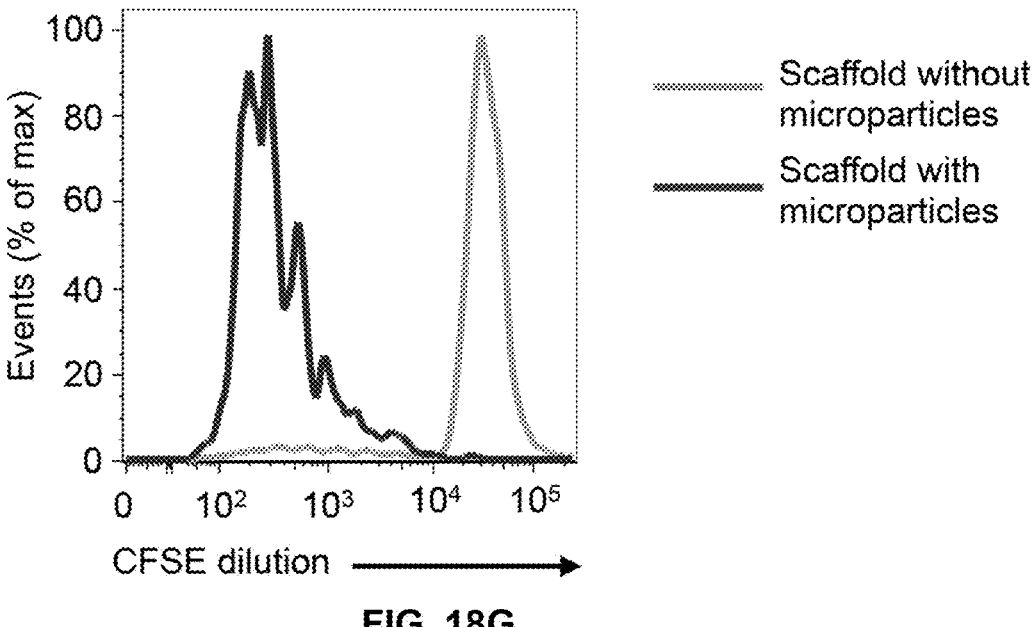

Quantification of T-cell egress from plain scaffolds, versus scaffolds carrying stimulatory microparticles. Using the in vitro assay from FIGS. 18C,18D, the number of viable T-cells in the scaffold and the surrounding collagen gel at given time points was determined. CFSE dilutions of T-cells embedded in plain versus microparticle-functionalized scaffolds were analyzed by flow cytometry 7 days after cell seeding, the results of which are shown in FIG. 18G.

Example 9

Figure 12A:
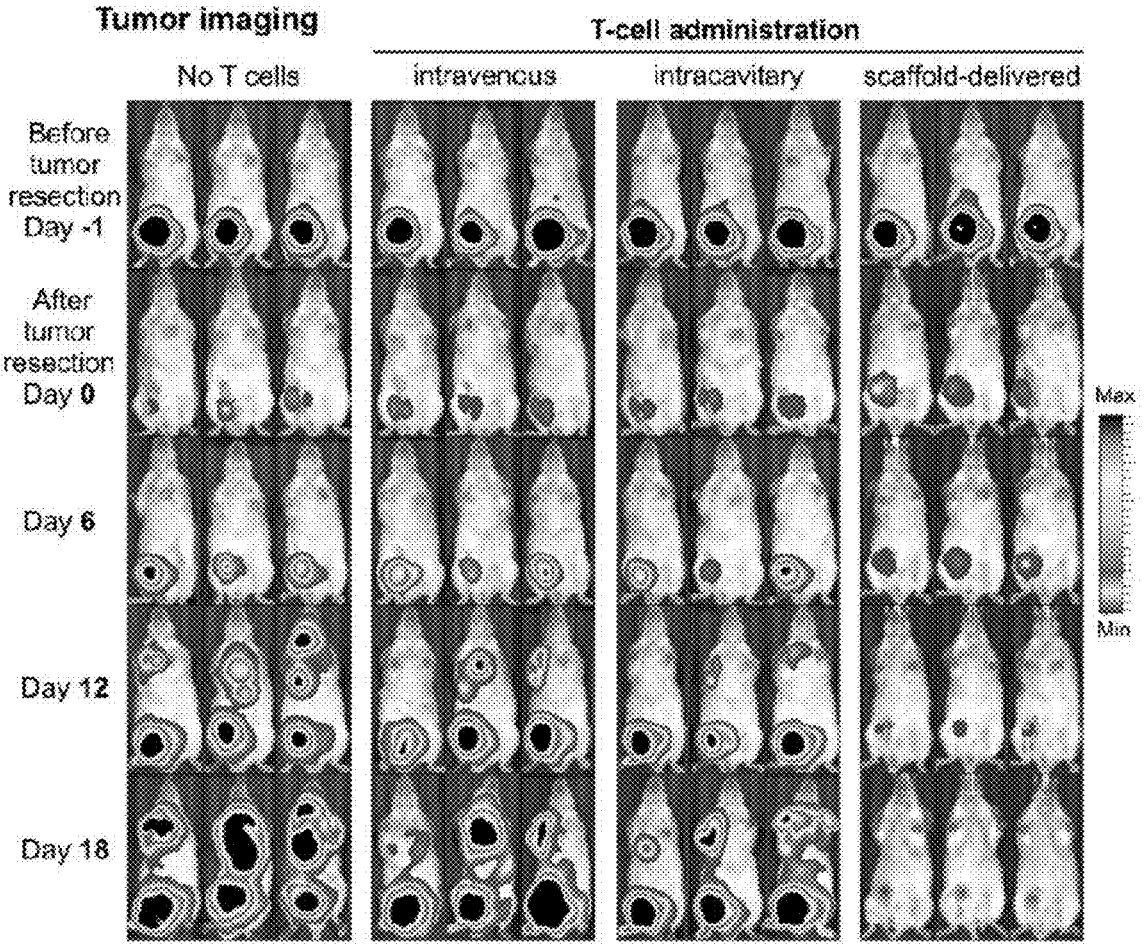
FIGS. 12A-12F. Longitudinal bioluminescence imaging of luciferase-expressing 4T1 breast tumor tumors.
Figure 12B:
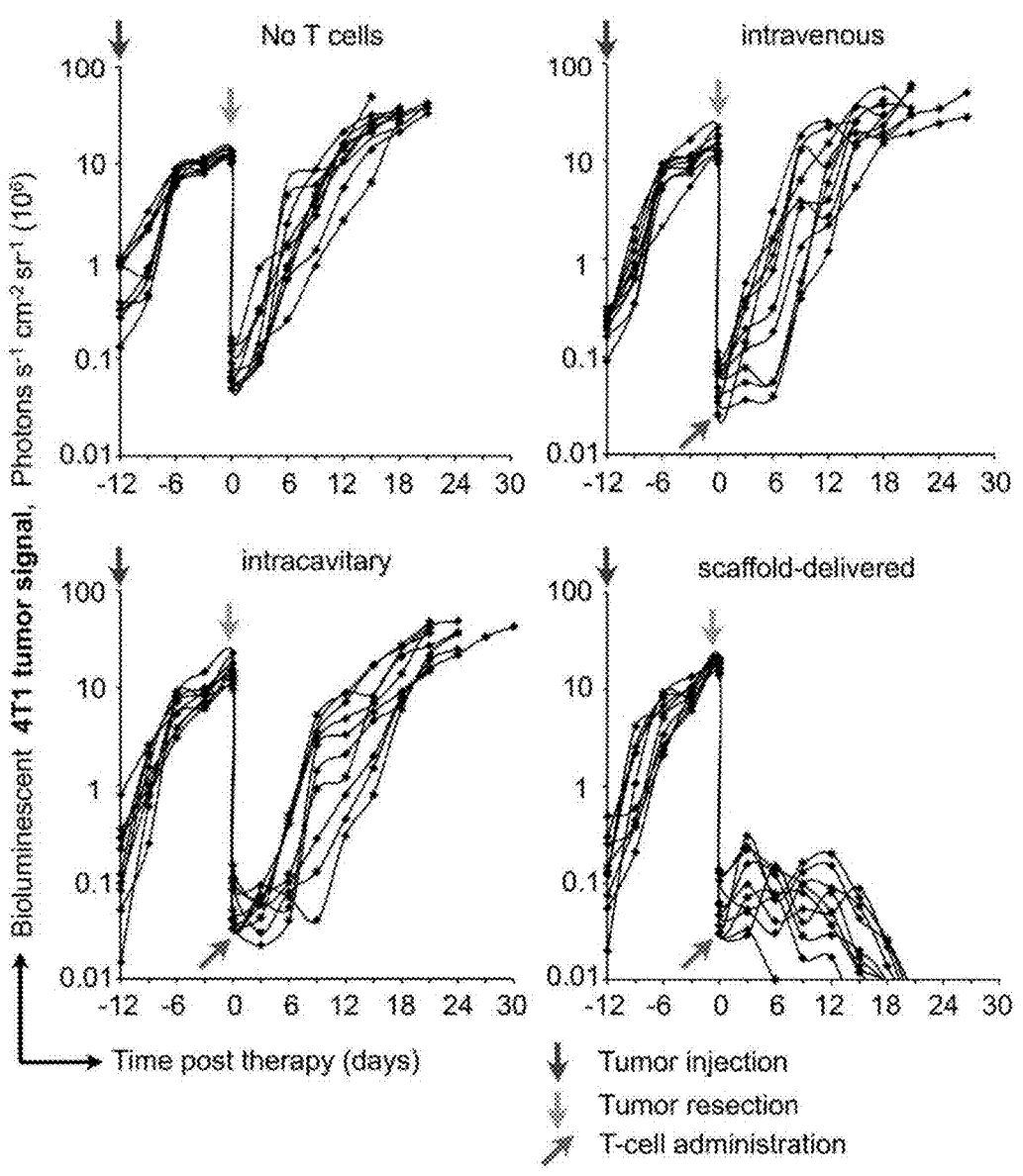
Figure 12C:
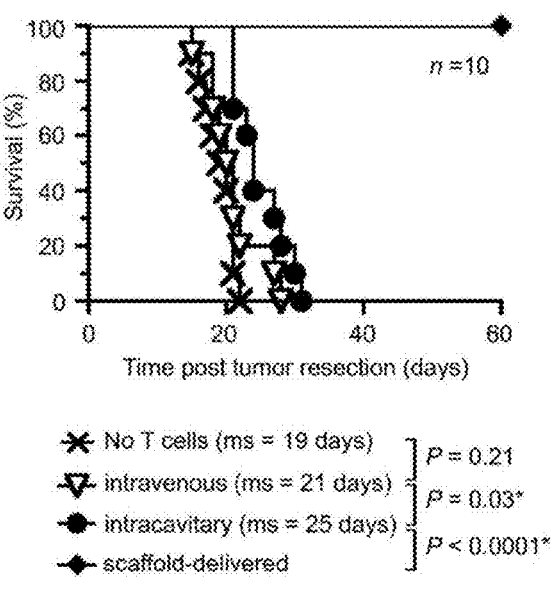
Figure 12D:
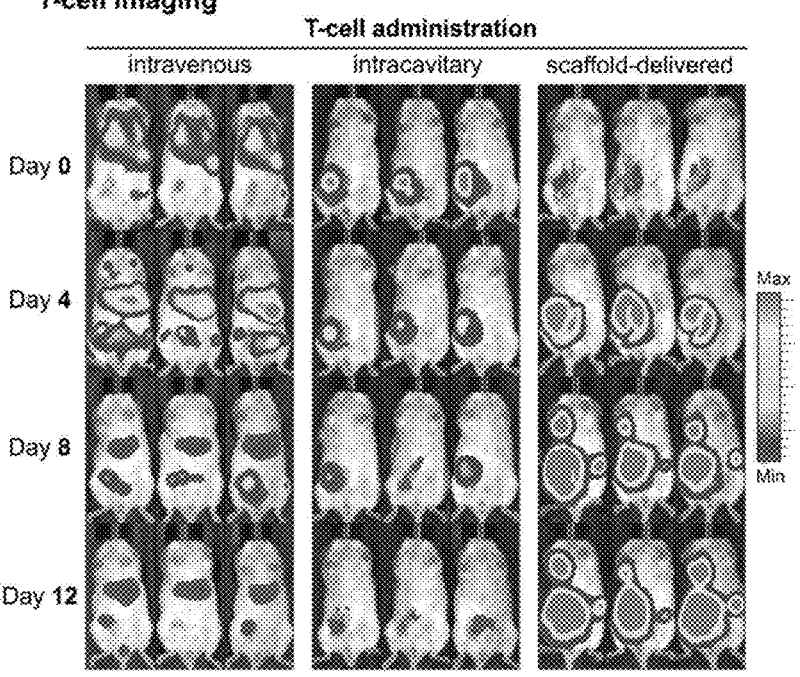
Figure 12E:
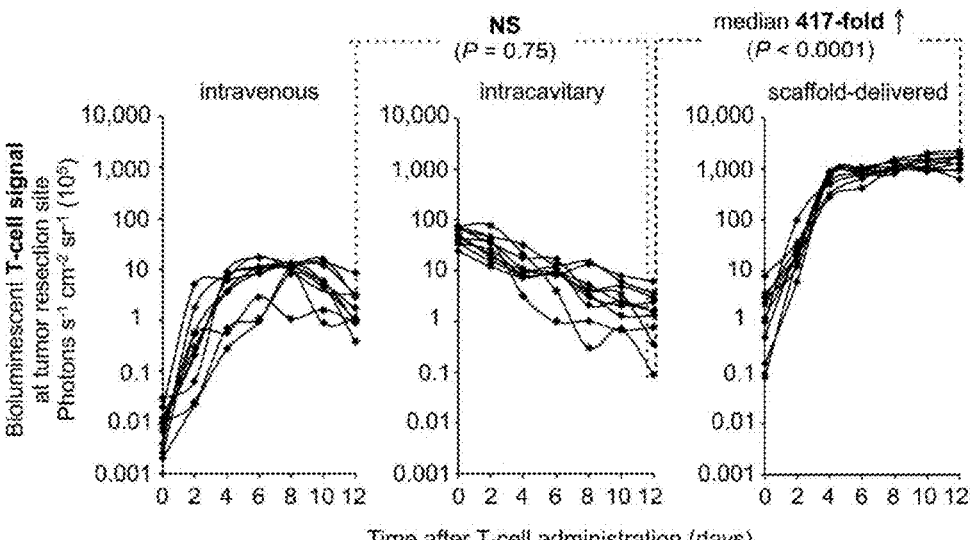
Figure 12F:
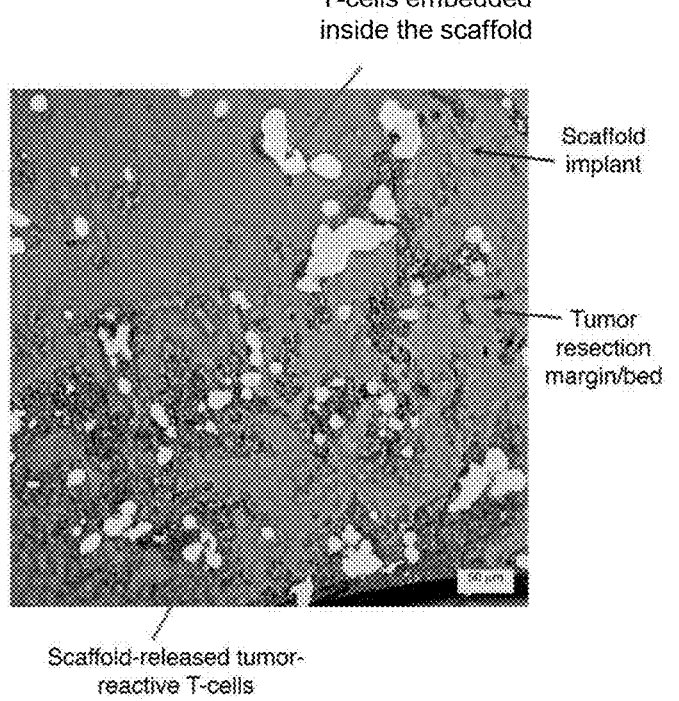
Figure 13:
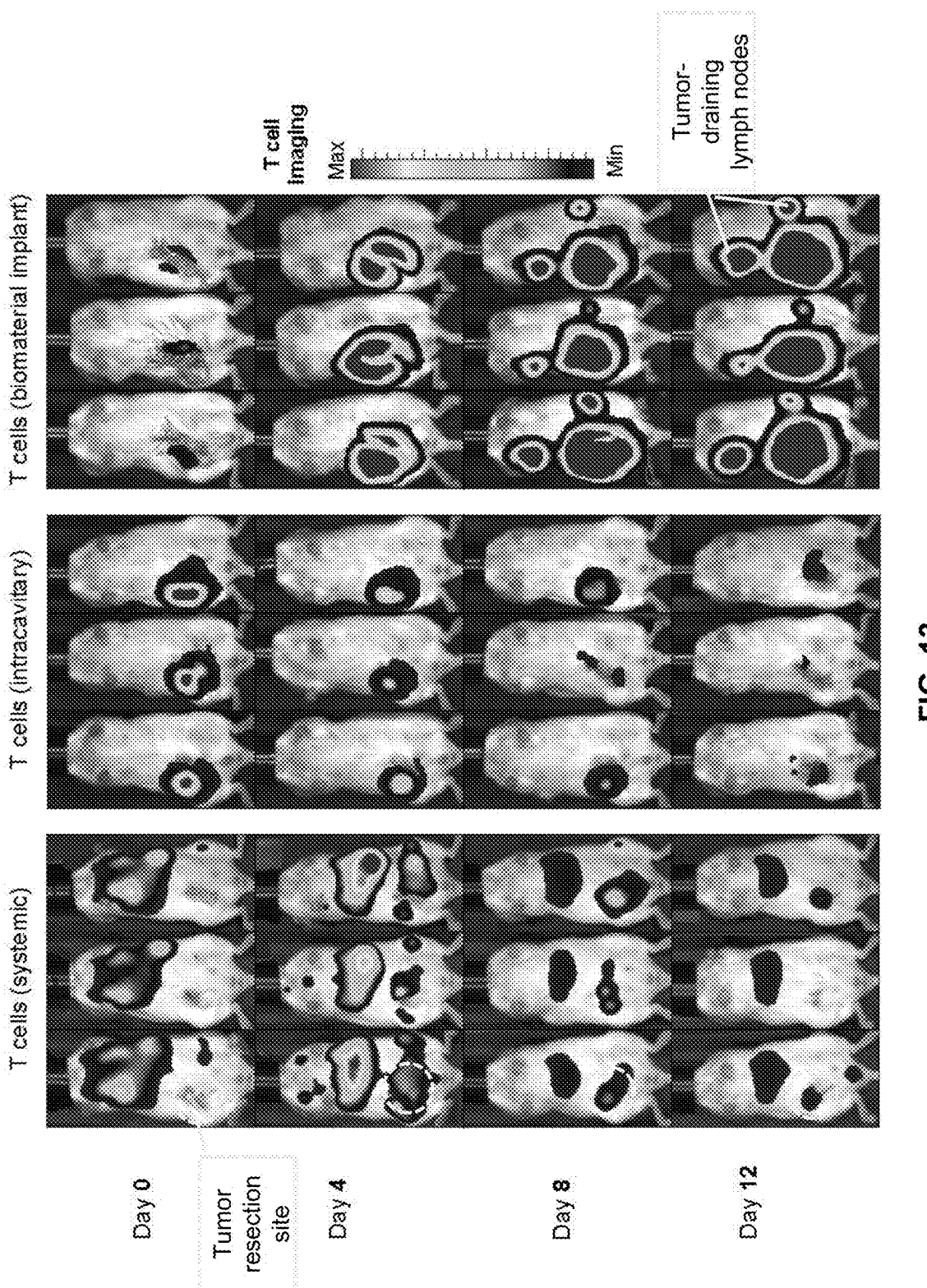
FIG. 13. Sequential bioluminescence imaging of adoptively transferred 4T1 tumor-reactive T-cells retrovirally transduced with CBR-luc at 0, 4, 8 and 12 days after administration. Representative images from a total of 3 mice/group imaged every four days are shown.

Tumor cells were transplanted into the mammary gland, and ten days later, tumors were resected such that ~1% residual diseased tissue remained. Four different treatment groups were compared. In one group, $7 \times 10^6$ 4T1 breast tumor-specific T-cells contained in scaffold were delivered directly into the tumor resection cavity. Two groups of mice received lymphocytes injected intravenously or locally into the resection bed, and control mice were left untreated. Sequential in vivo bioluminescence imaging of luciferase-expressing 4T1 breast tumors is show in in FIG. 12A. Representative acquisitions from a total of 10 mice/group imaged every two days are shown. Bioluminescent tumor signal quantified per animal every to days over a period of 30 days is shown in FIG. 12B. FIG. 19C shows survival of animals following T-cell therapy illustrated by Kaplan-Meier curves. Sequential bioluminescence imaging of adoptively transferred 4T1 tumor-reactive T-cell retrovirally transduced with luciferase is shown in FIG. 12D. Bioluminescent T-cell signal was quantified per animal every to days over a period of 12 days (FIG. 12E). FIG. 12F shows a confocal image of tumor-reactive T-cell (labeled with Cell-Tracker Green) as they exit the scaffold (Alexa-647-labeled) to populate the tumor resection bed four days after implantation.

Exemplary Embodiments

1. A composition comprising (i) a structure comprising an injectable polymer or scaffold comprising pores; (ii) lymphocytes disposed within the structure, (iii) at least one lymphocyte-adhesion moiety associated with the structure; and (iv) at least one lymphocyte-activating moiety associated with the structure.
2. A composition of embodiment 2, wherein the lymphocytes are T-cells and/or natural killer cells.

3. A composition of embodiment 1 or 2, wherein the lymphocytes are CD8+ T-cells.
4. A composition of any one of embodiments 1-3, comprising at least $7 \times 10^6$ lymphocytes.
5. A composition of any one of embodiments 1-4, wherein the lymphocyte-adhesion moiety comprises a collagen-mimetic peptide.
6. A composition of any one of embodiments 1-4, wherein the lymphocyte-adhesion moiety comprises a peptide that binds $\alpha_1\beta_1$ integrin, $\alpha_2\beta_1$ integrin, $\alpha_4\beta_1$ integrin, $\alpha_5\beta_1$ integrin, or lymphocyte function associated antigen (LFA-1).
7. A composition of any one of embodiments 1-4, wherein the lymphocyte-adhesion moiety comprises a GFO-GER (SEQ ID NO:1) peptide.
8. A composition of embodiment 7, wherein the lymphocyte-adhesion moiety comprises a GFOGER (SEQ ID NO:1) peptide of SEQ ID NO:2.
9. A composition of any one of embodiments 1-4, wherein the lymphocyte-adhesion moiety comprises an ICAM-1 peptide.
10. A composition of embodiment 9, wherein the lymphocyte-adhesion moiety comprises an ICAM-1 peptide of SEQ ID NO:3.
11. A composition of any one of embodiments 1-4, wherein the lymphocyte-adhesion moiety comprises a $FNIII_{7-10}$ peptide.
12. A composition of embodiment 11, wherein the lymphocyte-adhesion moiety comprises a $FNIII_{7-10}$ peptide of SEQ ID NO. 4.
13. A composition of any one of embodiments 1-12, wherein the lymphocyte-activating moieties are bound to or incorporated in one or more particles.
14. A composition of embodiment 13, wherein the particles are microparticles or nanoparticles.
15. A composition of embodiment 13 or 14, wherein the particles are microparticles with a diameter of 10-20 μm.
16. A composition of any one of embodiments 13-15, wherein the particles are microparticles and the ratio of microparticles to lymphocytes within the composition is 0.5:1; 1:1; 5; 1 or 10; 1.
17. A composition of embodiment 13 or 14, wherein the particles are nanoparticles with a diameter of 100-150 nm.
18. A composition of any one of embodiments 13, 14 or 17, wherein the particles are nanoparticles and the ratio of nanoparticles to lymphocytes within the composition is 500:1; 1000:1 or 5000; 1.
19. A composition of any one of embodiments 1-18, wherein the lymphocyte-activating moiety comprises antibodies specific for CD3, CD28, and/or CD137.
20. A composition of any one of embodiments 13-19, wherein the composition comprises $7 \times 10^6$ to $1 \times 10^{10}$ particles.
21. A composition of any one of embodiments 1-21, further comprising an immune stimulant.
22. A composition of any one of embodiments 13-20, wherein the particles further comprise an immune stimulant.
23. A composition of any one of embodiments 21 or 22, wherein the immune stimulant is a cytokine, an antibody, a small molecule, an siRNA, a plasmid DNA, and/or a vaccine adjuvant.
24. A composition of embodiment 23, wherein the cytokine is IL-2, IL-4, IL-10, IL-11, IL-12, IL-15, IL-18, TNFα, IFN-α, IFN-β, IFN-γ, or GM-CSF.

25. A composition of any one of embodiments 21-24, wherein the immune stimulant is the interleukin-15 superagonist RLI.

26. A composition of embodiment 23, wherein the vaccine adjuvant is CpG oligodeoxynucleotide or Poly(I:C).

27. A composition of any one of embodiments 1-26, wherein the structure is injectable.

28. A composition of embodiment 1, wherein the lymphocyte-adhesion moieties and/or lymphocyte-activating moieties are associated with the structure in a bioactive coating on the scaffold.

29. A composition of embodiment 1, wherein the lymphocyte-activating moieties are associated with particles embedded in the pores of the scaffold.

30. A composition of embodiments 28 or 29, wherein the lymphocyte-activating moieties are associated with particles attached to the surface of the scaffold or are embedded in the scaffold.

31. A composition of embodiment 1, wherein the scaffold is an alginate scaffold.

32. A composition of embodiment 31, wherein the scaffold is a polymeric calcium cross-linked alginate scaffold.

33. A composition of any one of embodiments 1-32 wherein the lymphocytes, lymphocyte-adhesion moieties, and lymphocyte-activating moieties are within the structure of the composition.

34. A method of treating a tumor in a subject comprising implanting a composition of any one of embodiments 1-33 into a subject within a proximity to a tumor cell sufficient to lead to the destruction of the tumor cell in the subject, thereby treating the tumor.

35. A method of embodiment 34, wherein the implanting is within a tumor resection bed.

36. A method of embodiment 34 or 35, wherein the destroyed tumor cell is a cell of an incompletely resected tumor.

37. A method of embodiment 34 or 35, wherein the destroyed tumor cell is a cell of a metastasized tumor.

38. A method of any one of embodiments 34-37, wherein the implanting leads to the destruction of a tumor cell of an incompletely resected tumor or a tumor cell of a metastasized tumor.

39. A method of any one of embodiments 34-38 wherein the tumor cell is a seminoma cell, a melanoma cell, a teratoma cell, a neuroblastoma cell, a glioma cell, a rectal cancer cell, an endometrial cancer cell, a kidney cancer cell, an adrenal cancer cell, a thyroid cancer cell, a skin cancer cell, a brain cancer cell, a cervical cancer cell, an intestinal cancer cell, a liver cancer cell, a colon cancer cell, a stomach cancer cell, a head and neck cancer cell, a gastrointestinal cancer cell, a lymph node cancer cell, an esophageal cancer cell, a colorectal cancer cell, a pancreatic cancer cell, an ear, nose and throat (ENT) cancer cell, a breast cancer cell, a prostate cancer cell, a uterine cancer cell, an ovarian cancer cell, or a lung cancer cell.

40. A method of embodiment 39, wherein the tumor cell is a glioblastoma cell, a pancreatic adenocarcinoma cell or an ovarian cancer cell.

41. A method of reducing surgical treatment failure caused by metastatic relapse after resection of a primary tumor, comprising administering a composition of any one of embodiments 1-33 to a tumor resection bed of a subject thereby reducing surgical treatment failure caused by metastatic relapse after primary tumor resection.

42. A method of embodiment 41 wherein the primary tumor comprises a seminoma cell, a melanoma cell, a teratoma cell, a neuroblastoma cell, a glioma cell, a rectal cancer cell, an endometrial cancer cell, a kidney cancer cell, an adrenal cancer cell, a thyroid cancer cell, a skin cancer cell, a brain cancer cell, a cervical cancer cell, an intestinal cancer cell, a liver cancer cell, a colon cancer cell, a stomach cancer cell, a head and neck cancer cell, a gastrointestinal cancer cell, a lymph node cancer cell, an esophageal cancer cell, a colorectal cancer cell, a pancreatic cancer cell, an ear, nose and throat (ENT) cancer cell, a breast cancer cell, a prostate cancer cell, a uterine cancer cell, an ovarian cancer cell, or a lung cancer cell.

As will be understood by one of ordinary skill in the art, each embodiment disclosed herein can comprise, consist essentially of or consist of its particular stated element, step, ingredient or component. As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. As used herein, a material effect would cause a statistically-significant reduction in the anti-tumor effects of a claimed composition or method in at least two measures of anti-tumor activity.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

SEQUENCE LISTING

```
Sequence total quantity: 4
SEQ ID NO: 1          moltype = AA  length = 6
FEATURE               Location/Qualifiers
source                1..6
                      mol_type = protein
                      note = GFOGER Adhesion Motif
                      note = 4Hyp
                      organism = synthetic construct
SEQUENCE: 1
GFXGER                                                    6

SEQ ID NO: 2          moltype = AA  length = 47
FEATURE               Location/Qualifiers
source                1..47
                      mol_type = protein
                      note = GFOGER Peptide
                      note = 4Hyp
                      organism = synthetic construct
SEQUENCE: 2
GGYGGGPCGP PGPPGPPGPP GPPGFXGERG PPGPPGPPGP PGPPGPC      47

SEQ ID NO: 3          moltype = AA  length = 532
FEATURE               Location/Qualifiers
source                1..532
                      mol_type = protein
                      note = ICAM-1 Cell Adhesion Molecule
```

-continued

```
                        organism = Homo sapiens
SEQUENCE: 3
MAPSSPRPAL PALLVLLGAL FPGPGNAQTS VSPSKVILPR GGSVLVTCST SCDQPKLLGI  60
ETPLPKKELL LPGNNRKVYE LSNVQEDSQP MCYSNCPDGQ STAKTFLTVY WTPERVELAP  120
LPSWQPVGKN LTLRCQVEGG APRANLTVVL LRGEKELKRE PAVGEPAEVT TTVLVRRDHH  180
GANFSCRTEL DLRPQGLELF ENTSAPYQLQ TFVLPATPPQ LVSPRVLEVD TQGTVVCSLD  240
GLFPVSEAQV HLALGDQRLN PTVTYGNDSF SAKASVSVTA EDEGTQRLTC AVILGNQSQE  300
TLQTVTIYSF PAPNVILTKP EVSEGTEVTV KCEAHPRAKV TLNGVPAQPL GPRAQLLLKA  360
TPEDNGRSFS CSATLEVAGQ LIHKNQTREL RVLYGPRLDE RDCPGNWTWP ENSQQTPMCQ  420
AWGNPLPELK CLKDGTFPLP IGESVTVTRD LEGTYLCRAR STQGEVTREV TVNVLSPRYE  480
IVIITVVAAA VIMGTAGLST YLYNRQRKIK KYRLQQAQKG TPMKPNTQAT PP           532

SEQ ID NO: 4              moltype = AA  length = 368
FEATURE                  Location/Qualifiers
source                   1..368
                         mol_type = protein
                         note = FN-III7-10 Fragment
                         organism = Homo sapiens
SEQUENCE: 4
PLSPPTNLHL EANPDTGVLT VSWERSTTPD ITGYRITTTP TNGQQGNSLE EVVHADQSSC  60
TFDNLSPGLE YNVSVYTVKD DKESVPISDT IIPAVPPPTD LRFTNIGPDT MRVTWAPPPS  120
IDLTNFLVRY SPVKNEEDVA ELSISPSDNA VVLTNLLPGT EYVVSVSSVY EQHESTPLRG  180
RQKTGLDSPT GIDFSDITAN SFTVHWIAPR ATITGYRIRH HPEHFSGRPR EDRVPHSRNS  240
ITLTNLTPGT EYVVSIVALN GREESPLLIG QQSTVSDVPR DLEVVAATPT SLLISWDAPA  300
VTVRYYRITY GETGGNSPVQ EFTVPGSKST ATISGLKPGV DYTITVYAVT GRGDSPASSK  360
PISINYRT                                                           368
```

What is claimed is:

1. A method comprising adding tumor reactive lymphocytes into a porous scaffold comprising at least one antibody selected from an anti-CD3 antibody, an anti-CD28 antibody, an anti-CD137 antibody, an anti-CD27 antibody, an anti-CD80 antibody, an anti-CD86 antibody, an anti-OX40 antibody, an anti-CD40 antibody, an anti-CD7 antibody, and an anti-B7-H3 antibody.

2. The method of claim 1, wherein the porous scaffold comprises collagen or alginate.

3. The method of claim 2, wherein the alginate comprises modified alginate.

4. The method of claim 1, further comprising forming the porous scaffold by casting, freeze-drying, or crosslinking.

5. The method of claim 1, wherein the tumor reactive lymphocytes are T cells or NK cells.

6. The method of claim 5, wherein the T cells or NK cells are genetically-modified to express a chimeric antigen receptor (CAR), an αβ T-cell receptor, a γΔ T-cell receptor, or a proinflammatory cytokine.

7. The method of claim 1, further comprising adding an immune stimulant to the porous scaffold.

8. A method comprising
genetically modifying lymphocytes; and
adding genetically modified lymphocytes into a porous scaffold comprising at least one antibody selected from an anti-CD3 antibody, an anti-CD28 antibody, and an anti-CD137 antibody.

9. The method of claim 8, wherein the lymphocytes are T cells or NK cells.

10. The method of claim 8, wherein the lymphocytes are genetically-modified to express a chimeric antigen receptor (CAR) or an αβ T-cell receptor, or a proinflammatory cytokine.

11. The method of claim 8, wherein the genetically modifying comprises introducing a gene by transfection, electroporation, microinjection, lipofection, calcium phosphate mediated transfection, viral or bacteriophage vector infection, cell fusion, chromosome-mediated gene transfer, microcell-mediated gene transfer, or spheroplast fusion.

12. The method of claim 8, wherein the adding genetically modified lymphocytes occurs prior to a time of implantation into a subject.

13. The method of claim 8, further comprising implanting the porous scaffold into an anatomical site of a subject.

14. The method of claim 8, wherein the porous scaffold comprises collagen or alginate.

15. The method of claim 14, wherein the alginate comprises a modified alginate.

16. The method of claim 8, further comprising forming the porous scaffold by casting, freeze-drying, or crosslinking.

17. The method of claim 8, further comprising adding an immune stimulant to the porous scaffold.

18. A method of forming a porous scaffold comprising
obtaining collagen or alginate;
obtaining at least one antibody selected from an anti-CD3 antibody, an anti-CD28 antibody, and an anti-CD137 antibody; and
adding the collagen or alginate and at least one antibody into a solution that results in formation of a three-dimensional gel comprising the collagen or alginate and the at least one antibody;
thereby forming the porous scaffold.

19. The method of claim 18, wherein porous scaffold comprises collagen and the solution comprises water or acetic acid and the three-dimensional gel forms through crosslinking.

20. The method of claim 18, further comprising adding an immune stimulant to the porous scaffold.

21. The method of claim 18, further comprising adding tumor reactive lymphocytes into the porous scaffold.

* * * * *